US007749753B2

(12) United States Patent
Kanda et al.

(10) Patent No.: US 7,749,753 B2
(45) Date of Patent: Jul. 6, 2010

(54) CELLS IN WHICH ACTIVITY OF THE PROTEIN INVOLVED IN TRANSPORTATION OF GDP-FUCOSE IS REDUCED OR LOST

(75) Inventors: Yutaka Kanda, Machida (JP); Mitsuo Satoh, Machida (JP); Katsuhiro Mori, Machida (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 1208 days.

(21) Appl. No.: 10/409,600

(22) Filed: Apr. 9, 2003

(65) Prior Publication Data

US 2004/0110282 A1    Jun. 10, 2004

(30) Foreign Application Priority Data

Apr. 9, 2002    (JP) .............................. 2002-106952

(51) Int. Cl.
*C12P 21/02* (2006.01)
*C07H 21/04* (2006.01)
(52) U.S. Cl. .................... 435/325; 435/69.1; 435/193; 435/317.1; 435/320.1; 435/455; 536/24.5; 536/24.31; 536/24.1
(58) Field of Classification Search ........................ None
See application file for complete search history.

(56) References Cited

U.S. PATENT DOCUMENTS

| 6,350,868 B1 | 2/2002 | Weston et al. | |
|---|---|---|---|
| 6,946,292 B2 * | 9/2005 | Kanda et al. ................. | 435/326 |
| 2003/0175969 A1 | 9/2003 | Beliard et al. | |
| 2004/0093621 A1 | 5/2004 | Shitara et al. | |

FOREIGN PATENT DOCUMENTS

| EP | 1 176 195 | 1/2002 |
|---|---|---|
| EP | 1 176 195 A1 | 1/2002 |
| EP | 1 498 490 | 1/2005 |
| WO | WO 94/02616 | 2/1994 |
| WO | WO 00/64262 | 11/2000 |

OTHER PUBLICATIONS

Luhn et al. The gene defective in leukocyte adhesion deficiency II encodes a putative GDP-fucose transporter. Nature Genetics, 2001, vol. 28: 69-72. Nature Publishing Group.*
Reitman et al. Mouse lymphoma cell lines resistant to pea lectin are defective in fucose metabolism. Journal of Biological Chemistry, 1980, vol. 255, No. 20: 9900-9906.*
Prati et al. Antisense strategies for glycosylation engineering of chinese hamster ovary (CHO) cells. Biotechnology and Bioengineering 1998, vol. 59, No. 4: 445-450.*
Wild et al. Leukocyte adhesion deficiency II: therapy and genetic defect. Cells Tissues Organs 2002, vol. 172: 161-173.*
Lubke, T. et al., Complementation cloning identifies CDG-IIc, a new type of congenital disorders of glycosylation, as a GDP-fucose transporter deficiency, Nature Genetics, 2001, vol. 28(1), pp. 73-76.

Luhn, K. et al., The gene defective in leukocyte adhesion deficiency II encodes a putative GDP-fucose transporter, Nature Genetics, 2001, vol. 28(1), pp. 69-72.
Roos, D. et al., Hematologically Important Mutations: Leukocyte Adhesion Deficiency, Blood Cells, Molecules, and Diseases, 2001, vol. 27(6), pp. 1000-1004.
Puglielli, L. et al., Reconstitution, Identification, and Purification of the Rat Liver Golgi Membrane GDP-fucose Transporter, The Journal of Biological Chemistry, 1999, vol. 274, No. 50, pp. 35596-35600.
Shinkawa, T. et al., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity, The Journal of Biological Chemistry, 2003, vol. 278, No. 5, pp. 3466-3473.
Zhou, Y. et al., Post-transcriptional suppression of gene expression in Xenopus embryos by small interfering RNA, Nucleic Acids Research, 2002, vol. 30, No. 7, pp. 1664-1669.
Domino et al, Molecular and Cellular Biology, Dec. 2001, vol. 21, No. 24, pp. 8336-8345.
Bartunkova et al, APMIS, Jun. 2000, vol. 108, No. 6, pp. 409-416.
Huang et al, The Journal of Biological Chemistry, 2000, vol. 275, No. 40, pp. 31353-31360.
Yamane-Ohnuki et al, Biotechnology and Bioengineering, 2004, vol. 87, No. 5, pp. 614-622.
Prati et al, Biotechnology and Bioengineering, 1998, vol. 59, No. 4, pp. 445-450.
Supplementary Partial European Search Report dated Jul. 22, 2005 issued in corresponding EP 03 72 0896.4.
Bartunkova et al, APMIS, 2000, vol. 108, No. 6, 409-416.
Hennet et al, Biochemica et Biophysica Acta 1999, vol. 1473, No. 1, pp. 123-136.
Liu et al, Journal of Cancer Research and Clinical Oncology, 2002, vol. 128, No. 4, pp. 189-196.
Javaud et al, Molecular Biology and Evolution, 2000, vol. 17, No. 11, pp. 1661-1672.
Takahashi et al, Glycobiology, 2000, vol. 10, No. 5, pp. 503-510.
Christensen et al, Glycobiology, 2000, vol. 10, No. 9, pp. 931-939.
Sousa et al, The Journal of Biological Chemistry, 2003, vol. 278, No. 9, pp. 7624-7629.
Okajima et al, Cell, 2002, vol. 111, No. 6, pp. 893-904.
Jen et al, Stem Cells, 2000, vol. 18, pp. 307-319.
Mori et al, Biotechnology and Bioengineering, 2004, vol. 88, No. 7, pp. 901-908.

* cited by examiner

*Primary Examiner*—Kimberly Chong
(74) *Attorney, Agent, or Firm*—Sughrue Mion, PLLC

(57) ABSTRACT

A cell in which the activity of a protein relating to transport of an intracellular sugar nucleotide, GDP-fucose, to the Golgi body is more decreased or deleted than its parent cell; a process for producing an antibody composition using the cell; a transgenic non-human animal or plant or the progenies thereof, in which genome is modified so as to have a decreased or deleted activity of a protein relating to transport of an intracellular sugar nucleotide, GDP-fucose, to the Golgi body; a process for producing an antibody composition from the animal or plant; and a medicament comprising the antibody composition.

11 Claims, 12 Drawing Sheets

FIG. 3
CHO/GDPfT Δ30-CCR4 antibody
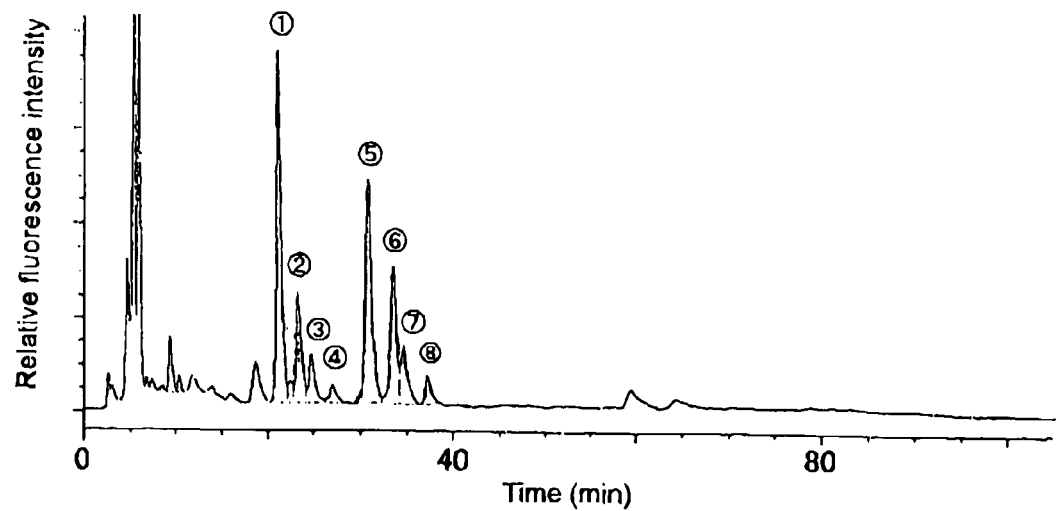
CHO/pcDNA-CCR4 antibody
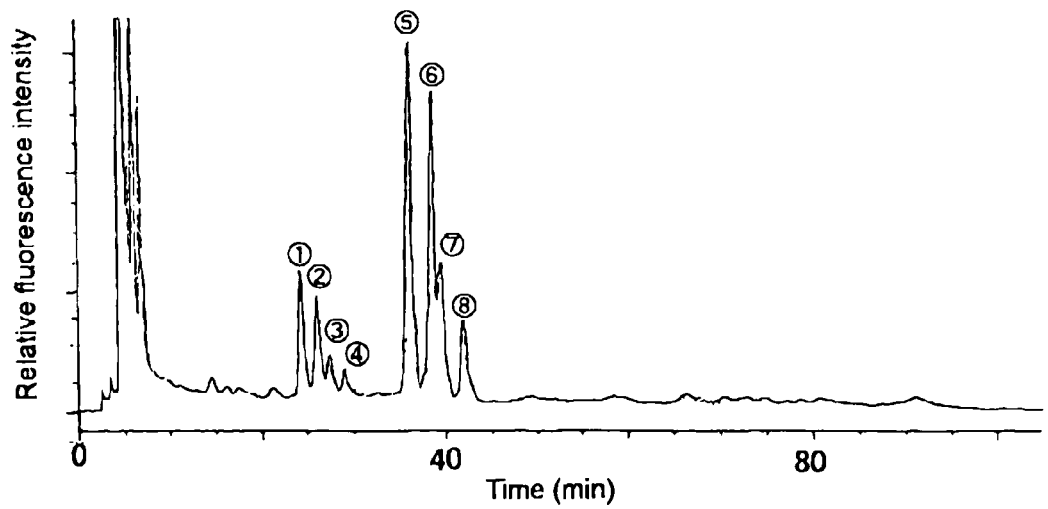

FIG. 4

```
      -210       -200       -190       -180       -170       -160
      TTAGCTAGGCCCCTTCTCCCTTCCCTGGGTCTTGTCTCATGACCCCCTGCCCCGCCCGGG
      -150       -140       -130       -120       -110       -100
      AGCGAGCGCGATGTGGAGCAGTGCCTCTGGCAAGCAGAACTTCACCCAAGCCATGTGACA
                                                CHO_GFT_FW→
       -90        -80        -70        -60        -50        -40
      ATTGAAGGCTGTACCCCCAGACCCTAACATCTTGGAGCCCTGTAGACCAGGGAGTGCTTC
       -30        -20        -10          1         10         20
      TGGCCGTGGGGTGACCTAGCTCTTCTACCACCATGAACAGGGCCCCTCTGAAGCGGTCCA
                                           M  N  R  A  P  L  K  R  S
                                           └─────────────→ ORF
```

5' Nontranslated region nucleotide sequence

```
       980        990       1000       1100       1110       1120
      AGCTCCAAAGAGGGTGAGAAGAGCGCTATTGGGGTGTGAGCTTGTTCAGGGACCTGGGAC
       S  S  K  E  G  E  K  S  A  I  G  V  *
                                 ORF ←─────────────┘
       1130
      TGAACCCAAG
      ←CHO_GFT_RV
```

3' Nontranslated region nucleotide sequence

FIG. 12

|  | Clone 32-05-09 | 32-05-09-H12 |
|---|---|---|
| GDP-fucose transporter mRNA | | #1 |
| | | #2 |
| | | #3 |
| β-Actin mRNA | | #1 |
| | | #2 |
| | | #3 |

CELLS IN WHICH ACTIVITY OF THE PROTEIN INVOLVED IN TRANSPORTATION OF GDP-FUCOSE IS REDUCED OR LOST

The present application claims benefit of JP 2002-106952, filed 9 Apr. 2002, the entire contents of which is incorporated herein by reference.

BACKGROUND OF THE INVENTION

1. Field of the Invention

The present invention relates to a cell in which the activity of a protein relating to transport of an intracellular sugar nucleotide, GDP-fucose, to the Golgi body is more decreased or deleted than its parent cell; a process for producing an antibody composition using the cell; a transgenic non-human animal or plant or the progenies thereof, in which genome is modified so as to have a decreased or deleted activity of a protein relating to transport of an intracellular sugar nucleotide, GDP-fucose, to the Golgi body; a process for producing an antibody composition from the animal or plant; and a medicament comprising the antibody composition.

2. Brief Description of the Background Art

In the Fc region of an antibody of an IgG type, two N-glycoside-linked sugar chain binding sites are present. In serum IgG, to the sugar chain binding site, generally, binds a complex type sugar chain having plural branches and in which addition of sialic acid or bisecting N-acetylglucosamine is low. It is known that there is variety regarding the addition of galactose to the non-reducing end of the complex type sugar chain and the addition of fucose to the N-acetylglucosamine in the reducing end [*Biochemistry*, 36, 130 (1997)].

It has been considered that such a structure of a sugar chain is determined by a glycosyltransferase which synthesizes a sugar chain and a glycolytic enzyme which hydrolyzes the sugar chain.

Synthesis of an N-glycoside-linked sugar chain is described below.

Glycoproteins are modified with a sugar chain in the endoplasmic reticulum (hereinafter referred to as "ER") lumen. During the biosynthesis step of the N-glycoside-linked sugar chain, a relatively large sugar chain is transferred to the polypeptide chain which is elongating in the ER lumen. In the transformation, the sugar chain is firstly added in succession to phosphate groups of a long chain lipid carrier comprising about 20 α-isoprene units, which is called dolichol phosphate (hereinafter sometimes referred to as "P-Dol"). That is, N-acetylglucosamine is transferred to dolichol phosphate to thereby form GlcNAc-P-P-Dol and then one more GlcNAc is transferred to form GlcNAc-GlcNAc-P-P-Dol. Next, five mannoses (hereinafter mannose is also referred to as "Man") are transferred to thereby form (Man)$_5$-(GlcNAc)$_2$-P-P-Dol and then four Man's and three glucoses (hereinafter glucose is also referred to as "Glc") are transferred. Thus, a sugar chain precursor, (Glc)$_3$-(Man)$_9$-(GlcNAc)$_2$-P-P-Dol, called core oligosaccharide is formed. The sugar chain precursor comprising 14 sugars is transferred as a mass to a polypeptide having an asparagine-X-serine or asparagine-X-threonine sequence in the ER lumen. In the reaction, dolichol pyrophosphate (P-P-Dol) bound to the core oligosaccharide is released but again becomes dolichol phosphate by hydrolysis with pyrophosphatase and is recycled. Trimming of the sugar chain immediately starts after the sugar chain binds to the polypeptide. That is, 3 Glc's and 1 or 2 Man's are eliminated on the ER, and it is known that α1,2-glucosidase I, α-1,3-glucosidase II and α-1,2-mannosidase relates to the elimination.

The glycoprotein which was subjected to trimming on the ER is transferred to the Golgi body and are variously modified. In the cis part of the Golgi body, N-acetylglucosamine phosphotransferase which relates to addition of mannose phosphate, N-acetylglucosamine 1-phosphodiester α-N-acetylglucosaminidase and α-mannosidase I are present and reduce the Man residues to 5. In the medium part of the Golgi body, N-acetylglucosamine transferase I (GnTI) which relates to addition of the first outside GlcNAc of the complex type N-glycoside-linked sugar chain, α-mannosidase II which relates to elimination of 2 Man's, N-acetylglucosamine transferase II (GnTII) which relates to addition of the second GlcNAc from the outside and α1,6-fucosyltransferase which relates to addition of fucose to the reducing end N-acetylglucosamine are present. In the trans part of the Golgi body, galactose transferase which relates to addition of galactose and sialyltransferase which relates to addition of sialic acid such as N-acetylneuraminic acid are present. It is known that N-glycoside-linked sugar chain is formed by activities of these various enzymes.

Regarding the sugar chain of an antibody, Boyd et al., have examined effects of a sugar chain on the antibody-dependent cell-mediated cytotoxic activity (hereinafter referred to as "ADCC activity") and complement-dependent cytotoxic activity (hereinafter referred to as "CDC activity") by treating a human CDR-grafted antibody CAMPATH-1H (human IgG1 subclass) produced by a Chinese hamster ovary cell (CHO cell) or a mouse myeloma produced by NS0 cell with various sugar hydrolyzing enzymes, and reported that elimination of the non-reducing end sialic acid did not have influence upon both activities, but the CDC activity alone was affected by further removal of galactose residue and about 50% of the activity was decreased, and that complete removal of the sugar chain caused disappearance of both activities [*Molecular Immunol.*, 32, 1311 (1995)]. Also, Lifely et al. have analyzed the sugar chain bound to a human CDR-grafted antibody CAMPATH-1H (human IgG1 subclass) which was produced by CHO cell, NS0 cell or rat myeloma YO cell, measured its ADCC activity, and reported that the CAMPATH-1H produced by YO cell showed the highest ADCC activity, suggesting that N-acetylglucosamine (hereinafter sometimes referred to as "GlcNAc") at the bisecting position is important for the activity [*Glycobiology*, 5, 813 (1995); WO 99/54342].

Furthermore, regarding a sugar chain in an antibody, it is reported that addition-modification of fucose to N-acetylglucosamine in the reducing end in the N-glycoside-linked sugar chain of an antibody changes the ADCC activity of the antibody greatly (WO00/61739). These reports indicate that the structure of the sugar chain plays an important role in the effector functions of human antibodies of IgG1 subclass.

In general, most of the humanized antibodies of which application to medicaments is in consideration are prepared by using genetic recombination techniques and produced by using Chinese hamster ovary tissue-derived CHO cell as the host cell. However, as described above, since the sugar chain structure plays a remarkably important role in the effector function of antibodies and differences of the sugar chain structure of glycoproteins depend on host cells which produce the glycoproteins, development of a host cell which can be used for the production of an antibody having higher effector function is desired.

In order to adjust the activity of an enzyme relating to modification of a sugar chain in a host cell and modify the sugar chain structure of the produced glycoprotein, a method in which an inhibitor against an enzyme relating to the modification of a sugar chain is applied has been attempted.

Examples of an inhibitor against an enzyme relating to the modification of a sugar chain include tunicamycin which selectively inhibits formation of GlcNAc-P-P-Dol which is the first step of the formation of a core oligosaccharide which is a precursor of an N-glycoside-linked sugar chain, castanospermin and N-methyl-1-deoxynojirimycin which are inhibitors of glycosidase I, bromocondulitol which is an inhibitor of glycosidase II, 1-deoxynojirimycin and 1,4-dioxy-1,4-imino-D-mannitol which are inhibitors of mannosidase I, swainsonine which is an inhibitor of mannosidase II and the like. Examples of an inhibitor specific for a glycosyltransferase include deoxy derivatives of substrates against N-acetylglucosamine transferase V (GnTV) and the like [*Glycobiology Series 2—Destiny of Sugar Chain in Cell* (Kodan-sha Scientific), edited by Katsutaka Nagai, Senichiro Hakomori and Akira Kobata (1993)]. Also, it is known that 1-deoxynojirimycin inhibits synthesis of a complex type sugar chain and increases the ratio of high mannose type and hybrid type sugar chains. Actually, it has been reported that sugar chain structure of IgG produced by a hybridoma was changed and properties such as antigen binding activity or DCC activity were changed when the inhibitors such as castonospermine, N-methyl-1-deoxynojirimycin, swainsonine and tunicamycin were added to a medium [*Molecular Immunol.*, 26, 1113 (1989)]. However, since these inhibitors have weak specificity and also cannot inhibit the target enzyme sufficiently, it is difficult to surely control the sugar chain structure of the produced antibody.

Also, an attempt has been made to modify the sugar chain structure of a produced glycoprotein by introducing an enzyme gene relating to the modification of sugar chains into the host cell, and specifically, it has been reported that 1) it is possible to produce a protein in which sialic acid is added in a large number to the non-reducing end of a sugar chain by introducing rat β-galactoside-α-2,6-sialyltransferase into CHO cell [*J. Biol. Chem.*, 261, 13848 (1989)], 2) it is possible to express an H antigen in which fucose (hereinafter also referred to as "Fuc") is added to the non-reducing end of a sugar chain (Fucα1-2Galβ1-) by introducing human β-galactoside-2-α-fucosyltransferase into mouse L cell [*Science*, 252, 1668 (1991)], and 3) it is possible to produce an antibody having a high addition ratio of the bisecting N-acetylglucosamine of N-glycoside binding sugar chains by producing an antibody using a β-1,4-N-acetylglucosamine transferase III (GnTIII)-introduced CHO cell [*Glycobiology.*, 5, 813 (1995): WO 99/54342]. When the antibody was expressed by using a GnTIII-introduced CHO cell, it showed 16 times higher ADCC activity than the antibody expressed in the parent cell. However, since it has been reported that overexpression of GnTIII or β-1,4-N-acetylglucosamine transferase V (GnTV) shows toxicity upon CHO cell, it is not suitable for the production of antibody medicaments.

It has also been reported on a production example of a glycoprotein in which a produced sugar chain structure was changed by using, as a host cell, a mutant in which the activity of an enzyme gene relating to the modification of sugar chains was changed, and as its example, it has been reported that an antibody having a high mannose type sugar chain structure was produced by using a mutant clone of CHO cell in which the activity of 4-N-acetylglucosamine transferase I (GnTI) [*J. Immunol.*, 160, 3393 (1998)] was deleted. In addition, expression of an antibody having a sugar chain structure in which sialic acid is not bound to the non-reducing side in the sugar chain and an expression example of an antibody having a sugar chain structure to which galactose is not bound, by using a CMP-sialic acid transporter- or UDP-galactose transporter-deficient cell line, respectively, have been reported, but no antibody having improved effector functions suitable for the application to medicaments has been found [*J. Immunol.*, 160, 3393 (1998)]. Since the mutant clones have been obtained as clones resulting from the introduction of random mutation by mutagen treatment, they are not suitable as clones used in the production of pharmaceutical preparations.

Thus, in order to modify a sugar chain structure of a produced glycoprotein, attempts have been made to control the activity of an enzyme relating to the modification of sugar chains in host cells. However, in fact, since the sugar chain modification mechanism is varied and complicated and it cannot be said that physiological roles of sugar chains has been sufficiently revealed, it is the present situation that trial and error are repeated. Particularly, it has been revealed gradually that effector functions of antibodies have great influences by sugar chain structures, but a host cell capable of producing antibody molecules modified with a most suitable sugar chain structure has not been obtained yet.

SUMMARY OF THE INVENTION

The present invention relates to the following (1) to (70).

(1) A cell in which the activity of a protein relating to transport of an intracellular sugar nucleotide, GDP-fucose, to the Golgi body is more decreased or deleted than its parent cell.

(2) The cell according to (1), wherein the activity of a protein relating to transport of an intracellular sugar nucleotide, GDP-fucose, to the Golgi body is decreased or deleted by a genetic engineering technique.

(3) The cell according to any one of (2) to (5), wherein the genetic engineering technique is selected from the group consisting of (a) to (d):

(a) a gene disruption technique which comprises targeting a gene encoding a protein relating to transport of an intracellular sugar nucleotide, GDP-fucose, to the Golgi body;

(b) a technique for introducing a dominant negative mutant of a protein relating to transport of an intracellular sugar nucleotide, GDP-fucose, to the Golgi body, (c) a technique for introducing mutation into a protein relating to transport of an intracellular sugar nucleotide, GDP-fucose, to the Golgi body, (d) a technique for suppressing transcription and/or translation of a protein relating to transport of an intracellular sugar nucleotide, GDP-fucose, to the Golgi body.

(4) The cell according to (3), wherein the dominant negative mutant of a protein relating to transport of an intracellular sugar nucleotide, GDP-fucose, to the Golgi body is an N-terminal deletion mutant of a protein relating to transport of an intracellular sugar nucleotide, GDP-fucose, to the Golgi body.

(5) The cell according to (4), wherein the N-terminal deletion mutant of a protein relating to transport of an intracellular sugar nucleotide, GDP-fucose, to the Golgi body is an N-terminal deletion mutant in which 30 amino acids at the N-terminal of a protein relating to transport of an intracellular sugar nucleotide, GDP-fucose, to the Golgi body are deleted.

(6) The cell according to (3), wherein the technique for suppressing transcription and/or translation of a protein relating to transport of an intracellular sugar nucleotide, GDP-fucose, to the Golgi body is an RNAi (RNA interference) method.

(7) The cell according to (6), wherein a double-stranded RNA comprising an RNA and its complementary RNA is introduced into or expressed in the cell, said RNA comprised in the double-stranded RNA being selected from the group consisting of the following (a) to (d) and being capable of decreasing the amount of mRNA of a protein relating to transport of an intracellular sugar nucleotide, GDP-fucose, to the Golgi body:

(a) an RNA corresponding to a DNA comprising a nucleotide sequence of continuous 10 to 30 nucleotides in the nucleotide sequence represented by SEQ ID NO:1;

(b) an RNA corresponding to a DNA comprising a nucleotide sequence of continuous 10 to 30 nucleotides in the nucleotide sequence represented by SEQ ID NO:3;

(c) an RNA corresponding to a DNA comprising a nucleotide sequence of continuous 10 to 30 nucleotides in the nucleotide sequence represented by SEQ ID NO:29;

(d) an RNA corresponding to a DNA comprising a nucleotide sequence of continuous 10 to 30 nucleotides in the nucleotide sequence represented by SEQ ID NO:30.

(8) The cell according to (6) or (7), wherein the double-stranded RNA comprising a RNA selected from the group consisting of (a) and (b) and its complementary RNA is introduced into or expressed in the cell to thereby decrease the amount of mRNA of a protein relating to transport of an intracellular sugar nucleotide, GDP-fucose, to the Golgi body:

(a) an RNA comprising the nucleotide sequence represented by SEQ ID NO:33;

(b) an RNA which comprises a nucleotide sequence in which one or a few nucleotide are deleted or added in the nucleotide sequence represented by SEQ ID NO:33 and has substantially the same RNAi activity as the nucleotide sequence represented by SEQ ID NO:33.

(9) The cell according to (7) or (8), wherein the double-stranded RNA is introduced into the cell by using a vector into which a DNA corresponding to the RNA according to (7) or (8) and its complementary DNA are introduced.

(10) The cell according to any one of (1) to (9), wherein the protein relating to transport of an intracellular sugar nucleotide, GDP-fucose, to the Golgi body is a GDP-fucose transporter.

(11) The cell according to (10), wherein the GDP-fucose transporter is a protein encoded by a DNA selected from the group consisting of the following (a) to (h):

(a) a DNA comprising the nucleotide sequence represented by SEQ ID NO:1;

(b) a DNA comprising the nucleotide sequence represented by SEQ ID NO:3;

(c) a DNA comprising the nucleotide sequence represented by SEQ ID NO:29;

(d) a DNA comprising the nucleotide sequence represented by SEQ ID NO:30;

(e) a DNA which hybridizes with a DNA comprising the nucleotide sequence represented by SEQ ID NO:1 under stringent conditions and having a GDP-fucose transporter activity;

(f) a DNA which hybridizes with a DNA comprising the nucleotide sequence represented by SEQ ID NO:3 under stringent conditions and having a GDP-fucose transporter activity;

(g) a DNA which hybridizes with a DNA comprising the nucleotide sequence represented by SEQ ID NO:29 under stringent conditions and having a GDP-fucose transporter activity;

(h) a DNA which hybridizes with a DNA comprising the nucleotide sequence represented by SEQ ID NO:30 under stringent conditions and having a GDP-fucose transporter activity.

(12) The cell according to (10), wherein the GDP-fucose transporter is a protein selected from the group consisting of the following (a) to (l):

(a) a protein comprising the amino acid sequence represented by SEQ ID NO:2;

(b) a protein comprising the amino acid sequence represented by SEQ ID NO:4;

(c) a protein comprising the amino acid sequence represented by SEQ ID NO:31;

(d) a protein comprising the amino acid sequence represented by SEQ ID NO:32;

(e) a protein which comprises an amino acid sequence in which at least one amino acid is deleted, substituted, inserted and/or added in the amino acid sequence represented by SEQ ID NO:2 and has a GDP-fucose transporter activity;

(f) a protein which comprises an amino acid sequence in which at least one amino acid is deleted, substituted, inserted and/or added in the amino acid sequence represented by SEQ ID NO:4 and has a GDP-fucose transporter activity;

(g) a protein which comprises an amino acid sequence in which at least one amino acid is deleted, substituted, inserted and/or added in the amino acid sequence represented by SEQ ID NO:31 and has a GDP-fucose transporter activity;

(h) a protein which comprises an amino acid sequence in which at least one amino acid is deleted, substituted, inserted and/or added in the amino acid sequence represented by SEQ ID NO:32 and has a GDP-fucose transporter activity;

(i) a protein which comprises an amino acid sequence having a homology of at least 80% with the amino acid sequence represented by SEQ ID NO:2 and has a GDP-fucose transporter activity;

(j) a protein which comprises an amino acid sequence having a homology of at least 80% with the amino acid sequence represented by SEQ ID NO:4 and has a GDP-fucose transporter activity, (k) a protein which comprises an amino acid sequence having a homology of at least 80% with the amino acid sequence represented by SEQ ID NO:31 and has a GDP-fucose transporter activity;

(l) a protein which comprises an amino acid sequence having a homology of at least 80% with the amino acid sequence represented by SEQ ID NO:32 and has a GDP-fucose transporter activity.

(13) The cell according to any one of (1) to (12), which is resistant to a lectin which recognizes a sugar chain in which 1-position of fucose is bound to 6-position of N-acetylglucosamine in the reducing end through α-bond in a complex N-glycoside-linked sugar chain.

(14) The cell according to (13), which is resistant to at least one lectin selected from the group consisting of the following (a) to (d):

(a) a *Lens culinaris* lectin;

(b) a *Pisum sativum* lectin;

(c) a *Vicia faba* lectin;

(d) an *Aleuria aurantia* lectin.

(15) The cell according to any one of (1) to (14), wherein the cell is selected from the group consisting of a yeast, an animal cell, an insect cell and a plant cell.

(16) The cell according to any one of (1) to (15), which is selected from the group consisting of the following (a) to (j):
(a) a CHO cell derived from a Chinese hamster ovary tissue;
(b) a rat myeloma cell line YB2/3HL.P2.G11.16Ag.20 cell;
(c) a mouse myeloma cell line NS0 cell;
(d) a mouse myeloma cell line SP2/0-Ag14 cell;
(e) a BHK cell derived from a Syrian hamster kidney tissue;
(f) a hybridoma cell which produces an antibody;
(g) a human leukemic cell line Namalwa cell,
(h) an embryonic stem cell;
(i) a fertilized egg cell;
(j) a plant cell.

(17) A cell in which a gene encoding an antibody molecule is introduced into the cell according to any one of (1) to (16).

(18) The cell according to (17), wherein the antibody molecule is selected from the group consisting of the following (a) to (d):
(a) a human antibody,
(b) a humanized antibody;
(c) an antibody fragment comprising the Fc region of (a) or (b);
(d) a fusion protein comprising the Fc region of (a) or (b).

(19) The cell according to (17) or (18), wherein the antibody molecule belongs to an IgG class.

(20) The cell according to any one of (17) to (19), wherein the antibody composition has a higher antibody-dependent cell-mediated cytotoxic activity than an antibody composition produced by its parent cell,

(21) The cell according to (20), wherein the antibody composition having a higher antibody-dependent cell-mediated cytotoxic activity has a higher ratio of a sugar chain in which fucose is not bound to N-acetylglucosamine in the reducing end in the sugar chain among total complex N-glycoside-linked sugar chains bound to the Fc region in the antibody composition than an antibody composition produced by its parent cell.

(22) The cell according to (21), wherein the ratio of a sugar chain in which fucose is not bound to N-acetylglucosamine in the reducing end through α-bond is 20% or more of total complex N-glycoside-linked sugar chains bound to the Fc region in the antibody composition.

(23) The cell according to (21), wherein the sugar chain in which fucose is not bound is a sugar chain in which 1-position of fucose is not bound to 6-position of N-acetylglucosamine in the reducing end in the complex N-glycoside-linked sugar chain through α-bond.

(24) A process for producing an antibody composition, which comprises using the cell according to any one of (17) to (23).

(25) A process for producing an antibody composition, which comprises culturing the cell according to any one of (17) to (23) in a medium to form and accumulate an antibody composition in the culture; and recovering the antibody composition from the culture.

(26) The process according to (24) or (25), wherein the antibody composition has a higher antibody-dependent cell-mediated cytotoxic activity than an antibody composition produced by its parent cell.

(27) The process according to (26), wherein the antibody composition having a higher antibody-dependent cell-mediated cytotoxic activity has a higher ratio of a sugar chain in which fucose is not bound to N-acetylglucosamine in the reducing end in the sugar chain among total complex N-glycoside-linked sugar chains bound to the Fc region in the antibody composition than an antibody composition produced by its parent cell.

(28) The process according to (27), wherein the ratio of a sugar chain in which fucose is not bound to N-acetylglucosamine in the reducing end through α-bond is 20% or more of total complex N-glycoside-linked sugar chains bound to the Fc region in the antibody composition.

(29) The process according to (27), wherein the sugar chain in which fucose is not bound is a sugar chain in which 1-position of the fucose is not bound to 6-position of N-acetylglucosamine in the reducing end through α-bond in a complex N-glycoside-linked sugar chain.

(30) A transgenic non-human animal or plant or the progenies thereof, in which genome is modified so as to have a decreased or deleted activity of a protein relating to transport of an intracellular sugar nucleotide, GDP-fucose, to the Golgi body.

(31) The transgenic non-human animal or plant or the progenies thereof according to (30), wherein a gene encoding a protein relating to transport of an intracellular sugar nucleotide, GDP-fucose, to the Golgi body is knocked out.

(32) The transgenic non-human animal or plant or the progenies thereof according to (31), wherein all allelic genes on a genome encoding a protein relating to transport of an intracellular sugar nucleotide, GDP-fucose, to the Golgi body is knocked out.

(33) The transgenic non-human animal or plant or the progenies thereof according to any one of (30) to (32), wherein the protein relating to transport of an intracellular sugar nucleotide, GDP-fucose, to the Golgi body is a GDP-fucose transporter.

(34) The transgenic non-human animal or plant or the progenies thereof according to (33), wherein the GDP-fucose transporter is a protein encoded by a DNA selected from the group consisting of the following (a) to (h):
(a) a DNA comprising the nucleotide sequence represented by SEQ ID NO:1;
(b) a DNA comprising the nucleotide sequence represented by SEQ ID NO:3;
(c) a DNA comprising the nucleotide sequence represented by SEQ ID NO:29;
(d) a DNA comprising the nucleotide sequence represented by SEQ ID NO:30;
(e) a DNA which hybridizes with a DNA comprising the nucleotide sequence represented by SEQ ID NO:1 under stringent conditions and having a GDP-fucose transporter activity;
(f) a DNA which hybridizes with a DNA comprising the nucleotide sequence represented by SEQ ID NO:3 under stringent conditions and having a GDP-fucose transporter activity;
(g) a DNA which hybridizes with a DNA comprising the nucleotide sequence represented by SEQ ID NO:29 under stringent conditions and having a GDP-fucose transporter activity;
(h) a DNA which hybridizes with a DNA comprising the nucleotide sequence represented by SEQ ID NO:30 under stringent conditions and having a GDP-fucose transporter activity.

(35) The transgenic non-human animal or plant or the progenies thereof according to (33), wherein the GDP-fucose transporter is a protein selected from the group consisting of the following (a) to (l):

(a) a protein comprising the amino acid sequence represented by SEQ ID NO:2;

(b) a protein comprising the amino acid sequence represented by SEQ ID NO:4;

(c) a protein comprising the amino acid sequence represented by SEQ ID NO:31;

(d) a protein comprising the amino acid sequence represented by SEQ ID NO:32;

(e) a protein which comprises an amino acid sequence in which at least one amino acid is deleted, substituted, inserted and/or added in the amino acid sequence represented by SEQ ID NO:2 and has a GDP-fucose transporter activity;

(f) a protein which comprises an amino acid sequence in which at least one amino acid is deleted, substituted, inserted and/or added in the amino acid sequence represented by SEQ ID NO:4 and has a GDP-fucose transporter activity;

(g) a protein which comprises an amino acid sequence in which at least one amino acid is deleted, substituted, inserted and/or added in the amino acid sequence represented by SEQ ID NO:31 and has a GDP-fucose transporter activity;

(h) a protein which comprises an amino acid sequence in which at least one amino acid is deleted, substituted, inserted and/or added in the amino acid sequence represented by SEQ ID NO:32 and has a GDP-fucose transporter activity;

(i) a protein which comprises an amino acid sequence having a homology of at least 80% with the amino acid sequence represented by SEQ ID NO:2 and has a GDP-fucose transporter activity;

(j) a protein which comprises an amino acid sequence having a homology of at least 80% with the amino acid sequence represented by SEQ ID NO:4 and has a GDP-fucose transporter activity;

(k) a protein which comprises an amino acid sequence having a homology of at least 80% with the amino acid sequence represented by SEQ ID NO:31 and has a GDP-fucose transporter activity;

(l) a protein which comprises an amino acid sequence having a homology of at least 80% with the amino acid sequence represented by SEQ ID NO:32 and has a GDP-fucose transporter activity.

(36) The transgenic non-human animal or the progenies thereof according to any one of (30) to (35), wherein the transgenic non-human animal is selected from the group consisting of cattle, sheep, goat, pig, horse, mouse, rat, fowl, monkey and rabbit.

(37) A transgenic non-human animal or plant or the progenies thereof in which a gene encoding an antibody molecule is introduced into the transgenic non-human animal or plant or the progenies thereof according to any one of (30) to (36).

(38) The transgenic non-human animal or plant or the progenies thereof according to (37), wherein the antibody molecule is selected from the group consisting of the following (a) to (d):

(a) a human antibody;

(b) a humanized antibody;

(c) an antibody fragment comprising the Fc region of (a) or (b);

(d) a fusion protein comprising the Fc region of (a) or (b).

(39) The transgenic non-human animal or plant or the progenies thereof according to (37) or (38), wherein the antibody molecule belongs to an IgG class.

(40) A process for producing an antibody composition, which comprises rearing the transgenic non-human animal or plant or the progenies thereof according to any one of (37) to (39); isolating a tissue or body fluid comprising an antibody composition from the reared non-human animal or plant, and recovering the desired antibody composition from the isolated tissue or body fluid.

(41) A process for producing an antibody composition, which comprises isolating an antibody-producing cell from the transgenic non-human animal or plant or the progenies thereof according to any one of (37) to (39); culturing the isolated antibody-producing cell in a medium to form and accumulate an antibody composition in a culture, and recovering the antibody composition from the culture.

(42) The process according to (40) or (41), wherein the antibody composition has a higher antibody-dependent cell-mediated cytotoxic activity than an antibody composition produced from a non-human animal or plant in which genome is not modified or the progenies thereof.

(43) The process according to (42), wherein the antibody composition having a higher antibody-dependent cell-mediated cytotoxic activity has a higher ratio of a sugar chain in which fucose is not bound to N-acetylglucosamine in the reducing end in the sugar chain among total complex N-glycoside-linked sugar chains bound to the Fc region in the antibody composition than an antibody composition produced by a non-human animal or plant or the progenies thereof in which genome is not modified.

(44) The process according to (43), wherein the ratio of a sugar chain in which fucose is not bound to N-acetylglucosamine in the reducing end through α-bond is 20% or more of total complex N-glycoside-linked sugar chains bound to the Fc region in the antibody composition.

(45) The process according to (43), wherein the sugar chain in which fucose is not bound is a sugar chain in which 1-position of the fucose is not bound to 6-position of N-acetylglucosamine in the reducing end through α-bond in a complex N-glycoside-linked sugar chain.

(46) An antibody composition produced by the process according to any one of (24) to (29).

(47) An antibody composition produced by the process according to any one of (40) to (45).

(48) A medicament comprising as an active ingredient the antibody composition according to (46) or (47).

(49) The medicament according to (48), which is diagnosing, preventing or treating tumor-accompanied diseases, allergy-accompanied diseases, inflammatory-accompanied diseases, autoimmune diseases, cardiovascular diseases, viral infection-accompanied diseases or bacterial infection-accompanied diseases.

(50) A protein which is selected from the group consisting of the following (a) and (b):

(a) a protein comprising the amino acid sequence represented by SEQ ID NO:2;

(b) a protein which comprises an amino acid sequence in which at least one amino acid is deleted, substituted, inserted and/or added in the amino acid sequence represented by SEQ ID NO:2 and has a GDP-fucose transporter activity.

(51) A DNA comprising the nucleotide sequence represented by SEQ ID NO:1.

(52) A target vector for homologous recombination which comprising targeting a GDP-fucose transporter, comprising the full length DNA represented by SEQ ID NO:1 or a part thereof.

(53) A protein which inhibits the function of a GDP-fucose transporter.

(54) The protein according to (53), wherein the protein which inhibits the function of a GDP-fucose transporter is a dominant negative protein of a GDP-fucose transporter.

(55) The protein according to (54), wherein the dominant negative protein of a GDP-fucose transporter is an N-terminal-deleted mutant of GDP-fucose transporter.

(56) The protein according to (55), wherein the N-terminal-deleted mutant of GDP-fucose transporter is an N-terminal-deleted mutant of GDP-fucose transporter in which 30 amino acids are deleted from the N-terminal of the GDP-fucose transporter.

(57) The protein according to any one of (53) to (56), wherein the GDP-fucose transporter is a protein selected from the group consisting of the following (a) to (l):

(a) a protein comprising the amino acid sequence represented by SEQ ID NO:2;

(b) a protein comprising the amino acid sequence represented by SEQ ID NO:4;

(c) a protein comprising the amino acid sequence represented by SEQ ID, NO:31;

(d) a protein comprising the amino acid sequence represented by SEQ ID NO:32;

(e) a protein which comprises an amino acid sequence in which at least one amino acid is deleted, substituted, inserted and/or added in the amino acid sequence represented by SEQ ID NO:2 and has a GDP-fucose transporter activity;

(f) a protein which comprises an amino acid sequence in which at least one amino acid is deleted, substituted, inserted and/or added in the amino acid sequence represented by SEQ ID NO:4 and has a GDP-fucose transporter activity;

(g) a protein which comprises an amino acid sequence in which at least one amino acid is deleted, substituted, inserted and/or added in the amino acid sequence represented by SEQ ID NO:31 and has a GDP-fucose transporter activity;

(h) a protein which comprises an amino acid sequence in which at least one amino acid is deleted, substituted, inserted and/or added in the amino acid sequence represented by SEQ ID NO:32 and has a GDP-fucose transporter activity;

(i) a protein which comprises an amino acid sequence having a homology of at least 80% with the amino acid sequence represented by SEQ ID NO:2 and has a GDP-fucose transporter activity;

(j) a protein which comprises an amino acid sequence having a homology of at least 80% with the amino acid sequence represented by SEQ ID NO:4 and has a GDP-fucose transporter activity;

(k) a protein which comprises an amino acid sequence having a homology of at least 80% with the amino acid sequence represented by SEQ ID NO:31 and has a GDP-fucose transporter activity;

(l) a protein which comprises an amino acid sequence having a homology of at least 80% with the amino acid sequence represented by SEQ ID NO:32 and has a GDP-fucose transporter activity.

(58) A DNA encoding the protein according to any one of (53) to (57).

(59) A double-stranded RNA comprising an RNA selected from the group consisting of (a) and (b) and its complementary RNA:

(a) an RNA comprising the nucleotide sequence represented by SEQ ID NO:33;

(b) an RNA which comprises a nucleotide sequence in which one or a few nucleotide are deleted or added in the nucleotide sequence represented by SEQ ID NO:33 and has substantially the same RNAi activity to a protein relating to transport of an intracellular sugar nucleotide, GDP-fucose, to the Golgi body as the nucleotide sequence represented by SEQ ID NO:33.

(60) A DNA corresponding to the RNA according to (59) and its complementary DNA.

(61) The DNA according to (60), wherein the DNA corresponding to the RNA is represented by the nucleotide sequence represented by SEQ ID NO:16.

(62) A recombinant DNA comprising the DNA according to (60) or (61) and its complementary DNA.

(63) The recombinant DNA according to (62), which is constituted for expressing the double-stranded RNA according to (59).

(64) A transformant obtainable by introducing the recombinant DNA according to (62) or (63) into a cell.

(65) A process for producing a cell resistant to a lectin which recognizes a sugar chain in which 1-position of fucose is bound to 6-position of N-acetylglucosamine in the reducing end through α-bond in a complex N-glycoside-linked sugar chain, which comprises introducing into and/or expressing in a cell the double-stranded RNA according to (59).

(66) The process according to (65), wherein said introduction of the double-stranded RNA is introduction of a vector into which a complementary DNA of the RNA according to (62) or (63) is inserted.

(67) The process according to (65) or (66), wherein the cell resistant to a lectin which recognizes a sugar chain in which 1-position of fucose is bound to 6-position of N-acetylglucosamine in the reducing end through α-bond in a complex N-glycoside-linked sugar chain is a cell resistant to at least one lectin selected from the group consisting of the following (a) to (d):

(a) a *Lens culinaris* lectin;
(b) a *Pisum sativum* lectin;
(c) a *Vicia faba* lectin;
(d) an *Aleuria aurantia* lectin.

(68) The process according to any one of (65) to (67), wherein the cell is selected from the group consisting of a yeast, an animal cell, an insect cell and a plant cell.

(69) The process according to any one of (65) to (68), wherein the cell is selected from the group consisting of the following (a) to (j):

(a) a CHO cell derived from a Chinese hamster ovary tissue;
(b) a rat myeloma cell line YB2/3HL.P2.G11.16Ag.20 cell;
(c) a mouse myeloma cell line NS0 cell;
(d) a mouse myeloma cell line SP2/0-Ag14 cell;
(e) a BHK cell derived from a Syrian hamster kidney tissue;
(f) a hybridoma cell which produces an antibody;
(g) a human leukemic cell line Namalwa cell;
(h) an embryonic stem cell;
(i) a fertilized egg cell;
(j) a plant cell.

(70) Use of the antibody composition according to (43) or (44) in the manufacture of the medicament according to (48) or (49).

BRIEF DESCRIPTION OF THE DRAWINGS

FIG. 3 shows elution patterns of PA-treated sugar chains prepared from anti-CCR4 chimeric antibodies produced by clone CHO/GDPftΔ30-CCR4 and clone CHO/pcDNA-CCR4 obtained by reverse HPLC analysis. The ordinate and the abscissa show the fluorescence intensity and the elution time, respectively.

FIG. 4 shows nucleotide sequences of the untranslated region and the adjacent translation region of a Chinese hamster GDP-fucose transporter. The primer regions designed for obtaining a full length cDNA are shown by underlines. Amino acid sequences deduced from the nucleotide sequences are shown in the lower part of the nucleotide sequence in the translation region.

FIG. 12 is a photograph showing the expression amount of β-actin and GDP-fucose transporter by siRNA expression.

DETAILED DESCRIPTION OF THE INVENTION

Figure 1:
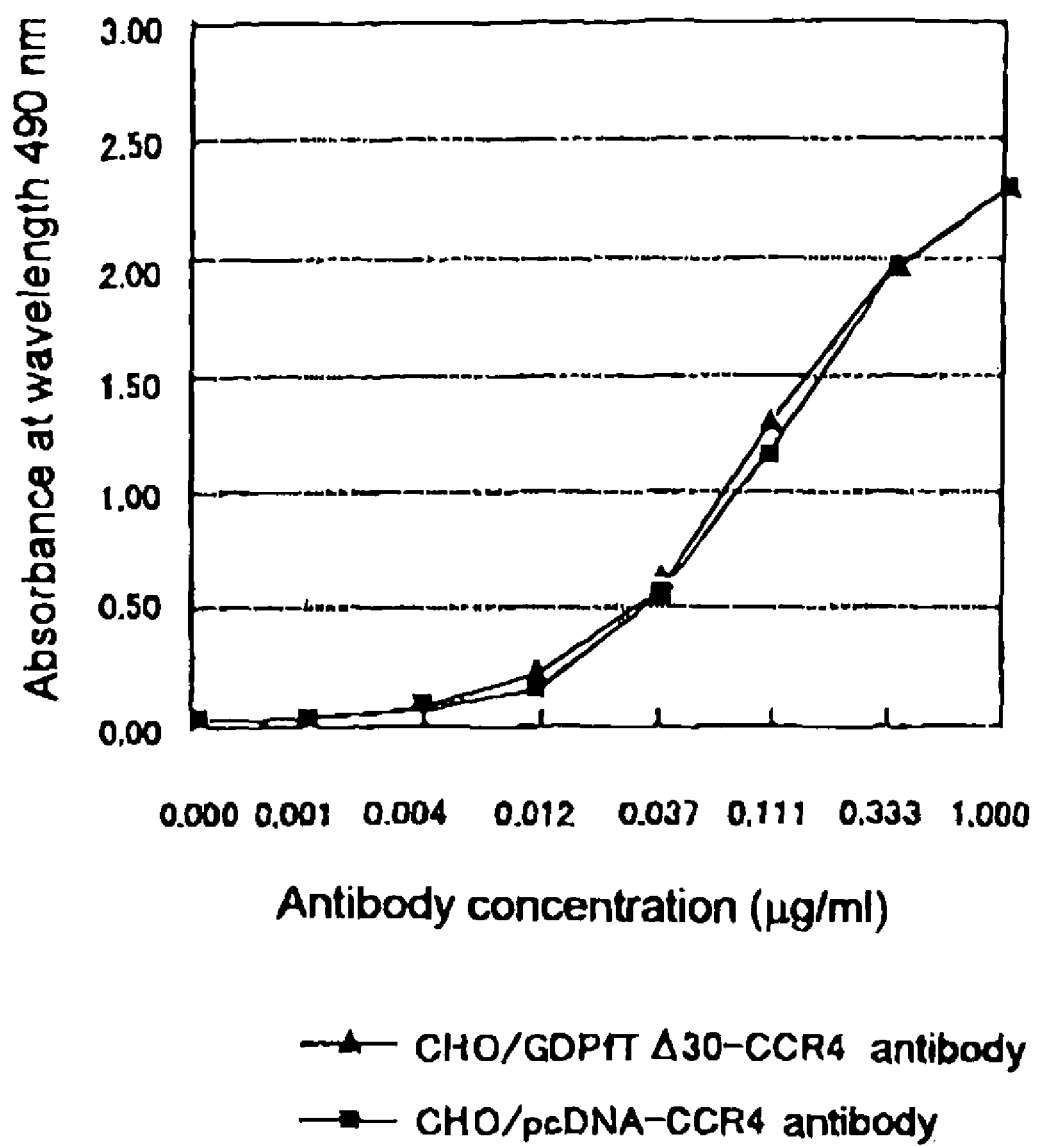
FIG. 1 shows a result of the measurement of CCR4 partial peptide-binding activity by changing antibody concentrations of anti-CCR4 chimeric antibodies produced by clone CHO/GDPftΔ30-CCR4 and clone CHO/pcDNA-CCR4. The ordinate and the abscissa show the binding activity for CCR4 partial peptide as absorbance at a wavelength of 490 nm and the concentration of the anti-CCR4 chimeric antibodies, respectively. "▲" and "■" show antigen-binding activities of CHO/GDPftΔ30-CCR4 antibody and CHO/pcDNA-CCR4 antibody, respectively.

The cell of the present invention in which activity of a protein relating to transport of an intracellular sugar nucleotide, GDP-fucose, to the Golgi body is more decreased or deleted than its parent cell (hereinafter referred to as "host cell of the present invention") may be any cell, so long as it is a cell in which activity of a protein relating to transport of an intracellular sugar nucleotide, GDP-fucose, to the Golgi body (hereinafter referred to as "GDP-fucose transport protein") is more decreased or deleted than its parent cell.

The parent cell means a cell before a method for decreasing or deleting the activity of the GDP-fucose transport protein is carried out.

The parent cell of NS0 cell includes NS0 cells described in literatures such as *BIO/TECHNOLOGY,* 10, 169 (1992) and *Biotechnol. Bioeng.,* 73, 261 (2001), NS0 cell line (RCB 0213) registered at RIKEN Cell Bank, The Institute of Physical and Chemical Research, sub-cell lines obtained by acclimating these cell lines to media in which they can grow, and the like.

The parent cell of SP2/0-Ag14 cell includes SP2/0-Ag14 cells described in literatures such as *J. Immunol.,* 126, 317 (1981), *Nature,* 276, 269 (1978) and *Human Antibodies and Hybridomas,* 3, 129 (1992), SP2/0-Ag14 cell (ATCC CRL-1581) registered at ATCC, sub-cell lines obtained by acclimating these cell lines to media in which they can grow (ATCC CRL-1581.1), and the like.

The parent cell of CHO cell derived from Chinese hamster ovary tissue includes CHO cells described in literatures such as *Journal of Experimental Medicine (Jikken Igaku),* 108, 945 (1958), *Proc. Natl. Acad. Sci. USA,* 60, 1275 (1968), *Genetics,* 55, 513 (1968), *Chromosoma,* 41, 129 (1973), *Methods in Cell Science,* 18, 115 (1996), *Radiation Research,* 148, 260 (1997), *Proc. Natl. Acad. Sci. USA,* 77, 4216 (1980), *Proc. Natl. Acad. Sci. USA,* 60, 1275 (1968), *Cell,* 6, 121 (1975) and *Molecular Cell Genetics,* Appendix I, II (p. 883-900), cell line CHO-K1 (ATCC CCL-61), cell line DUXB11 (ATCC CRL-9096) and cell line Pro-5 (ATCC CRL-1781) registered at ATCC, commercially available cell line CHO-S (Cat # 11619 of Life Technologies), sub-cell lines obtained by acclimating these cell lines to media in which they can grow, and the like.

The parent cell of a rat myeloma cell line YB2/3HL.P2.G11.16Ag.20 cell includes cell lines established from Y3/Ag.1.2.3 cell (ATCC CRL-1631) such as YB2/3HL.P2.G11.16Ag.20 cell described in literatures such as *J. Cell Biol.,* 93, 576 (1982) and *Methods Enzymol.,* 73B, 1 (1981), YB2/3HL.P2.G11.16Ag.20 cell (ATCC CRL-1662) registered at ATCC, sub-lines obtained by acclimating these cell lines to media in which they can grow, and the like.

The method for decreasing or deleting the activity of the GDP-fucose transport protein may be any technique, so long as it is a method for decreasing or deleting the activity of the GDP-fucose transport protein. However, genetic engineering techniques are preferred. Examples include:

(a) a gene disruption technique which comprises targeting a gene encoding the GDP-fucose transport protein, (b) a technique for introducing a dominant negative mutant of the GDP-fucose transport protein, (c) a technique for introducing mutation into the GDP-fucose transport protein, (d) a technique for suppressing transcription and/or translation of the GDP-fucose transport protein, and the like.

Furthermore, the cell of the present invention in which the GDP-fucose transport protein is more decreased or deleted than its parent cell can be obtained by using a method for selecting a clone resistant to a lectin which recognizes a sugar chain in which 1-position of fucose is bound to 6-position of N-acetylglucosamine in the reducing end through α-bond in the complex N-glycoside-linked sugar chain.

The lectin-resistant cell is a cell in which its growth is not inhibited in cell culturing when a lectin is applied to the culturing medium at an effective concentration.

In the present invention, the effective concentration in which the growth is not inhibited can be selected depending on the cell line, and is generally 10 μg/ml to 10.0 mg/ml, preferably 0.5 to 2.0 mg/ml. The effective concentration when mutation is introduced into the parent cell is a concentration in which the parent cell cannot normally grow or higher than the concentration, and is a concentration which is preferably similar to, more preferably 2 to 5 times, still more preferably at least 10 times, and most preferably at least 20 times, higher than the concentration in which the parent cell cannot normally grow.

As the lectin which recognizes a sugar chain structure in which 1-position of fucose is bound to 6-position of N-acetylglucosamine in the reducing end through α-bond in the N-glycoside-linked sugar chain, any lectin can be used, so long as it can recognize the sugar chain structure. Examples include a *Lens culinaris* lectin LCA (lentil agglutinin derived from *Lens culinaris*), a pea lectin PSA (pea lectin derived from *Pisum salivum*), a broad bean lectin VFA (agglutinin derived from *Vicia faba*), an *Aleuria aurantia* lectin AAL (lectin derived from *Aleuria aurantia*) and the like.

The GDP-fucose transport protein includes GDP-fucose transporter and the like. Also, a protein which has an influence on the activity or expression of the GDP-fucose transport protein is included in the GDP-fucose transport protein.

In the present invention, the GDP-fucose transporter includes a protein encoded by a DNA of the following (a) to (h):

(a) a DNA comprising the nucleotide sequence represented by SEQ ID NO:1;

(b) a DNA comprising the nucleotide sequence represented by SEQ ID NO:3;

(c) a DNA comprising the nucleotide sequence represented by SEQ ID NO:29;

(d) a DNA comprising the nucleotide sequence represented by SEQ ID NO:30;

(e) a DNA which hybridizes with the DNA comprising the nucleotide sequence represented by SEQ ID NO:1 under stringent conditions and encodes a protein having GDP-fucose transporter activity;

(f) a DNA which hybridizes with the DNA comprising the nucleotide sequence represented by SEQ ID NO:3 under stringent conditions and encodes a protein having GDP-fucose transporter activity;

(g) a DNA which hybridizes with the DNA comprising the nucleotide sequence represented by SEQ ID NO:29 under stringent conditions and encodes a protein having GDP-fucose transporter activity;

(h) a DNA which hybridizes with the DNA comprising the nucleotide sequence represented by SEQ ID NO:30 under stringent conditions and encodes a protein having GDP-fucose transporter activity.

Also, the GDP-fucose transporter of the present invention includes a protein selected from the group of the following (i) to (t):

(i) a protein comprising the amino acid sequence represented by SEQ ID NO:2;

(j) a protein comprising the amino acid sequence represented by SEQ ID NO:4;

(k) a protein comprising the amino acid sequence represented by SEQ ID NO:31;

(f) a protein comprising the amino acid sequence represented by SEQ ID NO:32;

(m) a protein which comprises an amino acid sequence in which at least one amino acid is deleted, substituted, inserted and/or added in the amino acid sequence represented by SEQ ID NO:2 and has GDP-fucose transporter activity, (n) a protein which comprises an amino acid sequence in which at least one amino acid is deleted, substituted, inserted and/or added in the amino acid sequence represented by SEQ ID NO:4 and has GDP-fucose transporter activity, (o) a protein which comprises an amino acid sequence in which at least one amino acid is deleted, substituted, inserted and/or added in the amino acid sequence represented by SEQ ID NO:31 and has GDP-fucose transporter activity, (p) a protein which comprises an amino acid sequence in which at least one amino acid is deleted, substituted, inserted and/or added in the amino acid sequence represented by SEQ ID NO:32 and has GDP-fucose transporter activity, (q) a protein which comprises an amino acid sequence having a homology of at least 80% with the amino acid sequence represented by SEQ ID NO:2 and has GDP-fucose transporter activity;

(r) a protein which comprises an amino acid sequence having a homology of at least 80% with the amino acid sequence represented by SEQ ID NO:4 and has GDP-fucose transporter activity;

(s) a protein which comprises an amino acid sequence having a homology of at least 80% with the amino acid sequence represented by SEQ ID NO:31 and has GDP-fucose transporter activity;

(t) a protein which comprises an amino acid sequence having a homology of at least 80% with the amino acid sequence represented by SEQ ID NO:32 and has GDP-fucose transporter activity.

In the present invention, a DNA which is hybridizable under stringent conditions is a DNA obtained, e.g., by a method such as colony hybridization, plaque hybridization or Southern blot hybridization using a DNA such as the DNA having the nucleotide sequence represented by SEQ ID NO:1, 3, 29 or 30 or a partial fragment thereof as the probe, and the examples of which includes a DNA which can be identified by carrying out hybridization at 65° C. in the presence of 0.7 to 1.0 M sodium chloride using a filter to which colony- or plaque-derived DNA fragments are immobilized, and then washing the filter at 65° C. using 0.1 to 2×SSC solution (composition of the 1×SSC solution comprising 150 mM sodium chloride and 15 mM sodium citrate). The hybridization can be carried out in accordance with the methods described, e.g., in *Molecular Cloning, A Laboratory Manual*, Second Edition, Cold Spring Harbor Laboratory Press (1989) (hereinafter referred to as "*Molecular Cloning*, Second Edition"), *Current Protocols in Molecular Biology*, John Wiley & Sons, 1987-1997 (hereinafter referred to as "*Current Protocols in Molecular Biology*"); *DNA Cloning I: Core Techniques, A Practical Approach*, Second Edition, Oxford University (1995), and the like. The hybridizable DNA include a DNA having at least 60% or more, preferably 70% or more, more preferably 80% or more, still more preferably 90% or more, far more preferably 95% or more, and most preferably 98% or more, of homology with the nucleotide sequence represented by SEQ A) NO:1, 3, 29 or 30.

In the present invention, the protein which comprises an amino acid sequence in which at least one amino acid is deleted, substituted, inserted and/or added in the amino acid sequence represented by SEQ ID NO:2, 4, 31 or 32 and has GDP-fucose transporter activity can be obtained, e.g., by introducing a site-directed mutation into a DNA encoding a protein having the amino acid sequence represented by SEQ ID NO:2, 4, 31 or 32, respectively, by using the method for introducing site-directed mutagenesis described, e.g., in *Molecular Cloning*, Second Edition; *Current Protocols in Molecular Biology; Nucleic Acids Research*, 10, 6487 (1982), *Proc. Natl. Acad. Sci., USA*, 79, 6409 (1982); *Gene*, 34, 315 (1985); *Nucleic Acids Research*, 13, 4431 (1985), *Proc. Natl. Acad. Sci. USA*, 82, 488 (1985); and the like. The number of amino acids to be deleted, substituted, inserted and/or added is one or more, and the number is not particularly limited, but is a number which can be deleted, substituted or added by a known technique such as the site-directed mutagenesis, e.g., it is 1 to several tens, preferably 1 to 20, more preferably 1 to 10, and most preferably 1 to 5.

As a protein having a homology of at least 80% with the amino acid sequence represented by SEQ ID NO:2, 4, 31 or 32 and having GDP-fucose transporter activity, mentioned are proteins having at least 80% or more, preferably 85% or more, more preferably 90% or more, still more preferably 95% or more, far more preferably 97% or more, and most preferably 99% or more, of homology with the amino acid sequence represented by SEQ ID NO:2, 4, 31 or 32 when calculated using an analyzing soft such as BLAST [*J. Mol. Biol.*, 215, 403 (1990)] or FASTA [*Methods in Enzymology*, 183, 63 (1990)], and also having GDP-fucose transporter activity.

The host cell of the present invention may be any cell, so long as it can express an antibody molecule. Examples include yeast, an animal cell, an insect cell, a plant cell and the like, and preferred is an animal cell. As an animal cell, preferred examples include a CHO cell derived from a Chinese hamster ovary tissue, a rat myeloma cell line YB2/3HL.P2.G11.16Ag.20 cell, a mouse myeloma cell line NS0 cell, a mouse myeloma SP2/0-Ag14 cell, a BHK cell derived from a syrian hamster kidney tissue, an antibody producing-hybridoma cell, a human leukemia cell line Namalwa cell, an embryonic stem cell, a fertilized egg cell and the like.

The antibody composition can be prepared by introducing a gene encoding an antibody molecule into the host cell of the present invention or by using the host cell when the host cell is capable of producing an antibody molecule.

Moreover, the present invention relates to a process for producing an antibody composition, which comprises using a non-human animal or plant or the progenies thereof in which genome is modified so as to decrease the activity of a protein relating to transport of an intracellular sugar nucleotide, GDP-fucose, to the Golgi body.

In the present invention, the antibody composition is a composition which comprises an antibody molecule having a complex N-glycoside-linked sugar chain in the Fc region.

The antibody is a tetramer in which two molecules of each of two polypeptide chains, a heavy chain and a light chain (hereinafter referred to as "H chain" and "L chain", respectively), are respectively associated. Each of about a quarter of the N-terminal side of the H chain and about a half of the N-terminal side of the L chain (more than 100 amino acids for each) is called variable region (hereinafter referred to as "V region") which is rich in diversity and directly relates to the binding with an antigen. The greater part of the moiety other than the V region is called constant region (hereinafter referred to as "C region"). Based on homology with the C region, antibody molecules are classified into classes IgG, IgM, IgA, IgD and IgE.

Also, the IgG class is further classified into subclasses IgG1 to IgG4 based on homology with the C region.

The H chain is divided into four immunoglobulin domains, VH, CH1, CH2 and CH3, from its N-terminal side, and a highly flexible peptide region called hinge region is present between CH1 and CH2 to divide CH1 and CH2. A structural unit comprising CH2 and CH3 under the downstream of the hinge region is called Fc region to which a complex N-glycoside-linked sugar chain is bound. Fc region is a region to which an Fc receptor, a complement and the like are bound (*Immunology Illustrated*, the Original, 5th edition, published on Feb. 10, 2000, by Nankodo; *Handbook of Antibody Technology* (*Kotai Kogaku Nyumon*), 1st edition on Jan. 25, 1994, by Chijin Shokan).

Sugar chains of glycoproteins such as an antibody are roughly divided into two types, namely a sugar chain which binds to asparagine (N-glycoside-linked sugar chain) and a sugar chain which binds to other amino acid such as serine, threonine (O-glycoside-linked sugar chain), based on the binding form to the protein moiety. The N-glycoside-linked sugar chains have a basic common core structure shown by the following structural formula (I) [*Biochemical Experimentation Method* 23—*Method for Studying Glycoprotein Sugar Chain* (Gakujutsu Shuppan Center), edited by Reiko Takahashi (1989)].

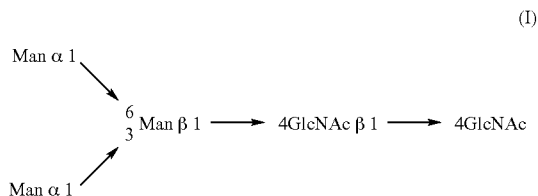

In formula (I), the sugar chain terminus which binds to asparagine is called a reducing end, and the opposite side is called a non-reducing end.

The N-glycoside-linked sugar chain may be any N-glycoside-linked sugar chain, so long as it comprises the core structure of formula (I). Examples include a high mannose type in which mannose alone binds to the non-reducing end of the core structure, a complex type in which the non-reducing end side of the core structure comprises at least one parallel branches of galactose-N-acetylglucosamine (hereinafter referred to as "Gal-GlcNAc") and the non-reducing end side of Gal-GlcNAc comprises a structure of sialic acid, bisecting N-acetylglucosamine or the like; a hybrid type in which the non-reducing end side of the core structure comprises branches of both of the high mannose type and complex type; and the like.

Since the Fc region in the antibody molecule comprises positions to which N-glycoside-linked sugar chains are separately bound, two sugar chains are bound per one antibody molecule. Since the NV-glycoside-linked sugar chain which binds to an antibody molecule includes any sugar chain having the core structure represented by formula (I), there are a number of combinations of sugar chains for the two N-glycoside-linked sugar chains which bind to the antibody.

Accordingly, the antibody composition of the present invention which is prepared by a cell in which the activity of the GDP-fucose transport protein is decreased or deleted may comprise an antibody having the same sugar chain structure or an antibody having different sugar chain structures, so long as the effect of the present invention is obtained from the composition. As the antibody composition of the present invention, preferred is an antibody composition in which, among the total complex N-glycoside-linked sugar chains bound to the Fc region in the antibody composition, the ratio of a sugar chain in which fucose is not bound to N-acetylglucosamine in the reducing end in the sugar chain is higher than that of an antibody composition produced by a parent cell which is not subjected to a treatment for decreasing or deleting the activity of the GDP-fucose transport protein.

Furthermore, the antibody composition of the present invention which is prepared by using a non-human animal or plant or the progenies thereof in which genome is modified so as to decrease the activity of the GDP-fucose transport protein may comprise an antibody having the same sugar chain structure or an antibody having different sugar chain structures, so long as the effect of the present invention is obtained from the composition. As the antibody composition of the present invention, preferred is an antibody composition in which, among the total complex N-glycoside-linked sugar chains bound to the Fc region in the antibody composition, the ratio of a sugar chain in which fucose is not bound to N-acetylglucosamine in the reducing end in the sugar chain is higher than that of an antibody composition prepared by using a non-human animal or plant or the progenies thereof (hereinafter referred to as "parent individual") in which genome is not modified.

In the present invention, the ratio of a sugar chain in which fucose is not bound to N-acetylglucosamine in the reducing end in the sugar chain among the total complex N-glycoside-linked sugar chains bound to the Fc region contained in the antibody composition is a ratio of the number of a sugar chain in which fucose is not bound to N-acetylglucosamine in the reducing end in the sugar chain to the total number of the complex N-glycoside-linked sugar chains bound to the Fc region contained in the composition.

The sugar chain in which fucose is not bound to N-acetylglucosamine in the reducing end in the complex N-glycoside-linked sugar chain is a sugar chain in which fucose is not bound to N-acetylglucosamine in the reducing end through α-bond in the complex N-glycoside-linked sugar chain. Specifically, it is a complex N-glycoside-linked sugar chain in which 1-position of fucose is not bound to 6-position of N-acetylglucosamine through α-bond.

The antibody composition having high ADCC toxicity includes those in which, among total complex N-glycoside-linked sugar chains bound to the Fc region in the antibody composition, the ratio of a sugar chain in which fucose is not bound to N-acetylglucosamine in the reducing end in the sugar chain is higher than the ratio in an antibody composition produced by the parent cell or parent individual. Examples include an antibody composition in which the activity is at least 2 times, preferably at least 3 times, more preferably at least 5 times, and still more preferably 10 times or higher. An antibody composition in which all of complex N-glycoside-linked sugar chains bound to the Fc region in the antibody composition are sugar chains in which fucose is not bound to N-acetylglucosamine in the reducing end in the sugar chain is most preferred.

According to the antibody composition of the present invention, when, among total complex N-glycoside-linked sugar chains bound to the Fc region, the ratio of a sugar chain in which fucose is not bound to N-acetylglucosamine in the reducing end in the sugar chain is higher than that in an antibody composition produced by the parent cell or parent individual, the antibody composition of the present invention has higher ADCC activity than the antibody composition comprising an antibody molecule produced by the parent cell or parent individual.

The ADCC activity is a cytotoxic activity in which an antibody bound to a cell surface antigen on a tumor cell in the living body activate an effector cell through an Fc receptor existing on the antibody Fc region and effector cell surface and thereby obstruct the tumor cell and the like [*Monoclonal Antibodies. Principles and Applications*, Wiley-Liss, Inc., Chapter 2.1 (1955)]. The effector cell includes a killer cell, a natural killer cell, an activated macrophage and the like.

The ratio of a sugar chain in which fucose is not bound to N-acetylglucosamine in the reducing end in the sugar chain contained in the composition which comprises an antibody molecule having complex N-glycoside-linked sugar chains in the Fc region can be determined by releasing the sugar chain from the antibody molecule by using a known method such as hydrazinolysis or enzyme digestion [*Biochemical Experimentation Methods* 23—*Method for Studying Glycoprotein Sugar Chain* (Japan Scientific Societies Press), edited by Reiko Takahashi (1989)], carrying out fluorescence labeling or radioisotope labeling of the released sugar chain and then separating the labeled sugar chain by chromatography. Also, the released sugar chain can also be determined by analyzing it with the HPAED-PAD method [*J. Liq Chromatogr.*, 6, 1557 (1983)].

The antibody molecule may be any antibody molecule, so long as it comprises the Fc region of an antibody. Examples include an antibody, an antibody fragment, a fusion protein comprising an Fc region, and the like.

The antibody includes an antibody secreted by a hybridoma cell, an antibody prepared by a genetic recombination technique, namely an antibody obtained by introducing an antibody gene-inserted antibody expression vector into a host cell, and the like. Examples include an antibody produced by a hybridoma, a humanized antibody, a human antibody and the like.

A hybridoma is a cell which is obtained by cell fusion between a B cell obtained by immunizing a non-human mammal with an antigen and a myeloma cell derived from mouse or the like and which can produce a monoclonal antibody having the antigen specificity of interest.

The humanized antibody includes a human chimeric antibody, a human CDR-grafted antibody and the like.

A human chimeric antibody is an antibody which comprises H chain V region (hereinafter referred to as "HV" or "VH") and L chain V region (hereinafter referred to as "LV" or "VL"), both of a non-human animal antibody, a human antibody H chain C region (hereinafter also referred to as "CH") and a human antibody L chain C region (hereinafter also referred to as "CL"). The non-human animal may be any animal such as mouse, rat, hamster or rabbit, so long as a hybridoma can be prepared therefrom.

The human chimeric antibody can be produced by obtaining cDNAs encoding VH and VL from a monoclonal antibody-producing hybridoma, inserting them into an expression vector for host cell having genes encoding human antibody CH and human antibody CL to thereby construct a human chimeric antibody expression vector, and then introducing the vector into a host cell to express the antibody.

As the CH of human chimeric antibody, any CH can be used, so long as it belongs to human immunoglobulin (hereinafter referred to as "hIg") can be used, and those belonging to the hIgG class are preferred, and any one of the subclasses belonging to the hIgG class, such as hIgG1, hIgG2, hIgG3 and hIgG4, can be used. As the CL of human chimeric antibody, any CL can be used, so long as it belongs to the hIg class, and those belonging to the κ class or λ class can be used.

The human CDR-grafted antibody can be produced by constructing cDNAs encoding V regions in which CDRs of VH and VL of a non-human animal antibody are grafted into CDRs of VH and VL of a human antibody, inserting them into an expression vector for host cell having genes encoding human antibody CH and human antibody CL to thereby construct a human CDR-grafted antibody expression vector, and then introducing the expression vector into a host cell to express the human CDR-grafted antibody.

As the CH of human CDR-grafted antibody, any CH can be used, so long as it belongs to the hIg, and those of the hIgG class are preferred and any one of the subclasses belonging to the hIgG class, such as hIgG1, hIgG2, hIgG3 and hIgG4, can be used. As the CL of human CDR-grafted antibody, any CL can be used, so long as it belongs to the hIg class, and those belonging to the κ class or λ class can be used.

A human antibody is originally an antibody naturally existing in the human body, but it also includes antibodies obtained from a human antibody phage library, a human antibody-producing transgenic non-transgenic animal and a human antibody-producing transgenic plant, which are prepared based on the recent advance in genetic engineering, cell engineering and developmental engineering techniques.

A human antibody is originally an antibody naturally existing in the human body, but it also includes antibodies obtained from a human antibody phage library, a human antibody-producing transgenic animal and a human antibody-producing transgenic plant, which are prepared based on the recent advance in genetic engineering, cell engineering and developmental engineering techniques.

The antibody existing in the human body can be prepared by isolating a human peripheral blood lymphocyte, immortalizing it by its infection with EB virus or the like and then cloning it to thereby obtain lymphocytes capable of producing the antibody, culturing the lymphocytes thus obtained, and collecting the antibody from the culture.

The human antibody phage library is a library in which antibody fragments such as Fab and single chain antibody are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the marker. The antibody fragment can be converted further into a human antibody molecule comprising two full H chains and two full L chains by genetic engineering techniques.

A human antibody-producing transgenic non-human animal is an animal in which a human antibody gene is introduced into cells. Specifically, a human antibody-producing transgenic non-human animal can be prepared by introducing a human antibody gene into ES cell of a mouse, transplanting the ES cell into an early stage embryo of other mouse and then developing it. By introducing a human chimeric antibody gene into a fertilized egg and developing it, the transgenic non-human animal can be also prepared. A human antibody is prepared from the human antibody-producing transgenic non-human animal by obtaining a human antibody-producing hybridoma by a hybridoma preparation method usually carried out in non-human mammals, culturing the obtained hybridoma and accumulating the human antibody in the culture.

The transgenic non-human animal includes cattle, sheep, goat, pig, horse, mouse, rat, fowl, monkey, rabbit and the like.

In the present invention, as the antibody, preferred are an antibody which recognizes a tumor-related antigen, an antibody which recognizes an allergy- or inflammation-related antigen, an antibody which recognizes cardiovascular disease-related antigen, an antibody which recognizes an autoimmune disease-related antigen or an antibody which recognizes a viral or bacterial infection-related antigen, and a human antibody which belongs to the IgG class is preferred.

An antibody fragment is a fragment which comprises at least a part of the Fc region of an antibody. The Fc region is a region at the C-terminal of H chain of an antibody, CH2 region and CH3 region, and includes a natural type and a mutant type. "A part of the Fc region" is preferably a fragment containing CH2 region, more preferably a region containing Asp at position 1 in CH2 region. The Fc region of the IgG class is from Cys at position 226 to the C-terminal or from Pro at position 230 to the C-terminal according to the numbering of EU Index of Kabat et al [*Sequences of Proteins of Immunological Interest*, 5$^{th}$ Ed., Public Health Service, National Institutes of Health, Bethesda, Md. (1991)]. The antibody fragment includes an H chain monomer, an H chain dimer and the like.

A fusion protein comprising a part of an Fc region is a protein which is obtained by fusing an antibody comprising the Fc region of an antibody or the antibody fragment with a protein such as an enzyme or a cytokine (hereinafter referred to as "Fc fusion protein").

The present invention is explained below in detail.

1. Preparation of Host Cell of the Present Invention

The host cell of the present invention can be prepared by the following techniques.

(1) Gene Disruption Technique which Comprises Targeting Gene Encoding GDP-Fucose Transport Protein The host cell of the present invention can be prepared according to a gene disruption technique which comprises targeting a gene encoding the GDP-fucose transport protein. The GDP-fucose transport protein includes GDP-fucose transporter and the like.

The gene as used herein includes DNA and RNA.

The gene disruption method may be any method, so long as it can disrupt the gene of the target enzyme is included. Examples include a homologous recombination method, an RNA-DNA oligonucleotide (RDO) method, a method using retrovirus, a method using transposon, an antisense method, a ribozyme method, an RNA interference (RNAi) method and the like.

(a) Preparation of Cell of the Present Invention by Antisense Method or Ribozyme Method The host cell of the present invention can be prepared by targeting a gene encoding the GDP-fucose transport protein according to the ribozyme method described in *Cell Technology*, 12, 239 (1993); *BIO/TECHNOLOGY*, 17, 1097 (1999); *Hum. Mol Genet.*, 5, 1083 (1995); *Cell Technology*, 13, 255 (1994), *Proc. Natl. Acad. Sci. USA*, 96, 1886 (1999); or the like, for example, as follows.

A cDNA or a genomic DNA encoding the GDP-fucose transport protein is prepared.

The nucleotide sequence of the prepared cDNA or genomic DNA is determined.

The genomic DNA encoding the GDP-fucose transport protein includes a genomic DNA encoding a GDP-fucose transporter comprising the nucleotide sequence represented by SEQ ID NO:34 or 35.

Based on the determined DNA sequence, an antisense gene or ribozyme construct of an appropriate length comprising a part of DNA which encodes the GDP-fucose transporter protein, a part of its untranslated region or a part of its intron, is designed.

In order to express the antisense gene or ribozyme in a cell, a recombinant vector is prepared by inserting a fragment or total length of the prepared DNA into downstream of the promoter of an appropriate expression vector.

A transformant is obtained by introducing the recombinant vector into a host cell suitable for the expression vector.

The host cell can be obtained by selecting a transformant based on the activity of the GDP-fucose transporter protein. The host cell of the present invention can also be obtained by selecting a transformant based on the sugar chain structure of a glycoprotein on the cell membrane or the sugar chain structure of the produced antibody molecule.

As the host cell used for preparing the host cell of the present invention, any cell such as yeast, an animal cell, an insect cell or a plant cell can be used, so long as it has a gene encoding the target GDP-fucose transporter protein. Examples include host cells described in the following item 3.

As the expression vector, a vector which is autonomously replicable in the host cell or can be integrated into the chromosome and comprises a promoter at such a position that the designed antisense gene or ribozyme can be transferred is used. Examples include expression vectors described in the following item 3.

As the method for introducing a gene into various host cells, the methods for introducing recombinant vectors suitable for various host cells described in the following item 3 can be used.

As a method for obtaining a cDNA or genomic DNA of the GDP-fucose transporter protein, the following method is exemplified.

Preparation Method of cDNA:

A total RNA or mRNA is prepared from various host cells.
A cDNA library is prepared from the prepared total RNA or mRNA.

Degenerative primers are produced based on a known amino acid sequence, such as a human sequence, of the GDP-fucose transport protein, and a gene fragment encoding the GDP-fucose transport protein is obtained by PCR using the prepared cDNA library as the template.

A cDNA of the GDP-fucose transport protein can be obtained by screening the cDNA library using the obtained gene fragment as a probe.

The mRNA of various host cells may be a commercially available product (e.g., manufactured by Clontech) or may be prepared from various host cells as follows. The method for preparing total mRNA from various host cells include the guanidine thiocyanate-cesium trifluoroacetate method [*Methods in Enzymology*, 154, 3 (1987)], the acidic guanidine thiocyanate phenol chloroform (AGPC) method [*Analytical Biochemistry*, 162, 156 (1987); *Experimental Medicine* (*Jikken Igaku*), 9, 1937 (1991)] and the like.

Furthermore, a method for preparing mRNA as poly(A)+ RNA from a total RNA includes the oligo(dT)-immobilized cellulose column method (*Molecular Cloning. Second Edition*)

In addition, mRNA can be prepared using a kit such as Fast Track mRNA Isolation Kit (manufactured by Invitrogen) or Quick Prep mRNA Purification Kit (manufactured by Pharmacia).

A cDNA library is prepared from the prepared mRNA of various host cells. The method for preparing cDNA libraries includes the methods described in *Molecular Cloning*, Second Edition, *Current Protocols in Molecular Biology*, and the like, or methods using commercially available kits such as SuperScript Plasmid System for cDNA Synthesis and Plasmid Cloning (manufactured by Life Technologies) and ZAP-cDNA Synthesis Kit (manufactured by STRATAGENE).

As the cloning vector for preparing the cDNA library, any vector such as a phage vector or a plasmid vector can be used, so long as it is autonomously replicable in *Escherichia coli* K12. Examples include ZAP Express [manufactured by STRATAGENE, *Strategies*, 5, 58 (1992)], pBluescript II SK(+) [*Nucleic Acids Research*, 17, 9494 (1989)], Lambda ZAP II (manufactured by STRATAGENE), λgt10 and λgt11 [*DNA Cloning, A Practical Approach*, 1, 49 (1985)], λTriplEx (manufactured by Clontech), λExCell (manufactured by Pharmacia), pcD2 [*Mol. Cell. Biol.*, 3, 280 (1983)], pUC18 [*Gene*, 33, 103 (1985)] and the like.

Any microorganism can be used as the host microorganism for preparing the cDNA library, and *Escherichia coli* is preferably used. Examples include *Escherichia coli* XL1-Blue MRF' [manufactured by STRATAGENE, *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)] and the like The cDNA library can be used as such in the subsequent analysis, and in order to obtain a full length cDNA as efficient as possible by decreasing the ratio of an infull length cDNA, a cDNA library prepared according to the oligo cap method developed by Sugano et al. [*Gene*, 138, 171 (1994); *Gene*, 200, 149 (1997); *Protein, Nucleic Acid, Protein* (*Tanpakushitu, Kakusan, Koso*), 41, 603 (1996), *Experimental Medicine* (*Jikken Igaku*), 11, 2491 (1993); *cDNA Cloning* (Yodosha) (1996); *Methods for Preparing Gene Libraries* (Yodosha) (1994)] can be used in the following analysis.

Based on the amino acid sequence of the GDP-fucose transport protein, degenerative primers specific for the 5'-terminal and 3'-terminal nucleotide sequences of a nucleotide sequence presumed to encode the amino acid sequence are prepared, and DNA is amplified by PCR [*PCR Protocols*, Academic Press (1990)] using the prepared cDNA library as the template to obtain a gene fragment encoding the GDP-fucose transport protein.

It can be confirmed that the obtained gene fragment is a DNA encoding the GDP-fucose transport protein by a method generally used for analyzing a nucleotide such as the dideoxy method of Sanger et al. [*Proc. Natl. Acad. Sci. USA*, 74, 5463 (1977)] or a nucleotide sequence analyzer such as ABI-PRISM 377 DNA Sequencer (manufactured by PE Biosystems).

A DNA encoding the GDP-fucose transport protein can be obtained by carrying out colony hybridization or plaque hybridization (*Molecular Cloning*, Second Edition) for the cDNA or cDNA library synthesized from the mRNA contained in various host cells, using the gene fragment as a DNA probe.

Also, a DNA encoding the GDP-fucose transport protein can also be obtained by carrying out screening by PCR using the cDNA or cDNA library synthesized from the mRNA contained in various host cells as the template and using the primers used for obtaining the gene fragment encoding the GDP-fucose transport protein.

The nucleotide sequence of the obtained DNA encoding the GDP-fucose transport protein is analyzed from its terminus and determined by a method generally used for analyzing a nucleotide such as the dideoxy method of Sanger et al. [*Proc Natl. Acad. Sci. USA*, 74, 5463 (1977)] or a nucleotide sequence analyzer such as ABIPRISM 377 DNA Sequencer (manufactured by PE Biosystems).

A gene encoding the GDP-fucose transport protein can also be determined from genes in data bases by searching nucleotide sequence data bases such as GenBank, EMBL and DDBJ using a homology retrieving program such as BLAST based on the determined cDNA nucleotide sequence.

The nucleotide sequence of a gene encoding the GDP-fucose transport protein obtained by the above method includes the nucleotide sequence represented by SEQ ID NO:1, 3, 29 or 30.

The cDNA of the GDP-fucose transport protein can also be obtained by chemically synthesizing it with a DNA synthesizer such as DNA Synthesizer model 392 manufactured by Perkin Elmer using the phosphoamidite method, based on the determined DNA nucleotide sequence.

As an example of the method for preparing a genomic DNA of the GDP-fucose transport protein, the method described below is exemplified.

Preparation Method of Genomic DNA:

The method for preparing genomic DNA includes known methods described in *Molecular Cloning*, Second Edition; *Current Protocols in Molecular Biology*; and the like. In addition, a genomic DNA of the GDP-fucose transport protein can also be isolated using a kit such as Genome DNA Library Screening System (manufactured by Genome Systems) or Universal GenomeWalker™ Kits (manufactured by CLONTECH).

The following method can be exemplified as the method for selecting a transformant based on the activity of the GDP-fucose transport protein.

Method for Selecting Transformant:

The method for selecting a cell in which the activity of the GDP-fucose transport protein is decreased or deleted includes biochemical methods or genetic engineering techniques described in *New Biochemical Experimentation Series 3-Saccharides I, Glycoprotein* (Tokyo Kagaku Dojin), edited by Japanese Biochemical society (1988); *Cell Engineering, Supplement, Experimental Protocol Series, Glycobiology Experimental Protocol, Glycoprotein, Glycolipid and Proteoglycan* (Shujun-sha), edited by Naoyuki Taniguchi, Akemni Suzuki, Kiyoshi Furukawa and Kazuyuki Sugawara (1996); *Molecular Cloning*, Second Edition, *Current Protocols in Molecular Biology*; and the like. The biochemical method includes a method in which the transport activity to the Golgi body is evaluated using GDP-fucose as a substrate. The genetic engineering techniques include the Northern analysis, RT-PCR and the like which measures the amount of mRNA of a gene encoding the GDP-fucose transport protein.

Furthermore, the method for selecting a cell based on morphological change caused by decrease or deletion of the activity of the GDP-fucose transport includes a method for selecting a transformant based on the sugar structure of a produced antibody molecule, a method for selecting a transformant based on the sugar structure of a glycoprotein on a cell membrane, and the like. The method for selecting a transformant using the sugar structure of an antibody-producing molecule includes method described in the item 5 below. The method for selecting a transformant using the sugar structure of a glycoprotein on a cell membrane a clone resistant to a lectin which recognizes a sugar chain structure wherein 1-position of fucose is bound to 6-position of N-acetylglucosamine in the reducing end through α-bond in the complex N-glycoside-linked sugar chain. Examples include a method using a lectin described in *Somatic Cell Mol. Genet.*, 12, 51 (1986).

As the lectin, any lectin can be used, so long as it is a lectin which recognizes a sugar chain structure in which 1-position of fucose is bound to 6-position of N-acetylglucosamine in the reducing end through α-bond in the N-glycoside-linked sugar chain. Examples include a *Lens culinaris* lectin LCA (lentil agglutinin derived from *Lens culinaris*), a pea lectin PSA (pea lectin derived from *Pisum sativum*), a broad bean lectin VFA (agglutinin derived from *Vicia faba*), an *Aleuria aurantia* lectin AAL (lectin derived from *Aleuria aurantia*) and the like.

Specifically, the host cell of the present invention can be selected by culturing cells for 1 day to 2 weeks, preferably from 1 day to 1 week, in a medium comprising the lectin at a concentration of 10 μg/ml to 10 mg/ml, preferably 0.5 to 2.0 mg/ml, subculturing surviving cells or picking up a colony and transferring it into a culture vessel, and subsequently continuing the culturing in the lectin-containing medium.

In addition, the host cell of the present invention can also be obtained without using an expression vector, by directly introducing an antisense oligonucleotide or ribozyme which is designed based on the nucleotide sequence of the GDP-fucose transport protein into a host cell.

The antisense oligonucleotide or ribozyme can be prepared in the usual method or by using a DNA synthesizer. Specifically, it can be prepared based on the sequence information of an oligonucleotide having a corresponding sequence of continued 5 to 150 bases, preferably 5 to 60 bases, and more preferably 10 to 40 bases, among nucleotide sequences of a cDNA and a genomic DNA of a GDP-fucose transport protein by synthesizing an oligonucleotide which corresponds to a sequence complementary to the oligonucleotide (antisense oligonucleotide) or a ribozyme comprising the oligonucleotide sequence.

The oligonucleotide includes oligo RNA and derivatives of the oligonucleotide (hereinafter referred to as "oligonucleotide derivatives").

The oligonucleotide derivatives includes oligonucleotide derivatives in which a phosphodiester bond in the oligonucleotide is converted into a phosphorothioate bond, an oligonucleotide derivative in which a phosphodiester bond in the oligonucleotide is converted into an N3'-P5' phosphoamidate bond, an oligonucleotide derivative in which ribose and a phosphodiester bond in the oligonucleotide are converted into a peptide-nucleic acid bond, an oligonucleotide derivative in which uracil in the oligonucleotide is substituted with C-5 propynyluracil, an oligonucleotide derivative in which uracil in the oligonucleotide is substituted with C-5 thiazoleuracil, an oligonucleotide derivative in which cytosine in the oligonucleotide is substituted with C-5 propynylcytosine, an oligonucleotide derivative in which cytosine in the oligonucleotide is substituted with phenoxazine-modified cytosine, an oligonucleotide derivative in which ribose in the oligonucleotide is substituted with 2'-O-propylribose and an oligonucleotide derivative in which ribose in the oligonucleotide is substituted with 2'-methoxyethoxyribose [*Cell Technology (Saibo Kogaku)*, 16, 1463 (1997)].

(b) Preparation of Host Cell of the Present Invention by Homologous Recombination The host cell of the present invention can be produced by targeting a gene encoding the GDP-fucose transport protein and modifying the target gene on chromosome through a homologous recombination technique.

The target gene on the chromosome can be modified by using a method described in *Manipulating the Mouse Embryo, A Laboratory Manual*, Second Edition, Cold Spring Harbor Laboratory Press (1994) (hereinafter referred to as "*Manipulating the Mouse Embryo, A Laboratory Manual*") *Gene Targeting, A Practical Approach*, IRL Press at Oxford University Press (1993); *Biomanual Series 8, Gene Targeting, Preparation of Mutant Mice using ES*, Yodo-sha (1995) (hereinafter referred to as "*Preparation of Mutant Mice using ES Cells*"); or the like, for example, as follows.

A genomic DNA of the GDP-fucose transport protein is prepared.

Based on the nucleotide sequence of the genomic DNA, a target vector is prepared for homologous recombination of a target gene to be modified (e.g., structural gene of the GDP-fucose transport protein or a promoter gene).

The host cell can be produced by introducing the prepared target vector into a host cell and selecting a cell in which homologous recombination occurred between the target gene and target vector.

As the host cell, any cell such as yeast, an animal cell, an insect cell or a plant cell can be used, so long as it has a gene encoding the GDP-fucose transport protein. Examples include the host cells described in the following item 3.

The method for preparing a genomic DNA encoding the GDP-fucose transport protein includes the methods described in "Preparation method of genomic DNA" in the item 1(1)(a) and the like.

The target vector for the homologous recombination of the target gene can be prepared in accordance with a method described in *Gene Targeting, A Practical Approach*, IRL Press at Oxford University Press (1993); *Preparation of Mutant Mice using ES Cells*; or the like. The target vector can be used as either a replacement type or an insertion type.

For introducing the target vector into various host cells, the methods for introducing recombinant vectors suitable for various host cells described in the following item 3 can be used.

The method for efficiently selecting a homologous recombinant includes a method such as the positive selection, promoter selection, negative selection or polyA selection described in *Gene Targeting, A Practical Approach*, IRL Press at Oxford University Press (1993), *Preparation of Mutant Mice using ES Cells*; or the like. The method for selecting the homologous recombinant of interest from the selected clones includes the Southern hybridization method for genomic DNA (*Molecular Cloning*, Second Edition), PCR [*PCR Protocols*, Academic Press (1990)], and the like.

(c) Preparation of Host Cell of the Present Invention by RDO Method

The host cell of the present invention can be prepared by targeting a gene encoding the GDP-fucose transport protein according to an RDO (RNA-DNA oligonucleotide) method, for example, as follows.

A cDNA or a genomic DNA of the GDP-fucose transport protein is prepared.

The nucleotide sequence of the prepared cDNA or genomic DNA is determined.

Based on the determined DNA sequence, an RDO construct of an appropriate length comprising a part encoding the GDP-fucose transport protein, a part of its non-translation region or a part of an intron, is designed and synthesized.

The host cell of the present invention can be obtained by introducing the synthesized RDO into a host cell and then selecting a transformant in which a mutation occurred in the target GDP-fucose transport protein.

As the host cell, any cell such as yeast, an animal cell, an insect cell or a plant cell can be used, so long as it has a gene encoding the target GDP-fucose transport protein. Examples include the host cells described in the following item 3.

The method for introducing RDO into various host cells includes the methods for introducing recombinant vectors suitable for various host cells, described in the following item 3.

The method for preparing cDNA of the GDP-fucose transport protein includes the methods described in "Preparation method of cDNA" in the item 1(1)(a) and the like.

The method for preparing a genomic DNA of the GDP-fucose transport protein includes the methods in "Preparation method of genomic DNA" described in the item 1(1)(a) and the like.

The nucleotide sequence of the DNA can be determined by digesting it with appropriate restriction enzymes, cloning the fragments into a plasmid such as pBluescript SK(−) (manufactured by Stratagene), subjecting the clones to the reaction generally used as a method for analyzing a nucleotide sequence such as the dideoxy method of Sanger et al. [*Proc. Natl. Acad. Sci. USA*, 74, 5463 (1977)] or the like, and then analyzing the clones using an automatic nucleotide sequence analyzer such as A.L.F. DNA Sequencer (manufactured by Pharmacia) or the like.

The RDO can be prepared in the usual method or by using a DNA synthesizer.

The method for selecting a cell in which a mutation occurred, by introducing the RDO into the host cell, in the gene encoding the GDP-fucose transport protein includes the methods for directly detecting mutations in chromosomal genes described in *Molecular Cloning*, Second Edition, *Current Protocols in Molecular Biology* and the like.

Furthermore, the method described in the item 1(1)(a) for selecting a transformant through the evaluation of the activity of the introduced GDP-fucose transport protein, the method for selecting a transformant based on the sugar chain structure of a glycoprotein on the cell membrane, and the method for selecting a transformant based on the sugar structure of a produced antibody molecule described in the following item 5 can also be used.

The construct of the RDO can be designed in accordance with the methods described in *Science*, 273, 1386 (1996); *Nature Medicine*, 4, 285 (1998); *Hepatology*, 25, 1462 (1997); *Gene Therapy*, 5, 1960 (1999); *J. Mol. Med.*, 75, 829 (1997), *Proc. Natl. Acad. Sci. USA*, 96, 8774 (1999); *Proc. Natl. Acad. Sci. USA*, 96, 8768 (1999); *Nuc. Acids. Res.*, 27, 1323 (1999); *Invest. Dematol.*, 111, 1172 (1998); *Nature Biotech.*, 16, 1343 (1998); *Nature Biotech.*, 18, 43 (2000), *Nature Biotech.*, 18, 555 (2000); and the like.

(d) Preparation of Host Cell of the Present Invention by RNAi Method

The host cell of the present invention can be prepared by targeting a gene encoding the GDP-fucose transport protein according to the RNAi (RNA interference) method, for example, as follows.

A cDNA of the GDP-fucose transport protein is prepared.

The nucleotide sequence of the prepared cDNA is determined.

Based on the determined DNA sequence, an RNAi gene construct of an appropriate length comprising the DNA coding moiety encoding the GDP-fucose transport protein or a part of its untranslated region, is designed.

In order to express the RNAi gene in a cell, a recombinant vector is prepared by inserting a fragment or full length of the prepared DNA into downstream of the promoter of an appropriate expression vector.

A transformant is obtained by introducing the recombinant vector into a host cell suitable for the expression vector.

The host cell can be obtained by selecting a transformant based on the activity of the GDP-fucose transport protein, or the sugar chain structure of the produced antibody molecule or of a glycoprotein on the cell membrane.

As the host cell, any cell such as yeast, an animal cell, an insect cell or a plant cell can be used, so long as it has a gene encoding the target of the produced antibody molecule. Examples include the host cells described in the following item 3.

As the expression vector, a vector which is autonomously replicable in the host cell or can be integrated into the chromosome and comprises a promoter at such a position that the designed RNAi gene can be transferred is used. Examples include the expression vectors transcribed by polymerase III described in the following item 3.

As the method for introducing a gene into various host cells, the methods for introducing recombinant vectors suitable for various host cells described in the following item 3 can be used.

The method for selecting a transformant based on the activity of the of the produced antibody molecule or the method for selecting a transformant based on the sugar chain structure of a glycoprotein on the cell membrane as a marker includes the methods described in the item 1(1)(a). The method for selecting a transformant based on the sugar chain structure of a produced antibody molecule includes the methods described in the following item 5.

The method for preparing cDNA of the GDP-fucose transport protein includes the methods described in "Preparation method of cDNA" in the item 1(1)(a) and the like.

In addition, the host cell of the present invention can also be obtained without using an expression vector, by directly introducing an RNAi gene designed based on the nucleotide sequence of the GDP-fucose transport protein.

The RNAi gene can be prepared in the usual method or by using a DNA synthesizer.

The RNAi gene construct can be designed in accordance with the methods described in *Nature*, 391, 806 (1998); *Proc. Natl. Acad. Sci. USA*, 95, 15502 (1998); *Nature*, 395, 854 (1998); *Proc. Natl. Acad. Sci. USA*, 96, 5049 (1999); *Cell*, 95, 1017 (1998); *Proc. Natl. Acad. Sci. USA*, 96, 1451 (1999); *Proc. Natl. Acad. Sci. USA*, 95, 13959 (1998); *Nature Cell Biol.*, 2, 70 (2000); and the like.

The RNA used in the RNAi method of the present invention includes RNA corresponding to DNA encoding the GDP-fucose transport protein or the like. Preferred examples include RNA corresponding to DNA encoding the above-described GDP-fucose transporter.

The RNA used in the RNAi method of the present invention may be any double stranded RNA consisting of RNA and its complementary RNA and capable of decreasing the amount of mRNA of the GDP-fucose transport protein such as GDP-fucose transporter. Regarding the length of the RNA, the RNA is a continuous RNA of preferably 1 to 30, more preferably 5 to 29, still more preferably 10 to 29, and most preferably 15 to 29. Examples include:

(a) an RNA corresponding to DNA comprising the nucleotide sequence represented by 10 to 30 continuous nucleotides in the nucleotide sequence represented by SEQ ID NO:1;

(b) an RNA corresponding to DNA comprising the nucleotide sequence represented by 10 to 30 continuous nucleotides in the nucleotide sequence represented by SEQ ID NO:3;

(c) an RNA corresponding to DNA comprising the nucleotide sequence represented by 10 to 30 continuous nucleotides in the nucleotide sequence represented by SEQ ID NO:29 and (d) an RNA corresponding to DNA comprising the nucleotide sequence represented by 10 to 30 continuous nucleotides in the nucleotide sequence represented by SEQ ID NO:30. Preferable examples include:

(a) an RNA comprising the nucleotide sequence represented by SEQ ID NO:33; and (b) an RNA which comprises a nucleotide sequence in which one or a few nucleotides are deleted or added in the nucleotide sequence represented by SEQ ID NO:33 and has substantially the same RNAi activity as the RNA represented by SEQ ID NO:33.

The above RNA having substantially the same RNAi activity as the RNA represented by SEQ ID NO:33 may be any RNA having RNAi activity to the GDP-fucose transport protein as the RNA represented by SEQ ID NO:33, and the quantitative element such as the length of the RNA may be different.

The nucleotide sequence in which one or a few nucleotides are deleted or added means a nucleotide sequence in which one or a few nucleotides are deleted and/or added at both terminals of SEQ ID NO:33. Regarding the length of the nucleotide sequence, the nucleotide sequence is a continuous RNA of preferably 1 to 30, more preferably 5 to 29, still more preferably 10 to 29, and most preferably 15 to 29.

Furthermore, a DNA corresponding to the RNA and its complementary DNA are within the scope of the present invention, and the DNA corresponding to the RNA includes a DNA comprising the nucleotide sequence represented by SEQ ID NO:16. Moreover, a recombinant DNA comprising a vector into the DNA and its complementary DNA are introduced and a transformant obtained by introducing the recombinant DNA into a cell are also within the scope of the present invention, and can be used for expressing the double stranded RNA.

(e) Preparation of Host Cell of the Present Invention by Method Using Transposon The host cell of the present invention can be prepared by selecting a mutant based on the activity of the GDP-fucose transport protein or the sugar chain structure of a produced antibody molecule or of a glycoprotein on the cell membrane by using a transposon system described in *Nature Genet.*, 25, 35 (2000) or the like.

The transposon system is a system in which a mutation is induced by randomly inserting an exogenous gene into chromosome, wherein an exogenous gene interposed between transposons is generally used as a vector for inducing a mutation, and a transposase expression vector for randomly inserting the gene into chromosome is introduced into the cell at the same time.

Any transposase can be used, so long as it is suitable for the sequence of the transposon to be used.

As the exogenous gene, any gene can be used, so long as it can induce a mutation in the DNA of a host cell.

As the host cell, any cell such as yeast, an animal cell, an insect cell or a plant cell can be used, so long as it has a gene encoding the GDP-fucose transport protein. Examples include the host cells described in the following item 3. For introducing the gene into various host cells, the method for introducing recombinant vectors suitable for various host cells described in the following item 3 can be used.

The method for selecting a mutant based on the activity of the GDP-fucose transport protein or the method for selecting a mutant based on the sugar chain structure of a glycoprotein on the cell membrane includes the methods which will be described above in the item 1(1)(a). The method for selecting a mutant based on the sugar chain structure of a produced antibody molecule includes the methods described in the following item 5.

(2) Method for Introducing Dominant Negative Mutant of the GDP-Fucose Transport Protein The host cell of the present invention can be prepared by targeting a gene encoding the GDP-fucose transport protein according to a technique for introducing a dominant negative mutant of the protein. The GDP-fucose transport protein includes GDP-fucose transporter and the like.

It is known that a transporter of an intracellular sugar nucleotide functions in the form of a dimer on the membrane of endoplasmic reticulum or the Golgi body [*J. Biol. Chem.*, 275, 17718 (2000)]. Also, it is reported that, when a mutant of a transporter of an intracellular sugar nucleotide is compulsorily expressed intracellularly, a heterodimer is formed with a wild type transporter, and the formed heterodimer has an activity to inhibit a wild type homodimer [*J. Biol. Chem.*, 275, 17718 (2000)]. Accordingly, a mutant of a transporter of an intracellular sugar nucleotide is prepared and introduced into a cell so that it can function as a dominant negative mutant. The mutant can be prepared using the method for introducing site-directed mutagenesis described in *Molecular Cloning*, Second Edition, *Current Protocols in Molecular Biology* and the like.

The dominant negative mutant of the GDP-fucose transport protein includes an N-terminal-deleted mutant of a protein relating to transport of an intracellular sugar nucleotide, GDP-fucose, to the Golgi body, and is preferably an N-terminal-deleted mutant in which 30 amino acids of the N-terminal are deleted in a protein relating to transport of an intracellular sugar nucleotide, GDP-fucose, to the Golgi body. Specific examples include an N-terminal-deleted mutant of the GDP-fucose transporter described in Example 1.

The host cell of the present invention can be prepared by using the prepared dominant negative mutant gene of the target enzyme according to the method described in *Molecular Cloning*, Second Edition, *Current Protocols in Molecular Biology*, *Manipulating the Mouse Embryo*, Second Edition or the like, for example, as follows.

A dominant negative mutant gene of the GDP-fucose transport protein is prepared.

Based on the prepared full length DNA of dominant negative mutant gene, a DNA fragment of an appropriate length containing a part encoding the protein is prepared, if necessary.

A recombinant vector is prepared by inserting the DNA fragment or full length DNA into downstream of the promoter of an appropriate expression vector.

A transformant is obtained by introducing the recombinant vector into a host cell suitable for the expression vector.

The host cell can be prepared by selecting a transformant based on the activity of the GDP-fucose transport protein, or the sugar chain structure of a produced antibody molecule or of a glycoprotein on the cell membrane as a marker.

As the host cell, any cell such as yeast, an animal cell, an insect cell or a plant cell can be used, so long as it has a gene encoding the GDP-fucose transport protein. Examples include the host cells described in the following item 3.

As the expression vector, a vector which is autonomously replicable in the host cell or can be integrated into the chromosome and comprises a promoter at a position where transcription of the DNA encoding the dominant negative mutant of interest can be effected is used. Examples include the expression vectors described in the following item 3.

For introducing the gene into various host cells, the method for introducing recombinant vectors suitable for various host cells described in the following item 3 can be used.

The method for selecting a mutant based on the activity of the GDP-fucose transport protein or the method for selecting a mutant based on the sugar chain structure of a glycoprotein on the cell membrane includes the methods which will be described in the above item 1(1)(a). The method for selecting a mutant based on the sugar chain structure of a produced antibody molecule includes the methods described in the following item 5.

(3) Method for Introducing Mutation into GDP-Fucose Transport Protein

The host cell of the present invention can be prepared by introducing a mutation into a gene encoding the GDP-fucose transport protein, and then selecting a clone of interest in which the mutation occurred in the protein.

The gene encoding the GDP-fucose transport protein includes GDP-fucose transporter and the like.

Examples include 1) a method in which a desired clone is selected from mutants obtained by a mutation-inducing treatment of a parent cell line with a mutagen or spontaneously generated mutants, based on the activity of the GDP-fucose transport protein, 2) a method in which a desired clone is selected from mutants obtained by a mutation-inducing treatment of a parent cell line with a mutagen or spontaneously generated mutants, based on the sugar chain structure of a produced antibody molecule, 3) a method in which a desired clone is selected from mutants obtained by a mutation-inducing treatment of a parent cell line with a mutagen or spontaneously generated mutants, based on the sugar chain structure of a glycoprotein on the cell membrane, and the like.

As the mutation-inducing treatment, any treatment can be used, so long as it can induce a point mutation or a deletion or frame shift mutation in the DNA of cells of the parent cell line. Examples include treatment with ethyl nitrosourea, nitrosoguanidine, benzopyrene or an acridine pigment and treatment with radiation. Also, various alkylating agents and carcinogens can be used as mutagens. The method for allowing a mutagen to act upon cells includes the methods described in *Tissue Culture Techniques*, 3rd edition (Asakura Shoten), edited by Japanese Tissue Culture Association (1996), *Nature Genet.*, 24, 314 (2000) and the like.

The spontaneously generated mutant includes mutants which are spontaneously formed by continuing subculture under general cell culture conditions without applying special mutation-inducing treatment.

The method for selecting a mutant based on the activity of the GDP-fucose transport protein or the method for selecting a mutant based on the sugar chain structure of a glycoprotein on the cell membrane includes the methods which will be described above in the item 1 (1)(a). The method for selecting a mutant based on the sugar chain structure of a produced antibody molecule includes the methods described in the following item 5.

(4) Method for Inhibiting Transcription and/or Translation of GDP-Fucose Transport Protein The host cell of the present invention can be prepared by targeting a gene encoding the GDP-fucose transport protein and inhibiting transcription and/or translation of the target gene according to a method such as the antisense RNA/DNA technique [*Bioscience and Industry*, 50, 322 (1992), *Chemistry*, 46, 681 (1991), *Biotechnology*, 9, 358 (1992), *Trends in Biotechnology*, 10, 87 (1992); *Trends in Biotechnology*, 10, 152 (1992); *Cell Engineering*, 16, 1463 (1997)] or the triple helix technique [*Trends in Biotechnology*, 10, 132 (1992)].

2. Preparation of Transgenic Non-Human Animal or Plant or the Progenies Thereof of the Present Invention The transgenic non-human animal or plant or the progenies thereof of the present invention in which a genomic gene is modified in such a manner that the activity of a GDP-fucose transport protein can be controlled and can be prepared by targeting a gene encoding the GDP-fucose transport protein according to a known method from an embryonic stem cell, a fertilized egg cell or a plant cell prepared by the method described in the above.

A specific method is described below.

In the case of a transgenic non-human animal, the embryonic stem cell of the present invention in which the activity of the GDP-fucose transport protein is controlled can be prepared by the method described in the item 1 to an embryonic stem cell of the intended non-human animal such as cattle, sheep, goat, pig, horse, mouse, rat, fowl, monkey or rabbit.

As the embryonic stem cell, mentioned is a mutant clone in which a gene encoding the GDP-fucose transport protein is inactivated or substituted with any sequence, by a known homologous recombination technique [e.g., *Nature*, 326, 6110, 295 (1987); *Cell*, 51, 3, 503 (1987); etc.]. Using the prepared stem cell (e.g., the mutant clone), a chimeric individual comprising an embryonic stem cell clone and a normal cell can be prepared by an injection chimera method into blastocyst of fertilized egg of an animal or by an aggregation chimera method. The chimeric individual is crossed with a normal individual, so that a transgenic non-human animal in which the activity of the GDP-fucose transport protein is decreased in all the cells in the body can be obtained.

The target vector for the homologous recombination of the target gene can be prepared in accordance with a method described in *Gene Targeting, A Practical Approach*, IRL Press at Oxford University Press (1993); *Preparation of Mutant Mice using ES Cells* or the like. The target vector can be used as any of a replacement type, an insertion type and a gene trap type.

As the method for introducing the target vector into the embryonic stem cell, any method can be used, so long as it can introduce DNA into an animal cell. Examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], the injection method [*Manipulating Mouse Embryo*, Second Edition], a method using particle gun (gene gun) (Japanese Patent No. 2606856, Japanese Patent No. 2517813), the DEAE-dextran method [*Biomanual Series* 4-*Gene Transfer and Expression Analysis* (Yodo-sha), edited by Takashi Yokota and Kenichi Arai (1994)], the virus vector method [*Manipulating Mouse Embryo*, Second Edition] and the like.

The method for efficiently selecting a homologous recombinant includes a method such as the positive selection, promoter selection, negative selection or polyA selection described in *Gene Targeting, A Practical Approach*, IRL Press at Oxford University Press (1993), or the like. Specifically, in the case of the target vector containing hprt gene, positive selection which selects the homologous recombinant of the hprt gene can be carried out by introducing the target vector into the hprt gene-defected embryonic stem cell, culturing the embryonic stem cell in a medium containing aminopterin, hypoxanthine and thymidine, and selecting an aminopterin-resistant clone. In the case of the target vector containing a neomycin-resistant gene, positive selection which selects a homologous recombinant containing neomycin-resistant gene can be carried out by culturing the vector-introduced embryonic stem cell in a medium containing G418, and selecting a G418-resistant gene. In the case of the target vector containing DT gene, negative selection which selects a DT gene-free homologous recombinant clone can be carried out by culturing the vector-introduced embryonic stem cell, and selecting the grown clone. (The recombinants in which DT gene is introduced into a chromosome at random other than the homogenous recombination cannot grow due to the toxicity of DT since the DT gene is expressed while integrated in the chromosome). The method for selecting the homogenous recombinant of interest among the selected clones include the Southern hybridization for genomic DNA (*Molecular Cloning*, Second Edition), PCR [*PCR Protocols*, Academic Press (1990)] and the like.

When the embryonic stem cell is introduced into a fertilized egg by using an aggregation chimera method, in general, a fertilized egg at the development stage before 8-cell stage is preferably used. When the embryonic stem cell is introduced into a fertilized egg by using an injection chimera method, in general, it is preferred that 8 fertilized egg at the development stage from 8-cell stage to batstocyst stage is preferably used.

When the fertilized egg is transplanted into a female mouse, it is preferred to artificially transplant or implant a fertilized egg obtained from a pseudopregnant female mouse in which fertility is induced by mating with a male non-human mammal which is subjected to vasoligation. Although the psuedopregnant female mouse can be obtained by natural mating, the pseudopregnant female mouse in which fertility is induced can also be obtained by mating with a male mouse after administration of a luteinizing hormone-releasing hormone (hereinafter referred to as "LHRH") or its analogue thereof. The analogue of LHRH includes [3,5-Dil-Tyr5]-LHRH, [Gln8]-LHRH, [D-Ala6]-LHRH des-Gly10-[D-His (Bzl)6]-LHRH ethylamide and the like.

Also, a fertilized egg cell of the present invention in which the activity of the GDP-fucose transport protein is decreased or deleted can be prepared by applying the method described in the item 1 to fertilized egg of a non-human animal of interest such as cattle, sheep, goat, pig, horse, mouse, rat, fowl, monkey, rabbit or the like.

A transgenic non-human animal in which the activity of the GDP-fucose transport protein is decreased can be prepared by transplanting the prepared fertilized egg cell into the oviduct or uterus of a pseudopregnant female using the embryo transplantation method described in *Manipulating Mouse Embryo*, Second Edition or the like, followed by childbirth by the animal.

In the case of a transgenic plant, the callus of the present invention in which the activity of the GDP-fucose transport protein is decreased or deleted can be prepared by applying the method described in the item 1 to a callus or cell of the plant of interest.

A transgenic plant in which the activity of the GDP-fucose transport protein is decreased can be prepared by culturing the prepared callus in a medium comprising auxin and cytokinin to redifferentiate it in accordance with a known method [*Tissue Culture (Soshiki Baiyo)*, 20 (1994); *Tissue Cultur (Soshiki Baiyo)e*, 21 (1995); *Trends in Biotechnology*, 15, 45(1997)].

3. Method for Producing Antibody Composition

The antibody composition can be obtained by expressing it in a host cell using the methods described in *Molecular Cloning*, Second Edition; *Current Protocols in Molecular Biology; Antibodies, A Laboratory Manual*, Cold Spring Harbor Laboratory, 1988 (hereinafter sometimes referred to as "*Antibodies*"); *Monoclonal Antibodies: Principles and Practice*, Third Edition, Acad. Press, 1993 (hereinafter sometimes referred to as "*Monoclonal Antibodies*"); and *Antibody Engineering, A Practical Approach*, IRL Press at Oxford University Press (hereinafter sometimes referred to as "*Antibody Engineering*"), for example, as follows.

A cDNA of an antibody molecule is prepared.

Based on the prepared full length cDNA of an antibody molecule, a DNA fragment of an appropriate length comprising a moiety encoding the protein is prepared, if necessary.

A recombinant vector is prepared by inserting the DNA fragment or the full length cDNA into downstream of the promoter of an appropriate expression vector.

A transformant which produces the antibody molecule can be obtained by introducing the recombinant vector into a host cell suitable for the expression vector.

As the host cell, any of yeast, an animal cell, an insect cell, a plant cell or the like can be used, so long as it can express the gene of interest. An animal cell is preferred.

A cell such as yeast, animal cell, insect cell, plant cell or the like into which an enzyme relating to the modification of an N-glycoside-linked sugar chain which binds to the Fc region of the antibody molecule is introduced by a genetic engineering technique can also be used as the host cell.

The host cell used for the production of the antibody of the present invention includes a cell in which the activity of the GDP-fucose transport protein is more deleted or decreased than its parent cell prepared in the above 1.

As the expression vector, a vector which is autonomously replicable in the host cell or can be integrated into the chromosome and comprises a promoter at such a position that the DNA encoding the antibody molecule of interest can be transferred is used.

The cDNA can be prepared from a human or non-human tissue or cell using, e.g., a probe primer specific for the antibody molecule of interest according to the methods described in "Preparation method of cDNA" in the item 1(1)(a).

When a yeast is used as the host cell, the expression vector includes YEP13 (ATCC 37115), YEp24 (ATCC 37051), YCp50(ATCC 37419) and the like.

Any promoter can be used, so long as it can function in yeast. Examples include a promoter of a gene of the glycolytic pathway such as a hexose kinase gene, PHO5 promoter, PGK promoter, GAP promoter, ADH promoter, gal 1 promoter, gal 10 promoter, heat shock protein promoter, MF α1 promoter, CUP 1 promoter and the like.

The host cell includes microorganisms belonging to the genus *Saccharomyces*, the genus *Schizosaccharomyces*, the genus *Kluyveromyces*, the genus *Trichosporon*, the genus *Schwanniomyces* and the like, such as *Saccharomyces cerevisiae, Schizosaccharomyces pombe, Kluyveromyces lactis, Trichosporon pullulans* and *Schwanniomyces alluvius*.

As the method for introducing the recombinant vector, any method can be used, so long as it can introduce DNA into yeast. Examples include electroporation [*Methods in Enzymology*, 94, 182 (1990)], spheroplast method [*Proc. Natl. Acad. Sci. USA*, 84, 1929 (1978)], lithium acetate method [*J. Bacteriol.*, 153, 163 (1983)], a method described in *Proc. Natl. Acad. Sci. USA*, 75, 1929 (1978) and the like.

When an animal cell is used as the host, the expression vector includes pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840 (1987)], pcDNAI/Amp (manufactured by Invitrogen), pREP4 (manufactured by Invitrogen), pAGE103 [*J. Biochemistry*, 101, 1307 (1987)], pAGE210 and the like.

Any promoter can be used, so long as it can function in an animal cell. Examples include a promoter of IE (immediate early) gene of cytomegalovirus (CMV), an early promoter of SV40, a promoter of retrovirus, a promoter of metallothionein, a heat shock promoter, an SRα promoter and the like. Also, an enhancer of the IE gene of human CMV may be used together with the promoter.

The host cell includes a human cell such as Namalwa cell, a monkey cell such as COS cell, a Chinese hamster cell such as CHO cell or HBT5637 (Japanese Published Unexamined Patent Application No. 299/88), a rat myeloma cell, a mouse myeloma cell, a cell derived from syrian hamster kidney, an embryonic stem cell, a fertilized egg cell and the like.

As the method for introducing the recombinant vector, any method can be used, so long as it can introduce DNA into an animal cell. Examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], the injection method [*Manipulating the Mouse Embryo, A Laboratory Manual*], a method using particle gun (gene gun) (Japanese Patent No. 2606856, Japanese Patent No. 2517813), the DEAE-dextran method [*Biomanual Series 4-Gene Transfer and Expression Analysis* (Yodo-sha), edited by Takashi Yokota and Kenichi Arai (1994)], the virus vector method (*Manipulating Mouse Embryo*, Second Edition) and the like.

When an insect cell is used as the host, the protein can be expressed by the method described in *Current Protocols in Molecular Biology, Baculovirus Expression Vectors, A Laboratory Manual*, W.H. Freeman and Company, New York (1992), *Bio/Technology*, 6, 47 (1988) or the like.

That is, the protein can be expressed by co-introducing a recombinant gene-introducing vector and a baculovirus into an insect cell to obtain a recombinant virus in an insect cell culture supernatant and then infecting the insect cell with the recombinant virus.

The gene introducing vector used in the method includes pVL1392, pVL1393, pBlueBacIII (all manufactured by Invitrogen) and the like.

The baculovirus includes *Autographa californica* nuclear polyhedrosis virus which is infected by an insect of the family Barathra.

The insect cell includes *Spodoptera frugiperda* oocytes Sf9 and Sf21 [*Current Protocols in Molecular Biology, Baculovirus Expression Vectors, A Laboratory Manual*, W.H. Freeman and Company, New York (1992)], a *Trichoplusia ni* oocyte High 5 (manufactured by Invitrogen) and the like.

The method for the co-introducing the recombinant gene-introducing vector and the baculovirus for preparing the recombinant virus includes the calcium phosphate method (Japanese Published Unexamined Patent Application No. 227075/90), the lipofection method [*Proc. Natl. Acad. Sci. USA*, 84, 7413 (1987)] and the like.

When a plant cell is used as the host cell, the expression vector includes Ti plasmid, tobacco mosaic virus vector and the like.

As the promoter, any promoter can be used, so long as it can function in a plant cell. Examples include cauliflower mosaic virus (CaMV) 35S promoter, rice actin 1 promoter and the like.

The host cell includes plant cells of tobacco, potato, tomato, carrot, soybean, rape, alfalfa, rice, wheat, barley and the like.

As the method for introducing the recombinant vector, any method can be used, so long as it can introduce DNA into a plant cell. Examples include a method using *Agrobacterium* (Japanese Published Unexamined Patent Application No. 140885/84, Japanese Published Unexamined Patent Application No. 70080/85, WO 94/00977), electroporation (Japanese Published Unexamined Patent Application No. 251887/85), a method using a particle gun (gene gun) (Japanese Patent No. 2606856, Japanese Patent No. 2517813) and the like.

As the method for expressing an antibody gene, secretion production, expression of a fusion protein and the like can be carried out in accordance with the method described in *Molecular Cloning*, Second Edition or the like, in addition to the direct expression.

When a gene is expressed by yeast, an animal cell, an insect cell or a plant cell into which a gene relating to the synthesis of a sugar chain is introduced, an antibody molecule to which a sugar or a sugar chain is added by the introduced gene can be obtained.

An antibody composition can be obtained by culturing the obtained transformant in a medium to produce and accumulate the antibody molecule in the culture and then recovering it from the resulting culture. The method for culturing the transformant in a medium can be carried out in accordance with a general method which is used for the culturing of host cells.

As the medium for culturing a transformant obtained using a eukaryote, such as yeast, as the host, the medium may be either a natural medium or a synthetic medium, so long as it comprises materials such as a carbon source, a nitrogen source and an inorganic salt which can be assimilated by the organism and culturing of the transformant can be efficiently carried out.

As the carbon source, those which can be assimilated by the organism can be used. Examples include carbohydrates such as glucose, fructose, sucrose, molasses containing them, starch and starch hydrolysate; organic acids such as acetic acid and propionic acid; alcohols such as ethanol and propanol; and the like.

The nitrogen source includes ammonia; ammonium salts of inorganic acid or organic acid such as ammonium chloride, ammonium sulfate, ammonium acetate and ammonium phosphate; other nitrogen-containing compounds, peptone; meat extract; yeast extract, corn steep liquor; casein hydrolysate; soybean meal, soybean meal hydrolysate; various fermented cells and hydrolysates thereof; and the like.

The inorganic material includes potassium dihydrogen phosphate, dipotassium hydrogen phosphate, magnesium phosphate, magnesium sulfate, sodium chloride, ferrous sulfate, manganese sulfate, copper sulfate, calcium carbonate, and the like The culturing is carried out generally under aerobic conditions such as a shaking culture or submerged-aeration stirring culture. The culturing temperature is preferably 15 to 40° C., and the culturing time is generally 16 hours to 7 days. During the culturing, the pH is maintained at 3.0 to 9.0. The pH is adjusted using an inorganic or organic acid, an alkali solution, urea, calcium carbonate, ammonia or the like.

If necessary, an antibiotic such as ampicillin or tetracycline may be added to the medium during the culturing.

When a microorganism transformed with a recombinant vector obtained by using an inducible promoter as the promoter is cultured, an inducer may be added to the medium, if necessary. For example, when a microorganism transformed with a recombinant vector obtained by using lac promoter is cultured, isopropyl-β-D-thiogalactopyranoside may be added to the medium, and when a microorganism transformed with a recombinant vector obtained by using trp promoter is cultured, indoleacrylic acid may be added to the medium.

When a transformant obtained by using an animal cell as the host is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual-Preparation of Transgenic Mice* (Kodan-sha), edited by M. Katsuki (1987)], the media to which fetal calf serum, etc. are added, and the like.

The culturing is carried out generally at a pH of 6 to 8 and 30 to 40° C. for 1 to 7 days in the presence of 5% $CO_2$. Also, the culturing may be carried out for one day to several months according to a culturing method such as fed-batch culturing or hollo-fiber.

If necessary, an antibiotic such as kanamycin or penicillin may be added to the medium during the culturing.

The medium for culturing a transformant obtained by using an insect cell as the host includes generally used TNM-FH medium (manufactured by Pharmingen), Sf-900 II SFM medium (manufactured by Life Technologies), ExCell 400 and ExCell 405 (both manufactured by JRH Biosciences), Grace's Insect Medium [*Nature*, 195, 788 (1962)] and the like.

The culturing is carried out generally at a medium pH of 6 to 7 and 25 to 30° C. for 1 to 5 days.

Furthermore, antibiotics such as gentamicin may be added to the medium during the culturing, if necessary.

A transformant obtained by using a plant cell as the host can be cultured as a cell or after differentiating it into a plant cell or organ. The medium for culturing the transformant includes generally used Murashige and Skoog (MS) medium and White medium, the media to which a plant hormone such as auxin or cytokinin is added, and the like.

The culturing is carried out generally at a pH of 5 to 9 and 20 to 40° C. for 3 to 60 days.

Furthermore, if necessary, an antibiotic such as kanamycin or hygromycin may be added to the medium during the culturing.

As discussed above, an antibody composition can be produced by culturing a transformant derived from yeast, an animal cell or a plant cell, which comprises a recombinant vector into which a DNA encoding an antibody molecule is inserted, in accordance with a general culturing method, to thereby produce and accumulate the antibody composition, and then recovering the antibody composition from the culture.

The method for producing an antibody composition includes a method of intracellular expression in a host cell, a method of extracellular secretion from a host cell, and a method of production on a host cell membrane outer envelope. The method can be selected by changing the host cell used or the structure of the antibody composition produced.

When the antibody composition is produced in a host cell or on a host cell membrane outer envelope, it can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and Japanese Published Unexamined Patent Application No. 823021/94 and the like.

That is, an antibody molecule of interest can be positively secreted extracellularly from a host cell by inserting a DNA encoding the antibody molecule and a DNA encoding a signal peptide suitable for the expression of the antibody molecule into an expression vector according to a gene recombination technique, introducing the expression vector into the host cell.

Also, its production amount can be increased in accordance with the method described in Japanese Published Unexamined Patent Application No. 227075/90 according to a gene amplification system using a dihydrofolate reductase gene.

In addition, the antibody composition can also be produced by using a gene-introduced animal individual (transgenic non-human animal) or a plant individual (transgenic plant) which is constructed by the redifferentiation of an animal or plant cell into which the gene is introduced.

When the transformant is an animal individual or a plant individual, an antibody composition can be produced in accordance with a general method by rearing or cultivating it to thereby produce and accumulate the antibody composition and then recovering the antibody composition from the animal or plant individual.

The method for producing an antibody composition using an animal individual includes a method in which the antibody composition of interest is produced in an animal constructed by introducing a gene in accordance with a known method [*American Journal of Clinical Nutrition*, 63, 639S (1996); *American Journal of Clinical Nutrition*, 63, 627S (1996), *Bio/Technology*, 9, 830 (1991)].

In the case of an animal individual, an antibody composition can be produced by rearing a transgenic non-human animal into which a DNA encoding an antibody molecule is introduced to thereby produce and accumulate the antibody composition in the animal, and then recovering the antibody composition from the animal. The place in the animal where the composition is produced and accumulated includes milk (Japanese Published Unexamined Patent Application No. 309192/88) and eggs of the animal. As the promoter used in this case, any promoter can be used, so long as it can function in an animal. Preferred examples include mammary gland cell-specific promoters such as α casein promoter, β casein promoter, β lactoglobulin promoter, whey acidic protein promoter and the like.

The process for producing an antibody composition using a plant individual includes a method in which an antibody composition is produced by cultivating a transgenic plant into which a DNA encoding an antibody molecule is introduced by a known method [*Tissue Culture (Soshiki Baiyo)*, 20 (1994); *Tissue Culture (Soshiki Baiyo)*, 21 (1995); *Trends in Biotechnology*, 15, 45 (1997)] to produce and accumulate the antibody composition in the plant, and then recovering the antibody composition from the plant.

Regarding purification of an antibody composition produced by a transformant into which a gene encoding an antibody molecule is introduced, for example, when the antibody composition is intracellularly expressed in a dissolved state, the cells after culturing are recovered by centrifugation, suspended in an aqueous buffer and then disrupted using ultrasonic oscillator, French press, Manton Gaulin homogenizer, dynomill or the like to obtain a cell-free extract, which is centrifuged to obtain a supernatant, and a purified product of the antibody composition can be obtained by subjecting the supernatant to a general enzyme isolation and purification techniques such as solvent extraction; salting out and desalting with ammonium sulfate, etc.; precipitation with an organic solvent; anion exchange chromatography using a resin such as DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography, chromatofocusing, electrophoresis such as isoelectric focusing; and the like which may be used alone or in combination.

When the antibody composition is expressed intracellularly by forming an insoluble body, the cells are recovered, disrupted and centrifuged in the same manner, and the insoluble body of the antibody composition is recovered as a precipitation fraction. The recovered insoluble body of the antibody composition is solubilized with a protein denaturing agent. The antibody composition is made into a normal three-dimensional structure by diluting or dialyzing the solubilized solution, and then a purified product of the antibody composition is obtained by the same isolation purification method.

When the antibody composition is secreted extracellularly, the antibody composition or derivatives thereof can be recovered from the culture supernatant. That is, the culture is treated by a technique such as centrifugation to obtain a soluble fraction, and a purified preparation of the antibody composition can be obtained from the soluble fraction by the same isolation purification method.

The antibody composition thus obtained includes an antibody, the fragment of the antibody, a fusion protein comprising the Fc region of the antibody, and the like.

As examples for obtaining the antibody composition, processes for producing a humanized antibody composition and an Fc fusion protein are described below in detail, but other antibody compositions can also be obtained in a manner similar to the methods.

A. Preparation of Humanized Antibody Composition (1) Construction of Vector for Expression of Humanized Antibody Expression A vector for expression humanized antibody is an expression vector for animal cell into which genes encoding CH and CL of a human antibody are inserted, which can be constructed by cloning each of genes encoding CH and CL of a human antibody into an expression vector for animal cell.

The C regions of a human antibody may be CH and CL any human antibody. Examples include the C region belonging to IgG1 subclass in the H chain of a human antibody (hereinafter referred to as "hCγ1"), the C region belonging to κ class in the L chain of a human antibody (hereinafter referred to as "hCκ"), and the like.

As the genes encoding CH and CL of a human antibody, a chromosomal DNA comprising an exon and an intron can be used, and a cDNA can also be used.

As the expression vector for animal cell, any vector can be used, so long as a gene encoding the C region of a human antibody can be inserted thereinto and expressed therein. Examples include pAGE107 [*Cytotechnology*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981), pSG1 β d2-4 [*Cytotechnology*, 4, 173 (1990)] and the like. The promoter and enhancer in the expression vector for animal cell includes SV40 early promoter and enhancer [*J. Biochem.*, 101, 1307 (1987)], Moloney mouse leukemia virus LTR promoter [*Biochem. Biophys. Res Commun.*, 149, 960 (1987)], immunoglobulin H chain promoter [*Cell*, 4, 479 (1985)] and enhancer [*Cell*, 33, 717 (1983)], and the like.

The vector for expression of humanized antibody may be either of a type in which genes encoding the H chain and L chain of an antibody exist on separate vectors or of a type in which both genes exist on the same vector (hereinafter referred to "tandem type"). In respect of easiness of construction of a vector for expression of humanized antibody, easiness of introduction into animal cells, and balance between the expression amounts of the H and L chains of an antibody in animal cells, a tandem type of the vector expression for humanized antibody is more preferred [*J. Immunol. Methods*, 167, 271 (1994)].

The constructed vector for expression of humanized antibody can be used for expression of a human chimeric antibody and a human CDR-grafted antibody in animal cells.

(2) Preparation Method of cDNA Encoding V Region of Non-Human Animal Antibody cDNAs encoding VH and VL of a non-human animal antibody such as a mouse antibody can be obtained in the following manner.

A cDNA is synthesized from mRNA extracted from a hybridoma cell which produces the mouse antibody of interest. The synthesized cDNA is cloned into a vector such as a phage or a plasmid to obtain a cDNA library. Each of a recombinant phage or recombinant plasmid comprising a cDNA encoding VH and a recombinant phage or recombinant plasmid comprising a cDNA encoding VL is isolated from the library by using a C region part or a V region part of an existing mouse antibody as the probe. Full nucleotide sequences of VH and VL of the mouse antibody of interest on the recombinant phage or recombinant plasmid are determined, and full length amino acid sequences of VH and VL are deduced from the nucleotide sequences.

As the non-human animal, any animal such as mouse, rat, hamster or rabbit can be used, so long as a hybridoma cell can be produced therefrom.

The method for preparing a total RNA from a hybridoma cell includes the guanidine thiocyanate-cesium trifluoroacetate method [*Methods in Enzymology*, 154, 3 (1987)] and the like, and the method for preparing mRNA from total RNA includes an oligo(dT)-immobilized cellulose column method (*Molecular Cloning*, Second Edition) and the like. In addition, a kit for preparing mRNA from a hybridoma cell includes Fast Track mRNA Isolation Kit (manufactured by Invitrogen), Quick Prep mRNA Purification Kit (manufactured by Pharmacia).

The method for synthesizing a cDNA and preparing a cDNA library includes the usual methods (*Molecular Cloning*, Second Edition, *Current Protocols in Molecular Biology*, Supplement 1-34), methods using a commercially available kit such as SuperScript™, Plasmid System for cDNA Synthesis and Plasmid Cloning (manufactured by GIBCO BRL) or ZAP-cDNA Synthesis Kit (manufactured by Stratagene), and the like.

In preparing the cDNA library, the vector into which a cDNA synthesized by using mRNA extracted from a hybridoma cell as the template is inserted may be any vector, so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning, A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [*Gene*, 33, 103 (1985)] and the like.

As *Escherichia coli* into which the cDNA library constructed from a phage or plasmid vector is introduced, any *Escherichia coli* can be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

As the method for selecting a cDNA clone encoding VH and VL of a non-human animal antibody from the cDNA library, a colony hybridization or a plaque hybridization using an isotope- or fluorescence-labeled probe can be used (*Molecular Cloning*, Second Edition). The cDNA encoding VH and VL can also be prepared by preparing primers and carrying out polymerase chain reaction (hereinafter referred to as "PCR"; *Molecular Cloning*, Second Edition; *Current Protocols in Molecular Biology*, Supplement 1-34) using a cDNA synthesized from mRNA or a cDNA library as the template.

The nucleotide sequences of the cDNAs can be determined by digesting the selected cDNAs with appropriate restriction enzymes, cloning the fragments into a plasmid such as pBluescript SK(-) (manufactured by Stratagene), carrying out the reaction of a generally used nucleotide sequence analyzing method such as the dideoxy method of Sanger et al. [*Proc. Natl. Acad. Sci., USA*, 74, 5463 (1977)], and then analyzing the clones using an automatic nucleotide sequence analyzer such as A.L.F. DNA Sequencer (manufactured by Pharmacia). Whether or not the obtained cDNAs encode the full length amino acid sequences of VH and VL of the antibody comprising a secretory signal sequence can be confirmed by deducing the full length amino acid sequences of VH and VL from the determined nucleotide sequence and comparing them with the full length amino acid sequences of VH and VL of known antibodies [*Sequences of Proteins of Immunological Interest*, US Dep. Health and Human Services (1991), hereinafter referred to as "*Sequences of Proteins of Immunological Interest*"].

(3) Analysis of Amino Acid Sequence of V Region of Non-Human Animal Antibody

Regarding the full length amino acid sequences of VH and VL of the antibody comprising a secretory signal sequence, the length of the secretory signal sequence and the N-terminal amino acid sequences can be deduced and subgroups to which they belong can also be found, by comparing them with the full length amino acid sequences of VH and VL of known antibodies (*Sequences of Proteins of Immunological Interest*). In addition, the amino acid sequences of each CDR pf VH and VL can also be found by comparing them with the amino acid sequences of VH and VL of known antibodies (*Sequences of Proteins of Immunological Interest*).

(4) Construction of Human Chimeric Antibody Expression Vector

A human chimeric antibody expression vector can be constructed by cloning cDNAs encoding VH and VL of a non-human animal antibody into upstream of genes encoding CH and CL of a human antibody in the vector for expression of humanized antibody described in the item 3(1). For example, a human chimeric antibody expression vector can be constructed by linking each of cDNAs encoding VH and VL of a non-human animal antibody to a synthetic DNA comprising nucleotide sequences at the 3'-terminals of VH and VL of a non-human animal antibody and nucleotide sequences at the 5'-terminals of CH and CL of a human antibody and also having a recognition sequence of an appropriate restriction enzyme at both terminals, and by cloning them into upstream of genes encoding CH and CL of a human antibody contained in the vector for expression of humanized antibody described in the item 3(1).

(5) Construction of cDNA Encoding V Region of Human CDR-Grafted Antibody cDNAs encoding VH and VL of a human CDR-grafted antibody can be obtained as follows. First, amino acid sequences of the frameworks (hereinafter referred to as "FR") of VH and VL of a human antibody for grafting CDR of VH and VL of a non-human animal antibody is selected. As the amino acid sequences of FRs of VH and VL of a human antibody, any amino acid sequences can be used so long as they are derived from a human antibody. Examples include amino acid sequences of FRs of VH and VL of human antibodies registered at databases such as Protein Data Bank, amino acid sequences common in each subgroup of FRs of VH and VL of human antibodies (*Sequences of Proteins of Immunological Interest*) and the like. In order to produce a human CDR-grafted antibody having enough activities, it is preferred to select an amino acid sequence having a homology as high as possible (at least 60% or more) with amino acid sequences of VH and VL of a non-human animal antibody of interest.

Next, the amino acid sequences of CDRs of VH and VL of the non-human animal antibody of interest are grafted to the selected amino acid sequences of FRs of VH and VL of a human antibody to design amino acid sequences of VH and VL of the human CDR-grafted antibody. The designed amino acid sequences are converted into DNA sequences by considering the frequency of codon usage found in nucleotide sequences of antibody genes (*Sequences of Proteins of Immunological Interest*), and the DNA sequences encoding the amino acid sequences of VH and VL of the human CDR-grafted antibody are designed. Based on the designed DNA sequences, several synthetic DNAs having a length of about 100 bases are synthesized, and PCR is carried out by using them. In this case, it is preferred in each of the H chain and the L chain that 6 synthetic DNAs are designed in view of the reaction efficiency of PCR and the lengths of DNAs which can be synthesized.

Also, they can be easily cloned into the vector for expression of humanized antibody described in the item 3(1) by introducing recognition sequences of an appropriate restriction enzyme into the 5'-terminals of the synthetic DNA on both terminals. After the PCR, the amplified product is cloned into a plasmid such as pBluescript SK(−) (manufactured by Stratagene) and the nucleotide sequences are determined by the method in the item 3(2) to thereby obtain a plasmid having DNA sequences encoding the amino acid sequences of VH and VL of the desired human CDR-grafted antibody.

(6) Modification of Amino Acid Sequence of V Region of Human CDR-Grafted Antibody It is known that when a human CDR-grafted antibody is produced by simply grafting only CDRs in VH and VL of a non-human animal antibody into FRs in VH and VL of a human antibody, its antigen-binding activity is lower than that of the original non-human animal antibody [*BIO/TECHNOLOGY*, 9, 266 (1991)]. As the reason, it is considered that several amino acid residues of Frs other than CDRs directly or indirectly relate to antigen-binding activity in VH and VL of the original non-human animal antibody, and that they are changed to different amino acid residues of FRs in VH and VL of a human antibody. In order to solve the problem, in human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human animal antibody to thereby increase the antigen binding activity which has been decreased [*BIO/TECHNOLOGY*, 9, 266 (1991)].

In the preparation of a human CDR-grafted antibody, it is the most important to efficiently identify the amino acid residues relating to the antigen binding activity in FR. For identifying the amino acid residues of FR relating to the antibody-antigen binding activity, the three-dimensional structure of an antibody is constructed, and analyzed by X-ray crystallography [*J. Mol. Biol.*, 112, 535 (1977)], computer-modeling [*Protein Engineering*, 7, 1501 (1994)] or the like. Although the information of the three-dimensional structure of antibodies has been useful in the production of a human CDR-grafted antibody, method for producing a human CDR-grafted antibody which can be applied to all antibodies has not been established yet. Therefore, various attempts must be currently be necessary, for example, several modified antibodies of each antibody are produced and the relationship between each of the modified antibodies and its antibody binding activity is examined.

The amino acid sequence of FRs in VH and VL of a human antibody can be modified by using a synthetic DNA for modification according to PCR as described in the item 3(5). With regard to the amplified product obtained by the PCR, the nucleotide sequence is determined according to the method as described in the item 3(2) so that whether the objective modification has been carried out is confirmed.

(7) Construction of Human CDR-Grafted Antibody Expression Vector

A human CDR-grafted antibody expression vector can be constructed by cloning the cDNAs encoding VH and VL of the human CDR-grafted antibody constructed in the items 3(5) and (6) into upstream of the gene encoding CH and CL of a human antibody in the vector for expression of humanized antibody described in the item 3(1). For example, the human CDR-grafted antibody expression vector can be constructed by introducing recognizing sequences of an appropriate restriction enzyme into the 5'-terminals of both terminals of a synthetic DNA fragment, among the synthetic DNA fragments which are used when PCR is carried out in the items 3(5) and (6) for constructing VH and VL of the human CDR-grafted antibody, so that they are cloned into upstream of the genes encoding CH and CL of a human antibody in the vector for expression of humanized antibody described in the item 3(1) in such a manner that they can be expressed in a suitable form.

(8) Stable Production of Humanized Antibody

A transformant capable of stably producing a human chimeric antibody and a human CDR-grafted antibody (both hereinafter referred to as "humanized antibody") can be obtained by introducing the humanized antibody expression vector described in the items 3(4) and (7) into an appropriate animal cell.

The method for introducing a humanized antibody expression vector into an animal cell includes electroporation [Japanese Published Unexamined Patent Application No. 257891/90, *Cytotechnology*, 3, 133 (1990)] and the like.

As the animal cell into which a humanized antibody expression vector is introduced, any cell can be used so long as it is an animal cell which can produce the humanized antibody.

Examples include mouse myeloma cells such as NS0 cell and SP2/0 cell, Chinese hamster ovary cells such as CHO/dhfr⁻ cell and CHO/DG44 cell, rat myeloma such as YB2/0 cell and IR983F cell, BHK cell derived from a syrian hamster kidney, a human myeloma cell such as Namalwa cell, and the like, and a Chinese hamster ovary cell CHO/DG44 cell, a rat myeloma YB2/0 cell and the host cells of the present invention described in the item 1 are preferred.

After introduction of the humanized antibody expression vector, a transformant capable of stably producing the humanized antibody can be selected by using a medium for animal cell culture comprising an agent such as G418 sulfate (hereinafter referred to as "G418"; manufactured by SIGMA) and the like in accordance with the method described in Japanese Published Unexamined Patent Application No. 257891/90. The medium to culture animal cells includes RPMI 1640 medium (manufactured by Nissui Pharmaceutical), GIT medium (manufactured by Nihon Pharmaceutical), EX-CELL 302 medium (manufactured by JRH), IMDM medium (manufactured by GIBCO BRL), Hybridoma-SFM medium (manufactured by GIBCO BRL), media obtained by adding various additives such as fetal bovine serum (hereinafter referred to as "FBS") to these media, and the like. The humanized antibody can be produced and accumulated in the culture supernatant by culturing the obtained transformant in a medium. The amount of production and antigen binding activity of the humanized antibody in the culture supernatant can be measured by a method such as enzyme-linked immunosorbent assay (hereinafter referred to as "ELISA"; *Antibodies, Monoclonal Antibodies*) or the like. Also, the amount of the humanized antibody produced by the transformant can be increased by using a DHFR gene amplification system in accordance with the method described in Japanese Published Unexamined Patent Application No. 257891/90.

The humanized antibody can be purified from a culture supernatant of the transformant by using a protein A column (*Antibodies, Monoclonal Antibodies*). In addition, purification methods generally used for the purification of proteins can also be used. For example, the purification can be carried out through the combination of gel filtration, ion exchange chromatography and ultrafiltration. The molecular weight of the H chain, L chain or antibody molecule as a whole of the purified humanized antibody can be measured, e.g., by polyacrylamide gel electrophoresis [hereinafter referred to as "SDS-PAGE"; *Nature,* 227, 680 (1970)], Western blotting (*Antibodies, Monoclonal Antibodies*) or the like.

B. Preparation of Fc Fusion Protein (1) Construction of Fc Fusion Protein Expression Vector A Fc fusion protein expression vector is an expression vector for animal cell into which genes encoding the Fc region of a human antibody and a protein to be fused are inserted, which can be constructed by cloning each of genes encoding the Fc region of a human antibody and the protein to be fused into an expression vector for animal cell.

The Fc region of a human antibody includes those containing a part of a hinge region and/or CH1 in addition to regions containing CH2 and CH3 regions. Also, it can be any Fc region so long as at least one amino acid of CH2 or CH3 may be deleted, substituted, added or inserted, and substantially has the binding activity to the Fcγ receptor.

As the genes encoding the Fc region of a human antibody and the protein to be fused, a chromosomal DNA comprising an exon and an intron can be used, and a cDNA can also be used. The method for linking the genes and the Fc region includes PCR using each of the gene sequences as the template (*Molecular Cloning*, Second Edition, *Current Protocols in Molecular Biology*, Supplement 1-34).

As the expression vector for animal cell, any vector can be used, so long as a gene encoding the C region of a human antibody can be inserted thereinto and expressed therein. Examples include pAGE107 *[Cytotechnology,* 3, 133 (1990)], pAGE103 *[J. Biochem.,* 101, 1307 (1987)], pHSG274 *[Gene.* 27, 223 (1984)], pKCR *[Proc. Natl. Acad. Sci. USA,* 78, 1527 (1981), pSG1 β d2-4 *[Cytotechnology,* 4, 173 (1990)] and the like. The promoter and enhancer in the expression vector for animal cell include SV40 early promoter and enhancer [*J. Biochem.,* 101, 1307 (1987)], Moloney mouse leukemia virus LTR promoter [*Biochem. Biophys. Res. Commun.,* 149, 960 (1987)], immunoglobulin H chain promoter [*Cell,* 41, 479 (1985)] and enhancer [*Cell,* 3, 717 (1983)], and the like.

(2) Preparation of DNA Encoding Fc Region of Human Antibody and Protein to be Fused A DNA encoding the Fc region of a human antibody and the protein to be fused can be obtained in the following manner.

A cDNA is synthesized from mRNA extracted from a cell or tissue which expresses the protein of interest to be fused with Fc. The synthesized cDNA is cloned into a vector such as a phage or a plasmid to obtain a cDNA library. A recombinant phage or recombinant plasmid comprising cDNA encoding the protein of interest is isolated from the library by using the gene sequence part of the protein of interest as the probe. A full nucleotide sequence of the antibody of interest on the recombinant phage or recombinant plasmid is determined, and a full length amino acid sequence is deduced from the nucleotide sequence.

As the non-human animal, any animal such as mouse, rat, hamster or rabbit can be used so long as a cell or tissue can be removed therefrom.

The method for preparing a total RNA from a cell or tissue includes the guanidine thiocyanate-cesium trifluoroacetate method [*Methods in Enzymology,* 154, 3 (1987)] and the like, and the method for preparing mRNA from total RNA includes an oligo (dT)-immobilized cellulose column method (*Molecular Cloning*, Second Edition) and the like. In addition, a kit for preparing mRNA from a cell or tissue includes Fast Track mRNA Isolation Kit (manufactured by Invitrogen), Quick Prep mRNA Purification Kit (manufactured by Pharmacia) and the like.

The method for synthesizing a cDNA and preparing a cDNA library includes the usual methods (*Molecular Cloning*, Second Edition; *Current Protocols in Molecular Biology*, Supplement 1-34); methods using a commercially available kit such as SuperScript™, Plasmid System for cDNA Synthesis and Plasmid Cloning (manufactured by GIBCO BRL) or ZAP-cDNA Synthesis Kit (manufactured by Stratagene); and the like.

In preparing the cDNA library, the vector into which a cDNA synthesized by using mRNA extracted from a cell or tissue as the template is inserted may be any vector so long as the cDNA can be inserted. Examples include ZAP Express [*Strategies,* 5, 58 (1992)], pBluescript II SK(+) [*Nucleic Acids Research,* 17, 9494 (1989)], λzapII (manufactured by Stratagene), λgt10 and λgt11 *[DNA Cloning, A Practical Approach,* I, 49 (1985)], Lambda BlueMid (manufactured by Clontech), λExCell, pT7T3 18U (manufactured by Pharmacia), pcD2 *[Mol. Cell. Biol.,* 3, 280 (1983)], pUC18 *[Gene,* 33, 103 (1985)] and the like.

As *Escherichia coli* into which the cDNA library constructed from a phage or plasmid vector is introduced, any *Escherichia coli* can be used, so long as the cDNA library can be introduced, expressed and maintained. Examples include XL1-Blue MRF' [*Strategies,* 5, 81 (1992)], C600 *[Genetics,* 39, 440 (1954)], Y1088 and Y1090 *[Science,* 222, 778 (1983)], NM522 *[J. Mol. Biol.,* 166, 1 (1983)], K802 *[J Mol. Biol.,* 16, 118 (1966)], JM105 *[Gene,* 38, 275 (1985)] and the like.

As the method for selecting a cDNA clone encoding the protein of interest from the cDNA library, a colony hybridization or a plaque hybridization using an isotope- or fluorescence-labeled probe can be used (*Molecular Cloning*, Second Edition). The cDNA encoding the protein of interest can also be prepared by preparing primers and using a cDNA synthesized from mRNA or a cDNA library as the template according to PCR.

The method for fusing the protein of interest with the Fc region of a human antibody includes PCR. For example, synthesized oligo DNAs (primers) are designed at the 5'-terminal and 3'-terminal of the gene sequence encoding the protein of interest, and PCR is carried out to prepare a PCR product. In the same manner, primers are designed for the gene sequence encoding the Fc region of a human antibody to be fused to prepare a PCR product. At this time, the primers are designed in such a manner that the same restriction enzyme site or the same gene sequence is present between the 3'-terminal of the PCR product of the protein to be fused and the 5'-terminal of the PCR product of the Fc region. When it is necessary to modify the amino acids around the linked site, mutation is introduced by using the primer into which the mutation is introduced. PCR is further carried out by using the two kinds of the obtained PCR fragments to link the genes. Also, they can be linked by carrying out ligation after treatment with the same restriction enzyme.

The nucleotide sequence of the DNA can be determined by digesting the gene sequence linked by the above method with appropriate restriction enzymes, cloning the fragments into a plasmid such as pBluescript SK(−) (manufactured by Stratagene), carrying out analysis by using a generally used nucleotide sequence analyzing method such as the dideoxy method of Sanger et al. [*Proc. Natl. Acad. Sci. USA*, 74, 5463 (1977)] or an automatic nucleotide sequence analyzer such as A.L.F. DNA Sequencer (manufactured by Pharmacia).

Whether or not the obtained cDNA encodes the full length amino acid sequences of the Fc fusion protein containing a secretory signal sequence can be confirmed by deducing the full length amino acid sequence of the Fc fusion protein from the determined nucleotide sequence and comparing it with the amino acid sequence of interest.

(3) Stable Production of Fc Fusion Protein

A transformant capable of stably producing an Fc fusion protein can be obtained by introducing the Fc fusion protein expression vector described in the item (1) into an appropriate animal cell.

The method for introducing the Fc fusion protein expression vector into an animal cell include electroporation [Japanese Published Unexamined Patent Application No. 257891/90, *Cytotechnology*, 3, 133 (1990)] and the like.

As the animal cell into which the Fc fusion protein expression vector is introduced, any cell can be used, so long as it is an animal cell which can produce the Fc fusion protein.

Examples include mouse myeloma cells such as NS0 cell and SP2/0 cell, Chinese hamster ovary cells such as CHO/dhfr− cell and CHO/DG44 cell, rat myeloma such as YB2/0 cell and IR983F cell, BHK cell derived from a syrian hamster kidney, a human myeloma cell such as Namalwa cell, and the like, and preferred are a Chinese hamster ovary cell CHO/DG44 cell, a rat myeloma YB2/0 cell and the host cells used in the method of the present invention described in the item 1.

After introduction of the Fc fusion protein expression vector, a transformant capable of stably producing the Fc fusion protein expression vector can be selected by using a medium for animal cell culture comprising an agent such as G418 and the like in accordance with the method described in Japanese Published Unexamined Patent Application No. 257891/90. The medium to culture animal cells includes RPMI 1640 medium (manufactured by Nissui Pharmaceutical), GIT medium (manufactured by Nihon Pharmaceutical), EX-CELL 302 medium (manufactured by JRH), IMDM medium (manufactured by GIBCO BRL), Hybridoma-SFM medium (manufactured by GIBCO BRL), media obtained by adding various additives such as fetal bovine serum to these media, and the like. The Fc fission protein can be produced and accumulated in the culture supernatant by culturing the obtained transformant in a medium. The amount of production and antigen binding activity of the Fc fusion protein in the culture supernatant can be measured by a method such as ELISA. Also, the amount of the Fc fusion protein produced by the transformant can be increased by using a dhfr gene amplification system in accordance with the method described in Japanese Published Unexamined Patent Application No. 257891/90.

The Fc fusion protein can be purified from a culture supernatant culturing the transformant by using a protein A column or a protein G column (*Antibodies*, Chapter 8; *Monoclonal Antibodies*). In addition, purification methods generally used for the purification of proteins can also be used. For example, the purification can be carried out through the combination of a gel filtration, an ion exchange chromatography and an ultra-filtration. The molecular weight as a whole of the purified Fc fusion protein molecule can be measured by SDS-PAGE [*Nature*, 227, 680 (1970)], Western blotting (*Antibodies*, Chapter 12, *Monoclonal Antibodies*) or the like.

Thus, methods for producing an antibody composition using an animal cell as the host cell have been described, but, as described above, it can also be produced by yeast, an insect cell, a plant cell, an animal individual or a plant individual by the same methods on the animal cell.

When the host cell is capable of preparing the antibody molecule, the antibody composition of the present invention can be prepared by culturing the cell capable of expressing an antibody molecule according to the method described in the above item 1, culturing the cell, and recovering the antibody composition of interest.

4. Activity Evaluation of Antibody Composition

As the method for measuring the amount of the purified antibody composition, the activity to bind to an antibody and the effector function of the purified antibody composition, the known method described in *Monoclonal Antibodies, Antibody Engineering* and the like can be used.

For example, when the antibody composition is a humanized antibody, the binding activity with an antigen and the binding activity with an antigen-positive cultured clone can be measured by methods such as ELISA and an immunofluorescent method [*Cancer Immunol. Immunother.*, 36, 373 (1993)]. The cytotoxic activity against an antigen-positive cultured clone can be evaluated by measuring CDC activity, ADCC activity (*Cancer Immunol. Immunother.*, 36, 373 (1993)] and the like.

Also, safety and therapeutic effect of the antibody composition in human can be evaluated using an appropriate model of animal species relatively close to human, such as *Macaca fascicularis*.

5. Analysis of Sugar Chains of Antibody Composition

The sugar chain structure binding to an antibody molecule expressed in various cells can be analyzed in accordance with the general analysis of the sugar chain structure of a glycoprotein. For example, the sugar chain which is bound to IgG molecule comprises a neutral sugar such as galactose, mannose, fucose, an amino sugar such as N-acetylglucosamine and an acidic sugar such as sialic acid, and can be analyzed by a method such as a sugar chain structure analysis using sugar composition analysis, two dimensional sugar chain mapping or the like.

(1) Analysis of Neutral Sugar and Amino Sugar Compositions

The sugar chain composition binding to an antibody molecule can be analyzed by carrying out acid hydrolysis of sugar chains with trifluoroacetic acid or the like to release a neutral sugar or an amino sugar and measuring the composition ratio.

Examples include a method using a sugar composition analyzer (BioLC) manufactured by Dionex. The BioLC is an apparatus which analyzes a sugar composition by HPAEC-PAD (high performance anion-exchange chromatography-pulsed-amperometric detection) [*J. Liq. Chromatogr.*, 6, 1577 (1983)].

The composition ratio can also be analyzed by a fluorescence labeling method using 2-aminopyridine. Specifically, the composition ratio can be calculated in accordance with a known method [*Agric. Biol. Chem.*, 55(1), 283-284 (1991)]

by labeling an acid-hydrolyzed sample with a fluorescence with 2-aminopyridylation and then analyzing the composition by HPLC.

(2) Analysis of Sugar Chain Structure

The sugar chain structure binding to an antibody molecule can be analyzed by the two dimensional sugar chain mapping method (*Anal Biochem.*, 171, 73 (1988), *Biochemical Experimentation Methods 23—Methods for Studying Glycoprotein Sugar Chains* (Japan Scientific Societies Press) edited by Reiko Takahashi (1989)]. The two dimensional sugar chain mapping method is a method for deducing a sugar chain structure by, e.g., plotting the retention time or elution position of a sugar chain by reverse phase chromatography as the X axis and the retention time or elution position of the sugar chain by normal phase chromatography as the Y axis, respectively, and comparing them with those of known sugar chains.

Specifically, sugar chains are released from an antibody by subjecting the antibody to hydrazinolysis, and the released sugar chain is subjected to fluorescence labeling with 2-aminopyridine (hereinafter referred to as "PA") [*J. Biochem.*, 95, 197 (1984)], and then the sugar chains are separated from an excess PA-treating reagent by gel filtration, and subjected to reverse phase chromatography. Thereafter, each peak of the separated sugar chains are subjected to normal phase chromatography. The sugar chain structure can be deduced by plotting the results on a two dimensional sugar chain map and comparing them with the spots of a sugar chain standard (manufactured by Takara Shuzo) or a literature [*Anal. Biochem.*, 171, 73 (1988)].

The structure deduced by the two dimensional sugar chain mapping method can be confirmed by further carrying out mass spectrometry such as MALDI-TOF-MS of each sugar chain.

6. Application of Antibody Composition Obtained in the Present Invention

The antibody composition obtained in the present invention has high ADCC activity. An antibody having high ADCC activity is useful for preventing and treating various diseases including cancers, inflammatory diseases, immune diseases such as autoimmune diseases and allergies, cardiovascular diseases and viral or bacterial infections.

In the case of cancers, namely malignant tumors, cancer cells grow. General anti-tumor agents inhibit the growth of cancer cells. In contrast, an antibody having high antibody-dependent cell-mediated cytotoxic activity can treat cancers by injuring cancer cells through its cell killing effect, and therefore, it is more effective as a therapeutic agent than the general anti-tumor agents. At present, in the therapeutic agent for cancers, an anti-tumor effect of an antibody medicament alone is insufficient, so that combination therapy with chemotherapy has been carried out [*Science*, 280, 1197 (1998)]. If higher anti-tumor effect is found by the antibody composition of the present invention alone, the dependency on chemotherapy will be decreased and side effects will be reduced.

In immune diseases such as inflammatory diseases, autoimmune diseases and allergies, in vivo reactions of the diseases are induced by the release of a mediator molecule by immunocytes, so that the allergy reaction can be inhibited by eliminating immunocytes using an antibody having high ADCC activity.

The cardiovascular diseases include arteriosclerosis and the like. The arteriosclerosis is treated by using balloon catheter at present, but cardiovascular diseases can be prevented and treated by inhibiting growth of arterial cells in restructure after treatment by using an antibody having high ADCC activity.

Various diseases including viral and bacterial infections can be prevented and treated by inhibiting proliferation of cells infected with a virus or bacterium using an antibody having high antibody-dependent cell-mediated cytotoxic activity.

An antibody which recognizes a tumor-related antigen, an antibody which recognizes an allergy- or inflammation-related antigen, an antibody which recognizes cardiovascular disease-related antigen and an antibody which recognizes a viral or bacterial infection-related antigen are described below.

The antibody which recognizes a tumor-related antigen includes anti-GD2 antibody [*Anticancer Res.*, 13, 331-336 (1993)], anti-GD3 antibody [*Cancer Immunol. Immunother.*, 36, 260-266 (1993)], anti-GM2 antibody [*Cancer Res.*, 54, 1511-1516 (1994)], anti-HER2 antibody [*Proc. Natl. Acad. Sci. USA*, 89, 4285-4289 (1992)], anti-CD52 antibody [*Nature*, 332, 323-327 (1988)], anti-MAGE antibody [*British J Cancer*, 83, 493-497 (2000)], anti-HM1.24 antibody [*Molecular Immunol.*, 36, 387-395 (1999)], anti-parathyroid hormone-related protein (PTHrP) antibody [*Cancer*, 88, 2909-2911 (2000)], anti-FGF8 antibody [Proc. Natl. Acad. Sci. USA, 86, 9911-9915 (1989)], anti-basic fibroblast growth factor antibody and anti-FGF8 receptor antibody [*J. Biol. Chem.*, 265, 16455-16463 (1990)], anti-insulin-like growth factor antibody [*J. Neurosci. Res.*, 40, 647-659 (1995)], anti-insulin-like growth factor receptor antibody [*J. Neurosci. Res.*, 40, 647-659 (1995)], anti-PMSA antibody [*J. Urology*, 160, 2396-2401 (1998)], anti-vascular endothelial cell growth factor antibody [*Cancer Res.*, 57, 4593-4599 (1997)], anti-vascular endothelial cell growth factor receptor antibody [*Oncogene*, 19, 2138-2146 (2000)] and the like.

The antibody which recognizes an allergy- or inflammation-related antigen includes anti-interleukin 6 antibody [*Immunol. Rev.*, 127, 5-24 (1992)], anti-interleukin 6 receptor antibody [*Molecular Immunol.*, 31, 371-381 (1994)], anti-interleukin 5 antibody [*Immunol. Rev.*, 127, 5-24 (1992)], anti-interleukin 5 receptor antibody and anti-interleukin 4 antibody [*Cytokine*, 3, 562-567 (1991)], anti-interleukin 4 antibody [*J. Immunol. Meth.*, 217, 41-50 (1991)], anti-tumor necrosis factor antibody [*Hybridoma*, 13, 183-190 (1994)], anti-tumor necrosis factor receptor antibody [*Molecular Pharmacol.*, 58, 237-245 (2000)], anti-CCR4 antibody [*Nature*, 400, 776-780 (1999)], anti-chemokine antibody [*J Immuno. Meth.*, 174, 249-257 (1994)], anti-chemokine receptor antibody [*J. Exp. Med.*, 186, 1373-1381 (1997)] and the like.

The antibody which recognizes a cardiovascular disease-related antigen include anti-GpIIb/IIIa antibody [*J. Immunol.*, 152, 2968-2976 (1994)], anti-platelet-derived growth factor antibody [*Science*, 253, 1129-1132 (1991)], anti-platelet-derived growth factor receptor antibody [*J. Biol. Chem.*, 272, 17400-1740.4 (1997)] and anti-blood coagulation factor antibody [*Circulation*, 101, 1158-1164 (2000)] and the like.

The antibody which recognizes an antigen relating to autoimmune diseases includes an anti-auto-DNA antibody [*Immunol. Letters*, 72, 618 (2000)] and the like.

The antibody which recognizes a viral or bacterial infection-related antigen includes anti-gp120 antibody [*Structure*, 8, 385-395 (2000)], anti-CD4 antibody [*J. Rheumatology*, 25, 2065-2076 (1998)], anti-CCR4 antibody and anti-Vero toxin antibody [*J. Clin. Microbiol.*, 37, 396-399 (1999)] and the like.

These antibodies can be obtained from public organizations such as ATCC (The American Type Culture Collection), RIKEN Gene Bank at The Institute of Physical and Chemical Research, and National Institute of Bioscience and Human Technology, Agency of Industrial Science and Technology, or private reagent sales companies such as Dainippon Pharmaceutical, R & D SYSTEMS, PharMingen, Cosmo Bio and Funakoshi.

The medicament comprising the antibody composition obtained in the present invention can be administered as a therapeutic agent alone, but generally, it is preferred to provide it as a pharmaceutical formulation produced by an appropriate method well known in the technical field of manufacturing pharmacy, by mixing it with at least one pharmaceutically acceptable carrier.

It is desirable to select a route of administration which is most effective in treatment. Examples include oral administration and parenteral administration, such as buccal, tracheal, rectal, subcutaneous, intramuscular and intravenous. In the case of an antibody preparation, intravenous administration is preferred.

The dosage form includes sprays, capsules, tablets, granules, syrups, emulsions, suppositories, injections, ointments, tapes and the like.

The pharmaceutical preparation suitable for oral administration include emulsions, syrups, capsules, tablets, powders, granules and the like.

Liquid preparations such as emulsions and syrups can be produced using, as additives, water, sugars such as sucrose, sorbitol and fructose glycols such as polyethylene glycol and propylene glycol; oils such as sesame oil, olive oil and soybean oil; antiseptics such as p-hydroxybenzoic acid esters, flavors such as strawberry flavor and peppermint; and the like.

Capsules, tablets, powders, granules and the like can be produced by using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerine; and the like.

The pharmaceutical preparation suitable for parenteral administration includes injections, suppositories, sprays and the like.

Injections may be prepared by using a carrier such as a salt solution, a glucose solution or a mixture of both thereof. Also, powdered injections can be prepared by freeze-drying the antibody composition in the usual way and adding sodium chloride thereto.

Suppositories may be prepared by using a carrier such as cacao butter, hydrogenated fat or carboxylic acid.

Sprays can be prepared using the antibody composition as such or using the antibody composition together with a carrier which does not stimulate the buccal or airway mucous membrane of the patient and can facilitate absorption of the antibody composition by dispersing it as fine particles.

The carrier includes lactose, glycerol and the like. Depending on the properties of the antibody composition and the carrier, it is possible to produce pharmaceutical preparations such as aerosols and dry powders. In addition, the components exemplified as additives for oral preparations can also be added to the parenteral preparations.

Although the clinical dose or the frequency of administration varies depending on the objective therapeutic effect, administration method, treating period, age, body weight and the like, it is usually 10 µg/kg to 20 mg/kg per day and per adult.

Also, as the method for examining antitumor effect of the antibody composition against various tumor cells, in vitro tests include CDC activity measuring method, ADCC activity measuring method and the like, and in vivo tests include antitumor experiments using a tumor system in an experimental animal such as a mouse, and the like.

CDC activity and ADCC activity measurements and antitumor experiments can be carried out in accordance with the methods described in *Cancer Immunology Immunotherapy*, 36, 373 (1993), *Cancer Research*, 54, 1511 (1994) and the like.

The present invention will be described below in detail based on Examples; however, Examples are only simple illustrations, and the scope of the present invention is not limited thereto.

Example 1

Preparation of Cell Expressing GDP-Fucose Transporter Dominant Negative Mutant and Evaluation of Produced Antibody:

(1) Isolation of Gene Encoding Human GDP-Fucose Transporter

Using the human GDP-fucose transporter mRNA sequence reported in *Nature Genetics [Nature Genetics*, 8, 73 (2001)], a primer set [GDPfT-Fw primer (SEQ ID NO:5) and GDPfT-Rv primer (SEQ ID NO:6)] were designed for amplifying a full length of an open reading frame (hereinafter referred to as "ORF") of the human GDP-fucose transporter mRNA sequence to synthesize a DNA.

A PCR solution was prepared by adding 2.5 µl of human fetal brain-derived Marathon-Ready-cDNA (manufactured by Clontech), 5 µl of 20 mM deoxyribonucleotides mixed solution (manufactured by TOYOBO), 5 µl of 10×PCR buffer (manufactured by Clontech), 4 µl of GDPfT-Fw primer (equivalent to 20 pmol), 4 µl of GDPfT-Rv primer (equivalent to 20 pmol), 1 µl of Advantage DNA Polymerase (manufactured by Clontech) and 28.5 µl of sterile distilled water (manufactured by Invitrogen) into a 500 µl capacity micro-centrifugation tube (manufactured by Eppendorf). After the reaction solution was thoroughly mixed, 30 µl of mineral oil (manufactured by Sigma) was overlaid, and then, using Thermal Cycler 480 (manufactured by Perkin Elmer), the PCR was carried out by heating at 94° C. for 2 minutes, 30 cycles of a reaction at 94° C. for 30 seconds and at 64° C. for 3 minutes as one cycle, and finally heating at 72° C. for 3 minutes. From the reaction solution, 5 µl was taken out and subjected to agarose gel electrophoresis to confirm amplification of a DNA having a full length of about 1.1 kbp specific for the primers.

Next, 4 µl of the PCR solution, 1 µl of TopoTA cloning vector (manufactured by Invitrogen) and 1 µl of Salt Solution (manufactured by Invitrogen) were mixed in a 500 µl capacity micro-centrifugation tube (manufactured by Eppendorf) and allowed to stand at room temperature for 15 minutes. From the reaction solution, 1 µl was taken out, mixed with 50 µl of *Escherichia coli* XL-1 Blue Competent Cell (manufactured by Stratagene), allowed to stand on ice for 15 minutes, and then heated in a water bath at 42° C. for 45 seconds to transform *Escherichia coli* by heat shock. The *Escherichia coli* after transformation was suspended in LB medium (manufactured by DIFCO) and then inoculated on LB agar plate supplemented with 50 µg/ml ampicillin (manufactured by Wako Pure Chemical Industries). The plate was incubated at 37° C. overnight to obtain a single colony of the transformant on the LB agar. The obtained single colony was peeled off with a sterilized toothpick and cultured overnight in 50 ml of LB medium supplemented with 50 µg/ml ampicillin (manufactured by Wako Pure Chemical Industries) at 37° C. and 150 rpm (reciprocal shaking). The obtained culture broth was dispensed into centrifugation tubes (manufactured by Becton Dickinson), centrifuged at 8,000 rpm for 15 minutes at 4° C. and then the supernatant was discarded to obtain cells of the *Escherichia coli*. A plasmid DNA was purified from the thus obtained cells by using Qiaprep Midi Plasmid DNA Purification Kit (manufactured by QIAGEN) according to the manufacture's instructions attached to the kit. After confirming purity of the extracted plasmid DNA by agarose gel electrophoresis, its concentration was calculated by measuring the absorbance at a wavelength of 260 nm with a spectrophotometer (manufactured by Shimadzu). The recombinant DNA sequence of 1.1 kbp was decoded by using a DNA sequencer 377A (manufactured by Shimadzu), it was confirmed that the sequence is a full length ORF of a GDP-fucose transporter. The nucleotide sequence of the sequenced human GDP-fucose transporter cDNA is represented by SEQ ID NO:3, and the amino acid sequence of the human GDP-fucose transporter based on the nucleotide sequence is represented by SEQ ID NO:4. The obtained plasmid DNA was named pCR/hGDPfT.

(2) Construction of N-Terminal-Deleted Mutant of Human GDP-Fucose Transporter and Expression Vector Thereof A primer set [GDPfTΔ30-Fw primer (SEQ ID NO:7) and GDPfTΔ30-Rv primer (SEQ ID NO:8)] were designed for amplification of a cDNA sequence in which 30 amino acid residues at the N-terminal were deleted to synthesize a DNA. Also, the GDPfTΔ30-Fw primer was designed in such a form that a restriction enzyme HindIII site for introduction to an expression plasmid for animal cell pcDNA3.1Hyg(+) (manufactured by Invitrogen), a translation efficiency-improving Kozak sequence (CCGCC) and a translation initiation codon ATG were ligated to the upstream at the 5'-terminal of a DNA sequence encoding an amino acid residue at position 31 of the human GDP-fucose transporter.

Also, the GDPfTΔ30-Rv primer was designed in such a form that a restriction enzyme XbaI site for introduction to an expression plasmid pcDNA3.1Hyg(+) for animal cell (manufactured by Invitrogen) was ligated to the outside at the 5'-terminal of a DNA sequence encoding the translation termination codon of the human GDP-fucose transporter.

A PCR solution was prepared by adding 10 ng of the pCR/hGDPfT prepared in the item (1), 5 µl of 20 mM deoxyribonucleotides-mixed solution (manufactured by TOYOBO), 5 µl of 10×PCR buffer (manufactured by Clontech), 4 µl of GDPfTΔ30-Fw primer (equivalent to 20 pmol), 4 µl of GDPfTΔ30-Rv primer (equivalent to 20 pmol), 1 µl of KOD DNA Polymerase (manufactured by Clontech) and 28.5 µl of sterile distilled water (manufactured by Invitrogen) into a 500 µl capacity micro-centrifugation tube (manufactured by Eppendorf). The reaction solution was thoroughly mixed, 30 µl of mineral oil (manufactured by Sigma) was overlaid, and then, using Thermal Cycler 480 (manufactured by Perkin Elmer), the PCR was carried out by heating at 94° C. for 2 minutes, 30 cycles of a reaction at 94° C. for 30 seconds and at 64° C. for 3 minutes as one cycle, and finally heating at 72° C. for 3 minutes. From the reaction solution, 5 µl was taken out and subjected to agarose gel electrophoresis to confirm amplification of a DNA having a full length of about 1 kbp specific for the primers.

Next, the PCR solution was recovered in a micro-centrifugation tube, and the DNA was purified by using Qiaquick PCR Purification Kit (manufactured by QIAGEN), M buffer (manufactured by Takara Shuzo) in 1/10 volume of the DNA solution was added thereto, 10 units for each of restriction enzymes HindIII and XbaI were added thereto, and the reaction was carried out at 37° C. for 8 hours. In this restriction enzyme treatment, 10 µg of the plasmid pcDNA3.1 Hyg(+) (manufactured by Invitrogen) was also treated in the same manner.

The DNA was purified from the restriction enzyme-treated sample by using Qiaquick PCR Purification Kit (manufactured by QIAGEN) and mixed with 5 µl of the cDNA solution for N-terminal-deleted sample and 1 µl of the pcDNA3.1Hyg (+) solution, 6 µl of Ligation High (manufactured by TOYOBO) was added thereto, and the ligation was carried out at 16° C. for 30 minutes. From the reaction solution, 2 µl was taken out, mixed with 50 µl of *Escherichia coli* XL-1 Blue Competent Cell (manufactured by Stratagene), allowed to stand on ice for 15 minutes and then heated in a water bath at 42° C. for 45 seconds to transform *Escherichia coli* by heat shock. The *Escherichia coli* after transformation was suspended in LB medium (manufactured by DIFCO) and then inoculated on LB agar plate medium supplemented with 50 µg/ml ampicillin (manufactured by Wako Pure Chemical Industries). The plate was incubated at 37° C. overnight to obtain a single colony of the transformant on the agar medium. The obtained single colony was peeled off with a sterilized toothpick and cultured overnight in 50 ml of LB medium supplemented with 50 µg/ml ampicillin (manufactured by Wako Pure Chemical Industries) at 37° C. and 150 rpm (reciprocal shaking). The obtained culture broth was dispensed into centrifugation tubes (manufactured by Becton Dickinson), centrifuged at 8,000 rpm for 15 minutes at 4° C. and then the supernatant was discarded to obtain cells of the *Escherichia coli*. A plasmid DNA was purified from the obtained cells by using Qiaprep Midi Plasmid DNA Purification Kit (manufactured by QIAGEN) according to the manufacture's instructions attached thereto. After confirming purity of the purified plasmid DNA by agarose gel electrophoresis, its concentration was calculated by measuring the absorbance at a wavelength of 260 nm with a spectrophotometer (manufactured by Shimadzu). The recombinant DNA sequence of 1 kbp was decoded by using a DNA sequencer 377A (manufactured by Shimadzu), it was confirmed that the plasmid DNA is the N-terminal-deleted mutant of human GDP-fucose transporter. The thus obtained plasmid DNA was named pcDNA/hGDPfTΔ30.

(3) Introduction of Plasmid into CHO/DG44 Cell and Preparation of Transformant

Into $1.6 \times 10^6$ cells of CHO/DG44 cell [G. Urlaub and L. A. Chasin, *Proc. Natl. Acad. Sci. USA*, 77, 4216-4220 (1980)] 10 µg of the pcDNA/hGDPfTΔ30 and 10 µg of the CCR4 chimeric antibody expression plasmid pKANTEX2160 (described in WO 01/64754) were co-introduced by electroporation [*Cytotechnology*, L 133 (1990)]. Also, as a control, 10 µg of pcDNA3.1 Hyg(+) and 10 µg of pKANTEX2160 were co-introduced into CHO/DG44 cell in the same manner.

Each of the cell suspensions was suspended in 10 ml of IMDM-dFBS(10)-Hyg(500) [IMDM medium containing 10% dialyzed fetal bovine serum and 500 µg/ml hygromycin (manufactured by Wako Pure Chemical Industries)] and inoculated into T75 flask (manufactured by Greiner). After culturing at 37° C. for 2 weeks in a 5% $CO_2$ incubator, hygromycin-resistant transformants were obtained. Next, the medium was changed to a medium prepared by adding 50 nM MTX to the IMDM-dFBS(10)-Hyg(500), and culturing was carried out for 2 weeks to obtain 50 nM MTX-resistant clones. Furthermore, the medium was changed to a medium prepared by adding 200 nM MTX to the IMDM-dFBS(10)-Hyg(500) and culturing was carried out for 2 weeks to obtain 200 nM MTX-resistant clones. Expression of anti-CCR4 chimeric antibody in these 200 nM MTX-resistant clones was confirmed by the ELISA described in the item (6) of this Example using a CCR4 peptide-immobilized plate.

The transformant transfected with the N-terminal-deleted mutant of human GDP-fucose transporter is called the clone CHO/GDPftΔ30-CCR4, and the transformant transfected with pcDNA3.1Hyg(+) is called the clone CHO/pcDNA-CCR4. Also, the clone CHO/GDPftΔ30-CCR4, as a cell name of Nega-13/GDPftΔ30, has been deposited on Mar. 14, 2002, as FERM BP-7965 in International Patent Organism Depositary, National Institute of Advanced Industrial Science and Technology (Tsukuba Central 6, 1, Higashi 1-Chome Tsukuba-shi, Ibaraki-ken, Japan).

(4) Purification of Anti-CCR4 Chimeric Antibody

Anti-CCR4 chimeric antibodies produced by the clone CHO/GDPftΔ30-CCR4 and clone CHO/pcDNA-CCR4 were purified as follows.

Each of the clone CHO/GDPftΔ30-CCR4 and clone CHO/pcDNA-CCR4 was inoculated into a T182 flask (manufactured by Greiner) and cultured at 37° C. in a 5% $CO_2$ incubator until it grew up to confluent. When the cell density reached confluent stage, the culture supernatant was discarded, the cells were washed with 25 ml of PBS buffer (manufactured by Invitrogen) and then 35 ml of EXCELL301 medium (manufactured by JRH) was added thereto. After culturing at 37° C. for 1 week in a 5% $CO_2$ incubator, the culture supernatant was recovered to carry out purification with Prosep-A column (manufactured by Millipore) according to the manufacture's instructions. Protein concentrations of the purified antibodies were determined by using BCA Protein Assay Kit (manufactured by PIERCE). Regarding the purified antibodies, the antibody produced by the clone CHO/GDPftΔ30-CCR4 and the antibody produced by the clone CHO/pcDNA-CCR4 were named CHO/GDPftΔ30-CCR4 antibody and CHO/pcDNA-CCR4 antibody, respectively.

(5) Analysis of Purified Anti-CCR4 Chimeric Antibody

According to a known method [*Nature*, 227, 680 (1970)], 4 µg of each of the two purified anti-CCR4 chimeric antibodies obtained in the item (4) of this Example was subjected to SDS-PAGE to its analyze molecular weight and purity. In each of the purified anti-CCR4 chimeric antibodies, a single band of about 150 Kd in molecular weight was found under non-reducing conditions and two bands of about 50 Kd and about 25 Kd were found under reducing conditions. These molecular weights almost coincided with the molecular weights deduced from the cDNA nucleotide sequences of the antibody H chain and L chain (H chain: about 49 Kd, L chain: about 23 Kd, whole molecule: about 144 Kd), and also coincided with the reports stating that the IgG type antibody shows a molecular weight of about 150 Kd under non-reducing conditions and is degraded into H chain having a molecular weight of about 50 Kd and L chain having a molecular weight of about 25 Kd under reducing conditions due to cutting of the intramolecular S—S bond (*Antibodies*, Chapter 14, *Monoclonal Antibodies*), and it was confirmed that the anti-CCR4 chimeric antibodies were expressed and purified as antibody molecules having correct structures.

(6) Evaluation of Binding Activity to CCR4 Partial Peptide

Binding activity of the two anti-CCR4 chimeric antibodies obtained in the item (4) of this Example to a CCR4 partial peptide was measured by the following method according to the ELISA using a CCR4 peptide immobilized plate.

Binding Activity of Antibody to CCR4 Partial Peptide (ELISA)

Compound 1 (SEQ ID NO:15) was selected as a human CCR4 extracellular region peptide capable of reacting with the anti-CCR4 chimeric antibody. In order to use it in the activity measurement by ELISA, a conjugate with BSA (bovine serum albumin) (manufactured by Nacalai Tesque) was prepared by the following method and used as the antigen. That is, 100 ml of a DMSO solution comprising 25 mg/ml SMCC [4-(N-maleimidomethyl)-cyclohexane-1-carboxylic acid N-hydroxysuccinimide ester] (manufactured by Sigma) was added dropwise to 900 ml of a 10 mg BSA-containing PBS solution under stirring with a vortex; followed by gently stirring for 30 minutes. A 1 ml portion of the reaction solution was applied to a gel filtration column such as NAP-10 column equilibrated with 25 ml of PBS, and then eluted with 1.5 ml of PBS and the resulting eluate was used as a BSA-SMCC solution (BSA concentration was calculated based on $A_{280}$ measurement). Next, 250 ml of PBS was added to 0.5 mg of Compound 1 and then completely dissolved by adding 250 ml of DMF, and the BSA-SMCC solution was added thereto under vortex, followed by gently stirring for 3 hours. The reaction solution was dialyzed against PBS at 4° C. overnight, sodium azide was added thereto to give a final concentration of 0.05%, and the mixture was filtered through a 0.22 mm filter to be used as a BSA-compound 1 solution.

The prepared conjugate was dispensed at 0.05 µg/ml and 50 µl/well into a 96 well EIA plate (manufactured by Greiner) and incubated for adhesion at 4° C. overnight. After washing each well with PBS, 1% BSA-PBS was added thereto in 100 µl/well and allowed to react at room temperature to block the remaining active groups. After washing each well with PBS containing 0.05% Tween 20 (hereinafter referred to as "Tween-PBS"), a culture supernatant of a transformant was added at 50 µl/well and allowed to react at room temperature for 1 hour. After the reaction, each well was washed with Tween-PBS, and then a peroxidase-labeled goat anti-human IgG(γ) antibody solution (manufactured by American Qualex) diluted 6000-fold with 1% BSA-PBS as the secondary antibody was added at 50 µl/well and allowed to react at room temperature for 1 hour. After the reaction and subsequent washing with Tween-PBS, the ABTS substrate solution was added at 50 µl/well for color development, and 20 minutes thereafter, the reaction was stopped by adding a 5% SDS solution at 50 µl/well. Thereafter, the absorbance at 415 nm was measured.

As a result, as shown in FIG. 1, the CHO/GDPftΔ30-CCR4 antibody and CHO/pcDNA-CCR4 antibody showed almost the same antigen-binding activity to the CCR4 peptide.

(7) Evaluation of ADCC Activity to Human CCR4 High Expression Clone

The ADCC activity of the two anti-CCR4 chimeric antibodies obtained in the item (4) of this Example to a human CCR4 high expression cell CCR4/EL-4 cell (WO 01/64754) was measured according to the following method.

(a) Preparation of Target Cell Suspension

After $1.5 \times 10^6$ cells of a human CCR4-expressing CCR4/EL-4 cell described in WO 01/64754 were prepared, a 5.55 MBq equivalent of a radioactive substance $Na_2^{51}CrO_4$ was added thereto, followed by reaction at 37° C. for 1.5 hours to thereby label the cells with a radioisotope. After the reaction, the cells were washed three times by suspension in a medium and subsequent centrifugation, resuspended in the medium and then incubated at 4° C. for 30 minutes on ice for spontaneous dissociation of the radioactive substance. After centrifugation, the cells were adjusted to give a density of $2 \times 10^5$ cells/ml by adding 15 ml of the medium and used as a target cell suspension.

(b) Preparation of Human Effector Cell Suspension

From a healthy doner, 60 ml of peripheral blood was collected, 0.6 ml of heparin sodium (manufactured by Shimizu Pharmaceutical) was added thereto, followed by gently mixing. The mixture was centrifuged (800 g, 20 minutes) to isolate a mononuclear cell layer by using Lymphoprep (manufactured by AXIS SHIELD) in accordance with the manufacture's instructions. The cells were washed by centrifuging (1,400 rpm, 5 minutes) three times with a medium and then re-suspended in the medium to give a density of $5 \times 10^6$ cells/ml and used as a human effector cell suspension.

(c) Measurement of ADCC Activity

The target cell suspension prepared in the above (a) was dispensed at 50 µl ($1 \times 10^4$ cells/well) into each well of a 96 well U-bottom plate (manufactured by Falcon). Next, 100 µl of the human effector cell suspension prepared in the above (b) was added thereto ($5 \times 10^5$ cells/well, ratio of the human effector cells to the target cells was 50:1). Furthermore, each of the anti-CCR4 chimeric antibodies was added thereto to give a final concentration of 0.0001 to 10 µg/ml, followed by reaction at 37° C. for 4 hours. After the reaction, the plate was centrifuged and the amount of $^{51}Cr$ in the supernatant was measured using a γ-counter. An amount of the spontaneously dissociated $^{51}Cr$ was calculated by carrying out the same procedure using the medium alone instead of the human effector cell suspension and antibody solution, and measuring the amount of $^{51}Cr$ in the supernatant. An amount of the total dissociated $^{51}Cr$ was calculated by carrying out the same procedure using a 1 mol/L hydrochloric acid solution instead of the antibody solution and human effector cell suspension, and measuring the amount of $^{51}Cr$ in the supernatant. The ADCC activity (%) was calculated based on the following equation (1).

$$ADCC\ \text{activity}(\%) = \frac{^{51}Cr\ \text{in sample supernatant} - \text{spontaneously released}\ ^{51}Cr}{\text{total released}\ ^{51}Cr - \text{spontaneously released}\ ^{51}Cr} \times 100 \quad (1)$$

Figure 2:
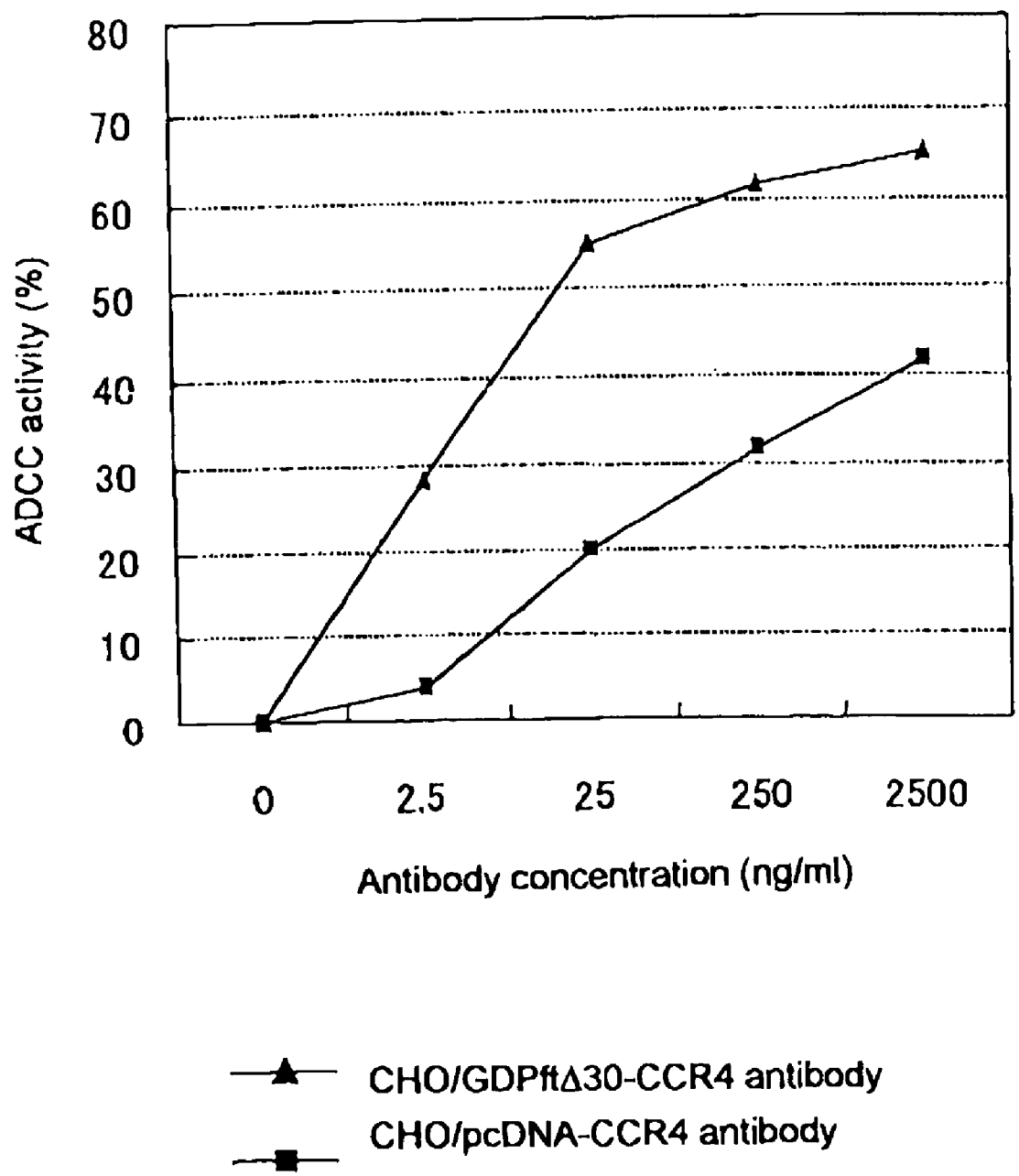
FIG. 2 shows a result of the measurement of ADCC activity by changing antibody concentrations of anti-CCR4 chimeric antibodies produced by clone CHO/GDPftΔ30-CCR4 and clone CHO/pcDNA-CCR4. The ordinate and the abscissa show the cytotoxic activity and the concentration of the anti-CCR4 chimeric antibodies in the reaction solution, respectively. "▲" and "■" show activities of CHO/GDPftΔ30-CCR4 antibody and CHO/pcDNA-CCR4 antibody, respectively.

As a result, as sown in FIG. 2, it was found that the ADCC activity of CHO/GDPftΔ30-CCR4 antibody is significantly higher than that of CHO/pcDNA-CCR4 antibody.

(8) Analysis of Sugar Chain Structure of Anti-CCR4 Chimeric Antibody

Sugar chains of the two anti-CCR4 human chimeric antibodies purified in the item (4) of this Example were analyzed. The solution of each of the purified antibodies was exchanged to 10 mM $KH_2PO_4$ by using Ultra Free 0.5-10K (manufactured by Millipore). The exchange was carried out in such a manner that the exchanging ratio became 80-fold or more. The concentration of the antibodies after the solution exchange was measured with UV-1600 (manufactured by Shimadzu). The molar absorption coefficient was calculated from the amino acid sequence of each antibody based on the following equation (2) [*Advances in Protein Chemistry*, 12, 303 (1962)], and the concentration was determined by defining the absorbance at 280 nm as 1.38 mg/ml.

$$E_{1mol/l} = A \times n1 + B \times n2 + C \times n3$$

$$E_{1mol/ml} = E_{1mol/l}/MW \quad \text{Equation (2)}$$

$E_{1mol/l}$: absorption coefficient at 280 nm ($mg^{-1}$ ml $cm^{-1}$)

$E_{1mol/ml}$: molar absorption coefficient at 280 nm ($M^{-1}$ $cm^{-1}$)

A: molar absorption coefficient of tryptophan at 280 nm=5550 ($M^{-1}$ $cm^{-1}$)

B: molar absorption coefficient of tyrosine at 280 nm=1340 ($M^{-1}$ $cm^{-1}$)

C: molar absorption coefficient of cystine at 280 nm=200 ($M^{-1}$ $cm^{-1}$)

n1: the number of tryptophan per 1 antibody molecule n2: the number of tyrosine per 1 antibody molecule n3: the number of cystine per 1 antibody molecule MW: molecular weight of antibody (g/mol)

Into Hydraclub S-204 test tube, 100 µg of each antibody was put and dried by using a centrifugal evaporator. The dried sample in the test tube was subjected to hydrazinolysis by using Hydraclub manufactured by Hohnen. The sample was allowed to react with hydrazine at 110° C. for 1 hour by using a hydrazinolysis reagent manufactured by Hohnen hydrazinolysis [*Method of Enzymology*, 83, 263 (1982)]. After the reaction, hydrazine was evaporated under a reduced pressure, and the reaction tube was returned to room temperature by allowing it to stand for 30 minutes. Next, 250 µl of an acetylation reagent manufactured by Hohnen and 25 µl of acetic anhydride were added thereto, followed by thoroughly stirred for reaction at room temperature for 30 minutes. Then, 250 µl of the acetylation reagent and 25 µl of acetic anhydride were further added thereto, followed by thoroughly stirring for reaction at room temperature for 1 hour. The sample was frozen at −80° C. in a freezer and freeze-dried for about 17 hours. Sugar chains were recovered from the freeze-dried sample using Cellulose Cartridge Glycan Preparation Kit manufactured by Takara Shuzo.

The sample sugar chain solution was dried by using a centrifugal evaporator and then subjected to fluorescence labeling with 2-aminopyridine [*J. Biochem.*, 95, 197 (1984)]. The 2-aminopyridine solution was prepared by adding 760 µl of HCl per 1 g of 2-aminopyridine (1×PA solution) and diluting the solution 10-fold with reverse osmosis purified water (10-folds diluted PA solution). The sodium cyanoborohydride solution was prepared by adding 20 µl of 1×PA solution and 430 µl of reverse osmosis purified water per 10 mg of sodium cyanoborohydride. To the sample, 67 µl of a 10 fold-diluted PA solution was added, followed by reaction at 100° C. for 15 minutes and spontaneously cooled, and 2 µl of sodium cyanoborohydride was further added thereto, followed by reaction at 90° C. for 12 hours for fluorescence labeling of the sample sugar chains. The fluorescence-labeled sugar chain group (PA-treated sugar chain group) was separated from excess reagent by using Superdex Peptide HR 10/30 column (manufactured by Pharmacia). This step was carried out by using 10 mM ammonium bicarbonate as the eluent at a flow rate of 0.5 ml/min and at a column temperature of room temperature, and using a fluorescence detector of 320 nm excitation wavelength and 400 nm fluorescence wavelength. The eluate was recovered 20 to 30 minutes after addition of the sample and dried by using a centrifugal evaporator to be used as purified PA-treated sugar chains. Next, reverse phase HPLC analysis of the purified PA-treated sugar chains was carried out by using CLC-ODS column (manufactured by Shimadzu, φ 6.0 nm×159 nm). The step was carried out at a column temperature of 55° C. and at a flow rate of 1 ml/min by using a fluorescence detector of 320 nm excitation wavelength and 400 nm fluorescence wavelength. The column was equilibrated with a 10 mM sodium phosphate buffer (pH 3.8) and elution was carried out for 80 minutes by using a 0.5% 1-butanol linear density gradient. Each of the PA-treated sugar chain was identified by post source decay analysis of each peak of the separated PA-treated sugar chains using matrix-assisted laser ionization time of flight mass spectrometry (MALDI-TOF-MS analysis), comparison of elution positions with standards of PA-treated sugar chain manufactured by Takara Shuzo, and reverse phase HPLC analysis after digestion of each PA-treated sugar chain using various enzymes. Each of the sugar chain content was calculated from each of the peak area of PA-treated sugar chain by reverse HPLC analysis. A PA-treated sugar chain whose reducing end is not N-acetylglucosamine was excluded from the peak area calculation, because it is an impurity or a by-product during preparation of PA-treated sugar chain. The analysis chart by HPLC is shown in FIG. 3. Using a sodium phosphate buffer (pH 3.8) as buffer A and a sodium phosphate buffer (pH 3.8)+0.5% 1-butanol as buffer B, the analysis was carried out by the following gradient.

| Time (minute) | 0 | 80 | 90 | 90.1 | 120 |
|---|---|---|---|---|---|
| Buffer B (%) | 0 | 60 | 60 | 0 | 0 |

Also, peaks ① to ⑧ shown in FIG. 3 correspond to the following structures (1) to (8), respectively.

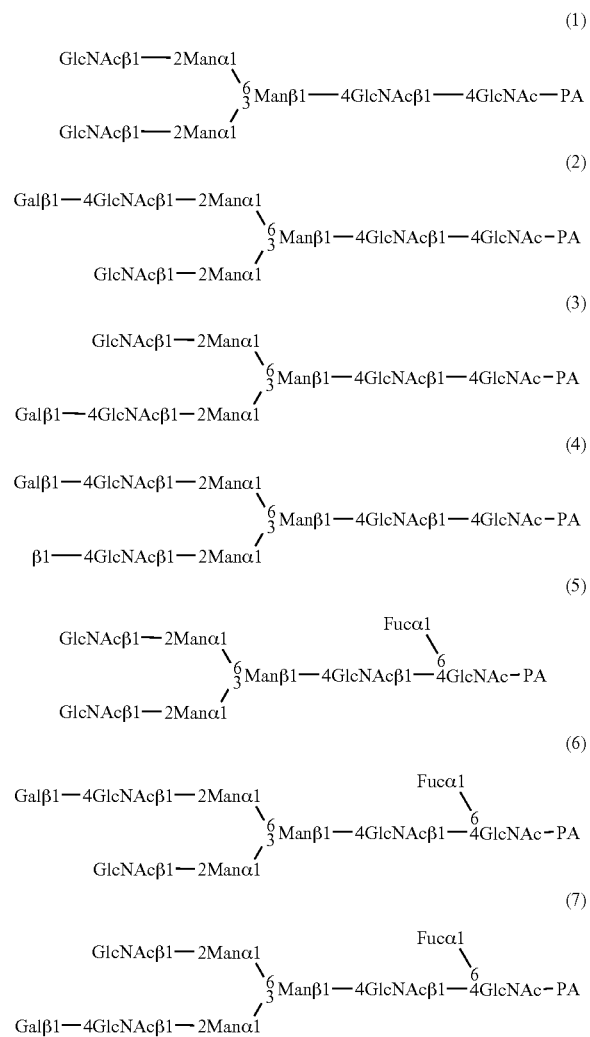

-continued

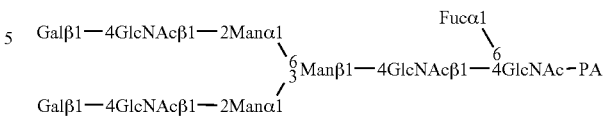

GlcNAc, Gal, Man, Fuc and PA indicate N-acetylglucosamine, galactose, mannose, fucose and a pyridylamino group, respectively. In FIG. 3, the ratio of the α1,6-fucose-free sugar chain group was calculated from the area occupied by the peaks ① to ④ among ① to ⑧, and the ratio of the α1,6-fucose-bound sugar chain group from the area occupied by the peaks ⑤ to ⑧ among ① to ⑧. The results are shown in Table 1.

TABLE 1

| Antibody | Ratio of α 1,6-fucose-free sugar chain (%) |
|---|---|
| CHO/GDPftΔ30-CCR4 antibody | 35 |
| CHO/pcDNA-CCR4 antibody | 10 |

When calculated from the peak area, the α1,6-fucose-free sugar chain content of CHO/GDPftΔ30-CCR4 was 35%, and the ratio of α1,6-fucose-bound complex sugar chain was 65%. The α1,6-fucose-free sugar chain content of CHO/pcDNA-CCR4 antibody was 10%, and the ratio of α1,6-fucose-bound complex sugar chain was 90%.

Based on the above results, it was found that the introduced N-terminal-deleted mutant of the GDP-fucose transporter acts as a dominant negative mutant of the GDP-fucose transporter and can decrease the ratio of the α1,6-fucose-bound complex sugar chain of the produced antibody.

Example 2

Isolation of Gene Encoding GDP-Fucose Transporter from Chinese Hamster Cell (1) Extraction of Total RNA Derived from CHO/DG44 Cell CHO/DG44 cell [G. Urlaub and L. A. Chasin, *Proc. Natl. Acad. Sci. USA*, 77, 4216-4220 (1980)] was suspended in IMDM medium (manufactured by Life Technologies) supplemented with 10% fetal bovine serum (manufactured by Life Technologies) and 1×concentration HT supplement (manufactured by Life Technologies) and 15 ml thereof was inoculated at a density of $2 \times 10^5$ cells/ml into a T75 flask for adherent cell culture (manufactured by Greiner). Culture was carried out at 37° C. in a 5% $CO_2$ incubator, $1 \times 10^7$ of the cells were recovered on the 2nd day of the culture, and total RNA was extracted by using RNAeasy (manufactured by QIAGEN) according to the manufacture's instructions.

(2) Preparation of Whole Single-Stranded cDNA Derived from CHO/DG44 Cell

A total RNA prepared in the above (1) was dissolved in 45 μl of sterile water, mixed with 1 μl of RQ1 RNase-Free DNase (manufactured by Promega), 5 μl of 10×DNase buffer attached thereto and 0.5 μl of RNasin ribonuclease inhibitor (manufactured by Promega) and allowed to react at 37° C. for 30 minutes to thereby degrade the genomic DNA as contaminant in the sample. After the reaction, the total RNA was re-purified by RNAeasy (manufactured by QIAGEN) and dissolved in 50 μl of sterile water.

A single-stranded cDNA was synthesized from 3 µl of the obtained total RNA by reverse transcription reaction in a 20 µl solution containing oligo(dT) as primers, using SUPER-SCRIPT™ First-Strand Synthesis System for RT-PCR (manufactured by Life Technologies) according to the manufacture's instructions. In the PCR cloning, 50 fold-diluted aqueous solution of the reaction solution was used. The solution was stored at −80° C. until its use.

(3) Preparation of Human/Chinese Hamster Ovary Cell (CHO) Chimeric GDP-Fucose Transporter cDNA A chimeric GDP-fucose transporter having human GDP-fucose transporter sequence in the primer moiety and CHO sequence in the amplified moiety was amplified by polymerase chain reaction (PCR) on the CHO/DG44 cell-derived single-stranded cDNA prepared in the above (2), using a primer set of the GDPfT-Fw primer and GDPfT-Rv primer (SEQ ID NO:5 and SEQ ID NO:6, respectively) designed based on the human GDP-fucose transporter sequence described in Example 1(1). Using ExTaq (manufactured by Takara Shuzo), 25 µl of a reaction solution [ExTaq buffer, 0.2 mM dNTPs, 0.5 µM of the above gene-specific primer set] containing 1 µl of the CHO/DG44-derived single-stranded cDNA was prepared, and the PCR was carried out by heating at 94° C. for 5 minutes, 30 cycles of a reaction at 94° C. for 1 minute, 60° C. for 1 minute and 72° C. for 1 minute as one cycle, and finally heating at 72° C. for 5 minutes. After completion of the PCR, the reaction solution was subjected to 1% agarose gel electrophoresis, and about 1,100 bp of the specific amplification fragment was purified by using GENECLEAN SPIN Kit (manufactured by BIO 101) (hereinafter, this method was used for the purification DNA fragment from agarose gel) and eluted with 20 µl of sterile water. In a 20 µl reaction solution using Ligation High (manufactured by TOYOBO), 9 µl of the amplified fragment was ligated with 50 ng of T7blue T-Vector, and *Escherichia coli* DH5α strain was transformed by using 2 µl of the reaction solution by the method of Cohen et al. [*Proc. Natl. Acad. Sci., U.S.A.*, 69, 2100 (1972)] (hereinafter, this method was used for the transformation of *Escherichia coli*). A plasmid DNA was isolated from the obtained several ampicillin-resistant colonies according to a known method [*Nucleic Acids Research*, 72, 1513 (1979)] (hereinafter, this method was used as the isolation method of plasmid). The presence or absence of insert was confirmed by the size comparison using agarose gel electrophoresis, and the nucleotide sequence was determined using DNA Sequencer 377 (manufactured by Perkin Elmer) and Big Dye Terminator Cycle Sequencing FS Ready Reaction Kit (manufactured by Perkin Elmer) according to the manufacture's instructions. After reading errors of bases accompanied by PCR were deleted by comparing the sequenced nucleotide sequences of 4 clones, it was confirmed that the inserted DNA determined by this method encodes the human/CHO chimeric GDP-fucose transporter.

(4) Synthesis of Single-Stranded cDNA for RACE

Single-stranded cDNAs for 5' and 3' RACE from the CHO/DG44 total RNA extracted in the item (1) was prepared by using SMART™ RACE cDNA Amplification Kit (manufactured by CLONTECH) according to the manufacture's instructions. In this case, PowerScript™ Reverse Transcriptase (manufactured by CLONTEC) was used as the reverse transcriptase. Each of the prepared single-stranded cDNAs was diluted 10-folds with Tricin-EDTA buffer attached to the kit and used as the template of PCR.

(5) Determination of Untranslated Region Nucleotide Sequences of Chinese Hamster GDP-Fucose Transporter by RACE Method Based on the human/CHO chimeric GDP-fucose transporter nucleotide sequence determined in the item (3), 5' RACE primers CHO-GFT-GSP5'-1 (SEQ ID NO:9) and CHO-GFT-GSP5'-2 (SEQ ID NO:10) specific for Chinese hamster GDP-fucose transporter and 3' RACE primers CHO-GFT-GSP3'-1 (SEQ ID NO:11) and CHO-GFT-GSP3'-2 (SEQ ID NO:12) specific for Chinese hamster GDP-fucose transporter were designed.

Next, using Advantage2 PCR Kit (manufactured by CLONTECH), 50 µl of a reaction solution [Advantage2 PCR buffer (manufactured by CLONTECH), 0.2 mM dNTPs, 0.2 µmol/l Chinese hamster GDP-fucose transporter-specific primers for RACE, 1×concentration of common primer (manufactured by CLONTECH)] containing 1 µl of the CHO/DG44-derived single-stranded cDNA for RACE prepared in the item (4) of this Example was prepared for polymerase chain reaction (PCR). The PCR was carried out by 20 cycles of a reaction at 94° C. for 5 seconds, 60° C. for 10 seconds and 72° C. for 2 minutes as one cycle. After completion of the reaction, the PCR was again carried out under the same conditions by using 1 µl of the reaction solution as the template and by preparing the reaction solution again. The templates and combination of primers used in the 1st and 2nd PCR and sizes of the amplified DNA fragments are shown in Table 2. After completion of the second PCR, the reaction solution was subjected to 1% agarose gel electrophoresis, and the specific amplification fragments of interest were purified and eluted with 20 µl of sterile water.

Nucleotide sequences of the PCR products obtained by the above 5' and 3' RACE were determined by a direct sequencing method by using DNA Sequencer 377 (manufactured by Perkin Elmer) and Big Dye Terminator Cycle Sequencing FS Ready Reaction Kit (manufactured by Perkin Elmer). The method was carried out according to the manufacture's instructions. Nucleotide sequences of 5' and 3' untranslated regions adjacent to the ORF of the Chinese hamster GDP-fucose transporter are shown in FIG. 4.

TABLE 2

Combination of primers used in Chinese hamster GDP-fucose transporter cDNA RACE and size of PCR products

| | Specific primer | Common primer | Size of PCR amplified products (predicted length) |
|---|---|---|---|
| 5' RACE | | | |
| 1st PCR | GFT_GSP5'-1 | UPM (Universal primer mix) | |
| 2nd PCR | GFT_GSP5'-2 | NUP (Nested Universal primer) | about 550 bp (280 bp or more) |
| 3' RACE | | | |
| 1st PCR | GFT_GSP3'-1 | UPM (Universal primer mix) | |
| 2nd PCR | GFT_GSP3'-2 | NUP (Nested Universal primer) | about 1,400 bp (270 bp or more) |

(6) Cloning of Full Length cDNA of Chinese Hamster GDP-Fucose Transporter

First, based on the nucleotide sequence of untranslated regions of GDP-fucose transporter determined in the item (5) of this Example, a primer set for Chinese hamster GDP-fucose transporter-specific amplification use, CHO#GFT#FW (SEQ ID NO:13) and CHO#GFT#RV (SEQ ID NO:14), were designed. Next, using KOD DNA polymerase (manufactured by TOYOBO), 20 μl of a reaction solution [KOD buffer, 0.2 mM dNTPs, 1.6 mM MgCl$_2$, 0.5 μM of the above gene-specific primers (CHO#GFT#FW and CHO#GFT#RV)] containing 1 μl of the CHO/DG44-derived single-stranded cDNA prepared in the item (2) of this Example was prepared, and the PCR was carried out by heating at 94° C. for 5 minutes and then 30 cycles of a reaction at 94° C. for 5 seconds, 60° C. for 10 seconds and 72° C. for 2 minutes as one cycle. After the PCR was carried out 4 times in independent experiments, each of the reaction solutions was subjected to 1% agarose gel electrophoresis, and an amplified specific fragment of about 1,250 bp was purified by using GENECLEAN SPIN Kit (manufactured by BIO 101) and eluted with 20 μl of sterile water. In a 20 μl solution containing Ligation High (manufactured by TOYOBO), 4 μl of the above amplified fragment was ligated with 5 ng of pCR-blunt vector (manufactured by Invitrogen), and DH5α was transformed by using 2 μl of the reaction solution. Plasmid DNA samples were isolated from the obtained several kanamycin-resistant colonies, and about 100 ng thereof was digested with EcoRI and then subjected to agarose gel electrophoresis to confirm the presence of insert. A nucleotide sequence of the cloned PCR amplification fragment was determined by using DNA Sequencer 377 (manufactured by Perkin Elmer) and Big Dye Terminator Cycle Sequencing FS Ready Reaction Kit (manufactured by Perkin Elmer). The sequence of Chinese hamster GDP-fucose transporter cDNA determined by this method is represented by SEQ ID NO:1. A Chinese hamster GDP-fucose transporter amino acid sequence (365 amino acids) deduced from the ORF (nucleotides at positions 117 to 1214) present in the determined full length cDNA sequence is represented by SEQ ID NO:2.

Example 3

Preparation of siRNA Expression Plasmid-Introduced Cell and Preparation of Antibody Composition Using the Cell Targeting GDP-Fucose Transporter 1. Construction of siRNA Expression Plasmid U6_GFT_H_Puro Targeting GDP-Fucose Transporter (1) Selection of Nucleotide Sequence of CHO-Derived Gene as Target of RNAi The 19 nucleotides represented by SEQ ID NO:16 was used as the target sequence of RNAi. The sequence corresponds to positions 803 to 821 in the nucleotide sequence of the Chinese hamster-derived GDP-fucose transporter cDNA derived from Chinese hamster (SEQ ID NO:1) obtained in Example 2. Short interfering RNA (hereinafter referred to as "siRNA") targeting the sequence is named siRNA_GFT_H. Herein, a method for constructing a plasmid U6_GFT8_H_puro expressed siRNA_GFT_H in animal cells is described below. Also, the basic structure of the expression plasmid was designed according to the method of Miyagishi [*Nat. Biotechnology*, 20, 5 (2002)].

(2) Construction of Plasmid U6_Pre_Sense

Figure 5:
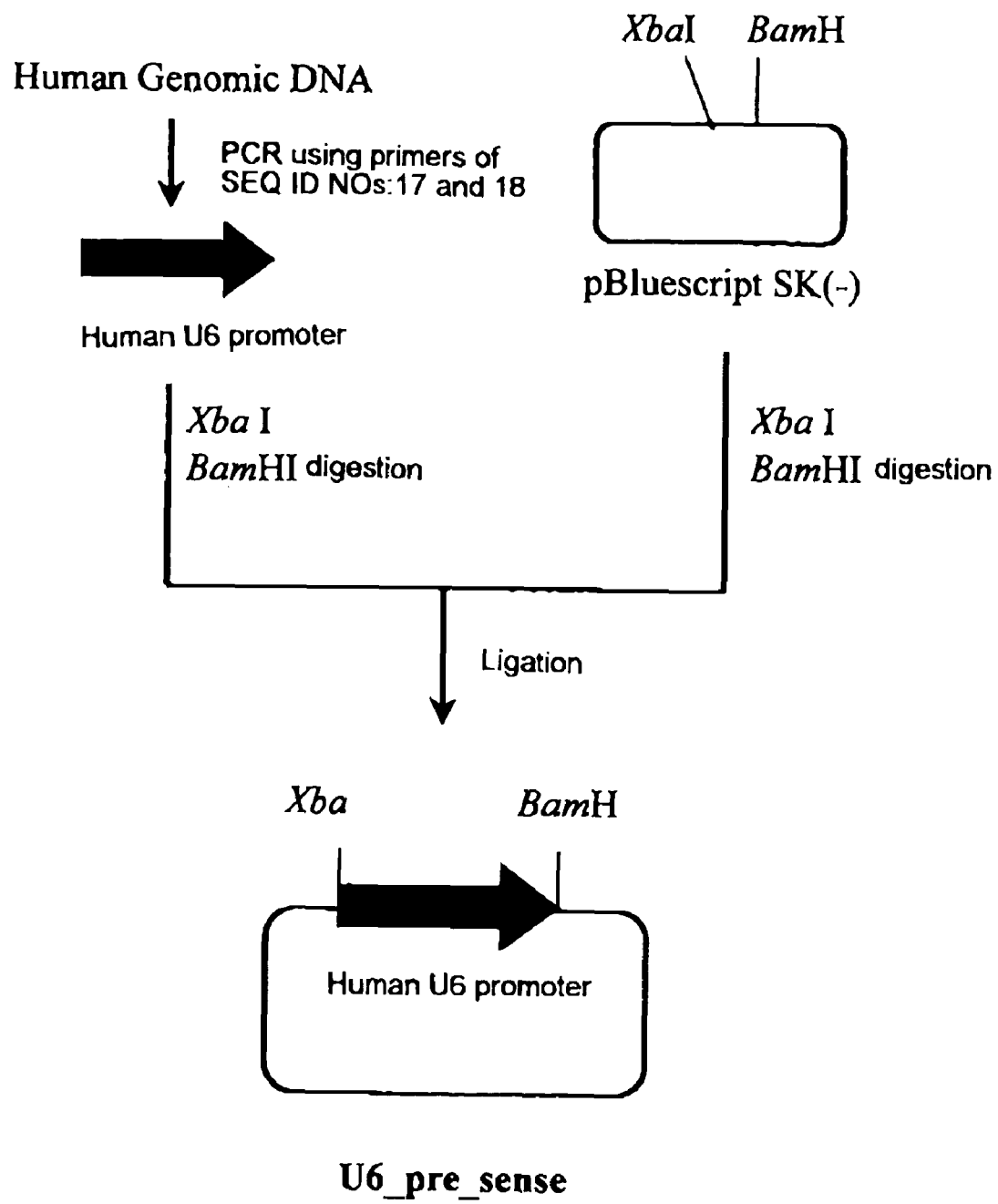
FIG. 5 shows construction steps of plasmid U6_pre_sense.

Plasmid U6_Pre_Sense was constructed according to the following method (FIG. 5). A polymerase chain reaction (PCR) was carried out by using primers (SEQ ID NOs:17 and 18) designed from the gene sequence of human U6 snRNP registered in GenBank (GenBank Nos. X07425 and M14486) to amplify the promoter region of the human U6 snRNP gene. In the PCR, 50 μL of a reaction solution containing 200 ng of Human Genomic DNA (manufactured by Clontech) [1×EX Taq Buffer (manufactured by Takara Shuzo), 0.2 mM dNTP's, 2.5 unit of EX Taq polymerase (manufactured by Takara Shuzo), and 0.5 μM each of the above primers (SEQ ID NOs:65 and 66 as described above)] was prepared, followed by heating at 94° C. for 5 minutes and 30 cycles of heating at 94° C. for 1 minute and 68° C. for 2 minutes as one cycle by using GeneAmp PCR system 9700 (manufactured by Perkin Elmer).

The PCR solution was extracted with phenol/chloroform, and the PCR amplified fragment was recovered by ethanol precipitation. The amplified fragment was digested with XbaI (manufactured by Takara Shuzo), extracted with phenol/chloroform, and subjected to ethanol precipitation to recover a DNA fragment. The DNA fragment was then digested with BamHI (manufactured by Takara Shuzo), and the reaction mixture was subjected to agarose gel electrophoresis. The DNA fragment of about 300 bp was purified by Gel Extraction Kit (manufactured by Qiagen). The recovered DNA fragment was linked with pBluescript SK(−) vector (STRATAGENE) which had been digested in advance with XbaI (manufactured by Takara Shuzo) and BamHI (manufactured by Takara Shuzo) by using DNA Ligation Kit (manufactured by Takara Shuzo). Using the resulting recombinant plasmid DNA, *Escherichia coli* DH5α strain (manufactured by Toyobo) was transformed according to the method of Cohen et al. [*Proc. Natl. Acad. Sci. USA.*, 69, 2110 (1972)] (hereinafter, this method was used in transformation of *Escherichia coli*). A recombinant plasmid DNA was isolated from the resulting multiple ampicillin resistant colonies by using QIAprep Spin Miniprep Kit (manufactured by Qiagen). The nucleotide sequence of U6 promoter contained in the plasmid was determined by using DNA sequencer ABI PRISM 377 (manufactured by Perkin Elmer) according to the conventional method. The plasmid in which no mutation was occurred in the nucleotides during the PCR was selected and named U6_pre_sense.

(3) Construction of Plasmid pBS_BglII

Figure 6:
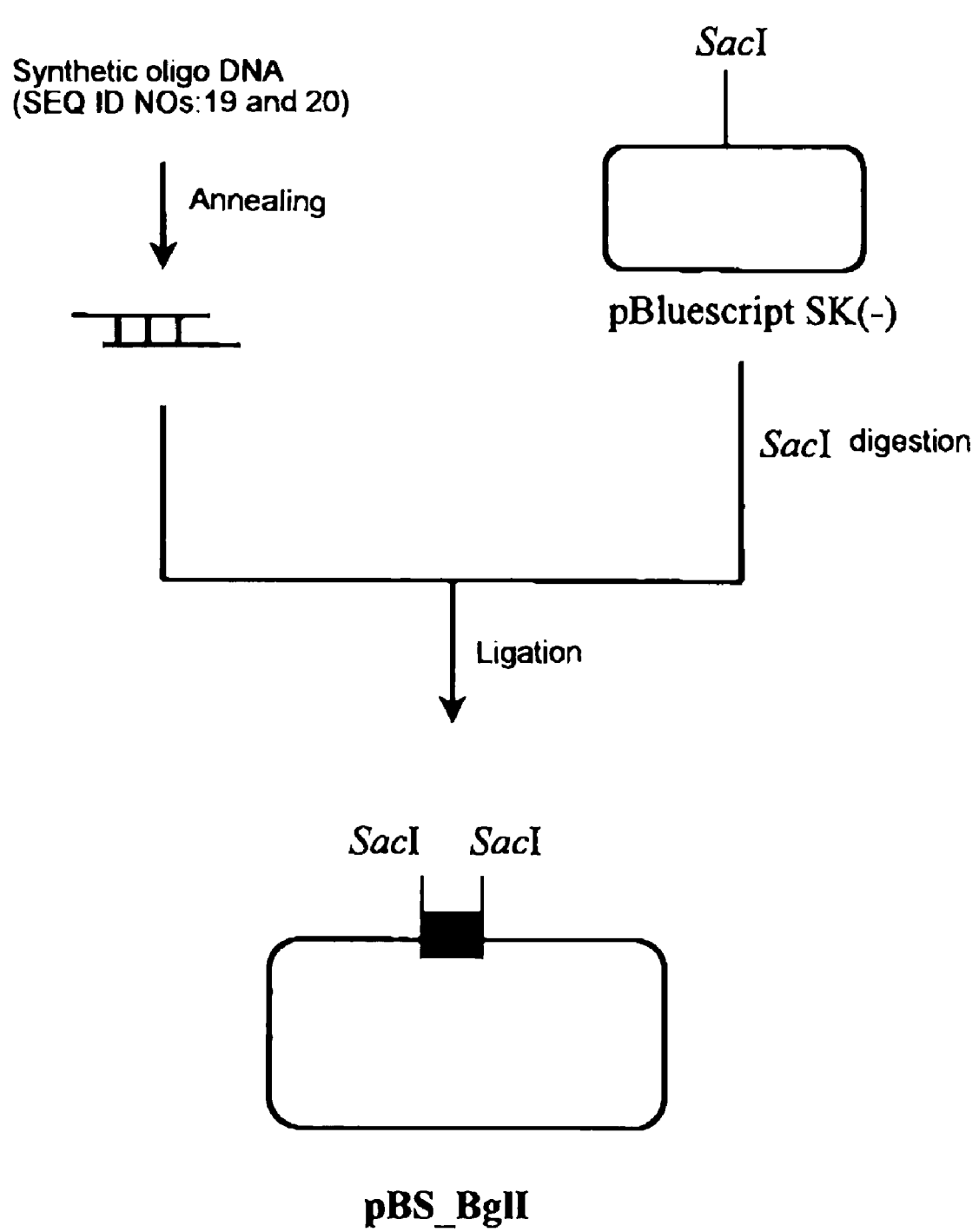
FIG. 6 shows construction steps of plasmid pBS_BglII.

Plasmid pBS_BglII was constructed according to the following method (FIG. 6). In distilled water, 10 pmol of synthetic oligo DNAs (each phosphorylated at the 5' terminals) represented by SEQ ID NOs:19 and 20 was dissolved, followed by heating at 90° C. for 10 minutes, and the mixture was allowed to stand to room temperature for annealing. The annealed synthetic oligomer (0.2 pmol) isolated from the reaction solution was linked with pBluescript SK(−) vector (manufactured by STRATAGENE) which had been digested in advance with SacI (manufactured by Takara Shuzo) by using DNA Ligation Kit (manufactured by Takara Shuzo). *Escherichia coli* DH5α strain (manufactured by Toyobo) was transformed with the resulting recombinant plasmid DNA. The recombinant plasmid DNA was isolated from the resulting multiple ampicillin-resistant colonies by using QIAprep Spin Miniprep Kit (manufactured by Qiagen). The plasmid which was digested with BglII (manufactured by Takara Shuzo) was selected from the respective clones and named pBS_BglII.

(4) Construction of Plasmid U6_Pre_Antisense

Figure 7:
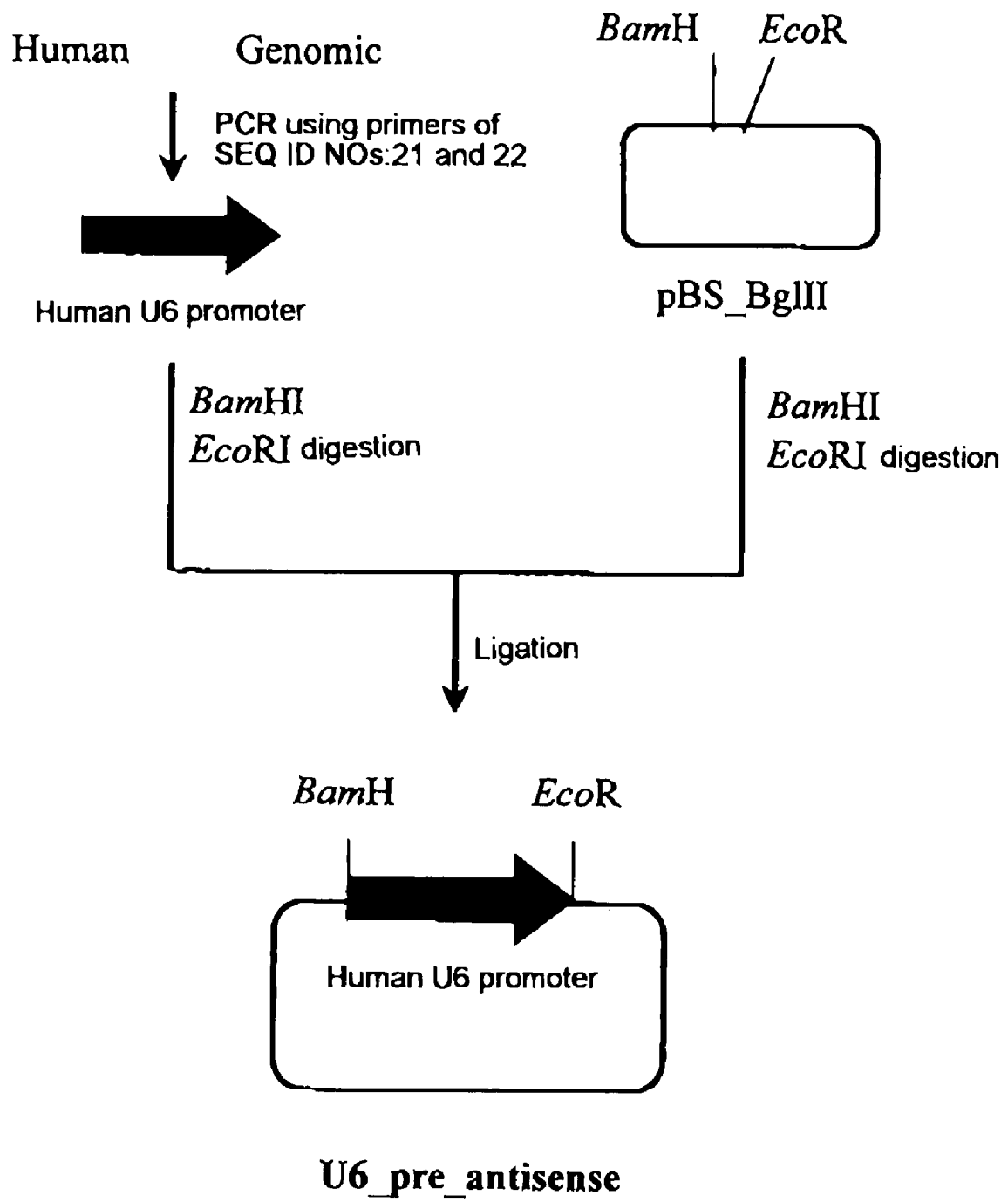
FIG. 7 shows construction steps of plasmid U6_pre_antisense.

Plasmid U6_pre_antisense was constructed according to the following method (FIG. 7). A polymerase chain reaction (PCR) was carried out by using primers (SEQ ID NOs:21 and 22) designed from the gene sequence of human U6 snRNP registered in GenBank (GenBank Accession Nos. X07425 and M14486) to amplify the promoter region of the human U6 snRNP gene. In the PCR, 50 μL of a reaction solution containing 200 ng of Human Genomic DNA (manufactured by Clontech) [1×EX Taq Buffer (manufactured by Takara Shuzo), 0.2 mM dNTP's, 2.5 unit of EX Taq polymerase (manufactured by Takara Shuzo), and 0.5 μM each of the above primers (SEQ ID NOs:21 and 22 as described above)] was prepared, followed by heating at 94° C. for 5 minutes and then 30 cycles of heating at 94° C. for 1 minute and 68° C. for 2 minutes as one cycle by using GeneAmp PCR system 9700 (manufactured by Perkin Elmer)

The PCR solution was extracted with phenol/chloroform, and the PCR amplified fragment was recovered by ethanol precipitation. The amplified fragment was digested with BamHI (manufactured by Takara Shuzo), extracted with phenol/chloroform, and subjected to ethanol precipitation to recover a DNA fragment. The DNA fragment was then digested with EcoRI (manufactured by Takara Shuzo), and the reaction mixture was subjected to agarose gel electrophoresis. The DNA fragment of about 300 bp was purified by using Gel Extraction Kit (manufactured by Qiagen). The recovered DNA fragment was linked with plasmid pBS_B-gIII (manufactured by Takara Shuzo) which had been digested in advance with BamHI (manufactured by Takara Shuzo) and EcoRI (manufactured by Takara Shuzo) by using DNA Ligation Kit (manufactured by Takara Shuzo). *Escherichia coli* DH5α strain (manufactured by Toyobo) was transformed with the resulting recombinant plasmid DNA. The recombinant plasmid DNA was isolated from the resulting multiple ampicillin resistant colonies by using a QIAprep Spin Miniprep Kit (manufactured by Qiagen). The nucleotide sequence of U6 promoter contained in the plasmid was determined by using DNA sequencer ABI PRISM 377 (manufactured by Perkin Elmer) according to the conventional method. The plasmid in which no mutation was occurred in the nucleotides during the PCR was selected from the determined clones and named U6_pre_antisense.

(5) Construction of a Plasmid U6_Sense_H

Figure 8:
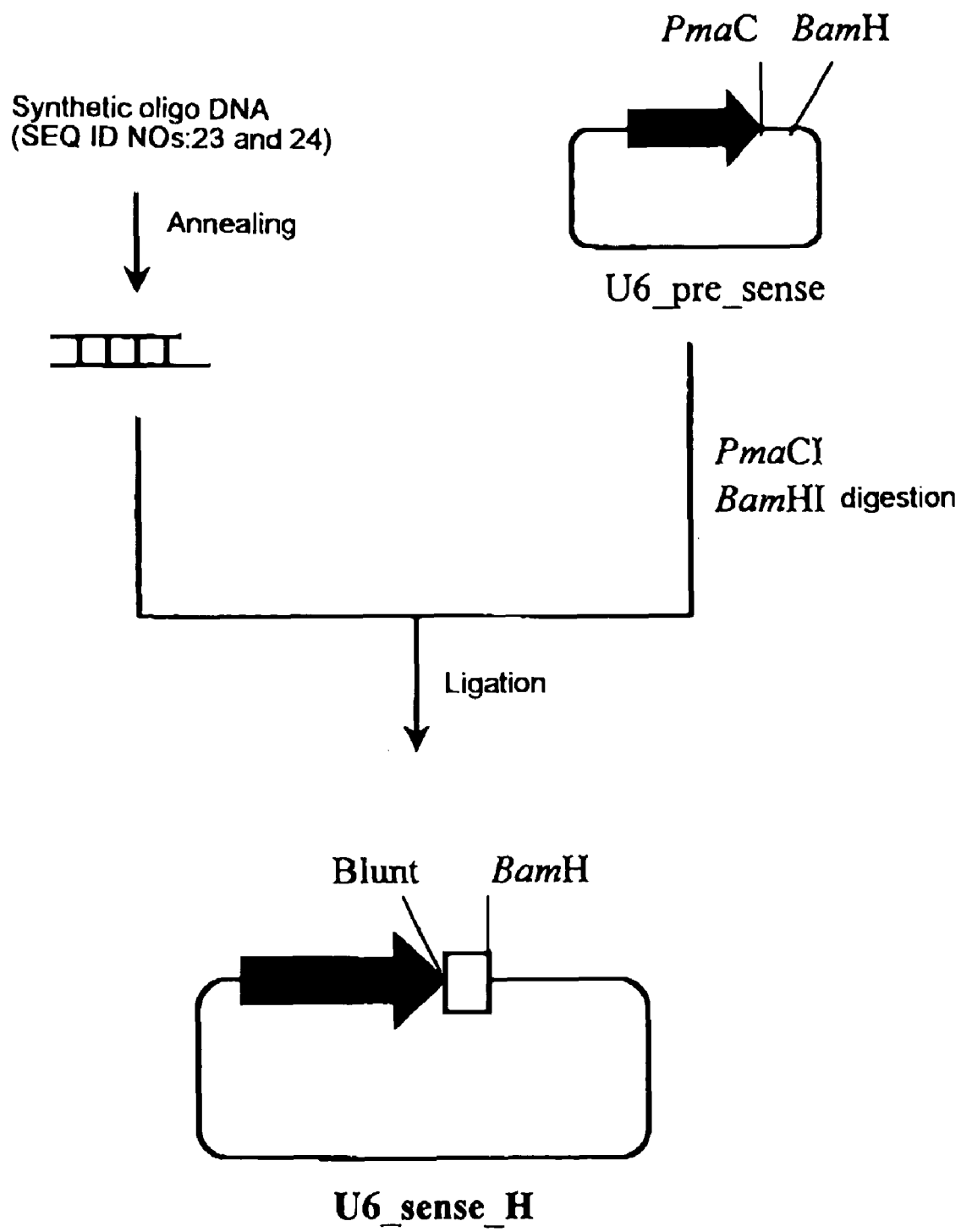
FIG. 8 shows construction steps of plasmid U6_sense_H.

Plasmid U6_sense_B was constructed according to the following method (FIG. 8). In distilled water, 10 pmol of each of synthetic oligo DNAs (each phosphorylated at the 5' terminal) represented by SEQ ID NOs:23 and 24 was dissolved, followed by heating at 90° C. for 10 minutes, and the mixture was allowed to stand to room temperature for annealing. The annealed synthetic oligomer (0.2 pmol) isolated from the reaction solution was linked with a plasmid U6_pre_sense which had been digested in advance with PmaCI (manufactured by Takara Shuzo) and BamHI (manufactured by Takara Shuzo) by using DNA Ligation Kit (manufactured by Takara Shuzo). *Escherichia coli* DH5α strain (manufactured by Toyobo) was transformed with the resulting recombinant plasmid DNA. A recombinant plasmid DNA was isolated from the resulting multiple ampicillin resistant colonies by using QIAprep Spin Miniprep Kit (manufactured by Qiagen). The nucleotide sequence derived from the synthetic oligomer contained in the plasmid was determined by using DNA sequencer ABI PRISM 377 (manufactured by Perkin Elmer) according to the conventional method. The plasmid into which the nucleotide sequences represented by SEQ ID NOs: 23 and 24 were correctly introduced was selected from the determined clones and named U6_sense_H.

(6) Construction of Plasmid U6_Antisense_H

Figure 9:
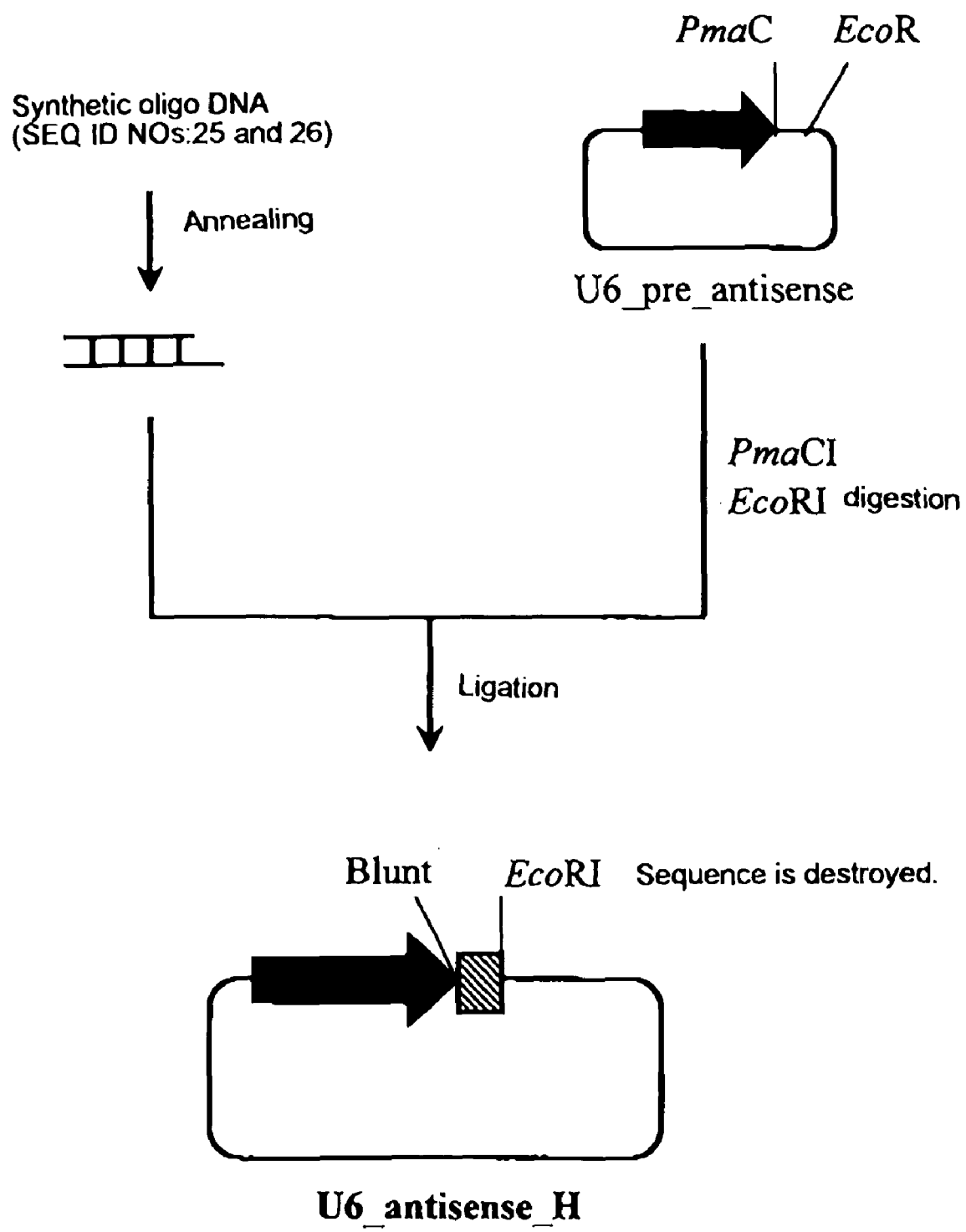
FIG. 9 shows construction steps of plasmid U6_antisense_H.

Plasmid U6_antisense_B was constructed according to the following method (FIG. 9). In distilled water, 10 pmol of each of synthetic oligo DNAs (each phosphorylated at the 5' terminals) represented by SEQ ID NOs:25 and 26 was dissolved, followed by heating at 90° C. for 10 minutes, and the mixture was allowed to cool to room temperature for annealing. The annealed synthetic oligomer (0.2 pmol) isolated from the reaction solution was linked with plasmid U6_pre_antisense which had been digested in advance with PmaCI (manufactured by Takara Shuzo) and EcoRI (manufactured by Takara Shuzo) by using DNA Ligation Kit (manufactured by Takara Shuzo). *Escherichia coli* DH5α strain (manufactured by Toyobo) was transformed with the resulting recombinant plasmid DNA. The recombinant plasmid DNA was isolated from the resulting multiple ampicillin resistant colonies by using QIAprep Spin Miniprep Kit (manufactured by Qiagen). The nucleotide sequence derived from the synthetic oligomer contained in the plasmid was determined by using DNA sequencer ABI PRISM 377 (manufactured by Perkin Elmer) according to the conventional method. The plasmid into which the nucleotide sequences represented by SEQ ID NOs:25 and 26 were correctly introduced was selected from the determined clones and named U6_antisense_H.

(7) Construction of Plasmid U6_GFT_H

Figure 10:
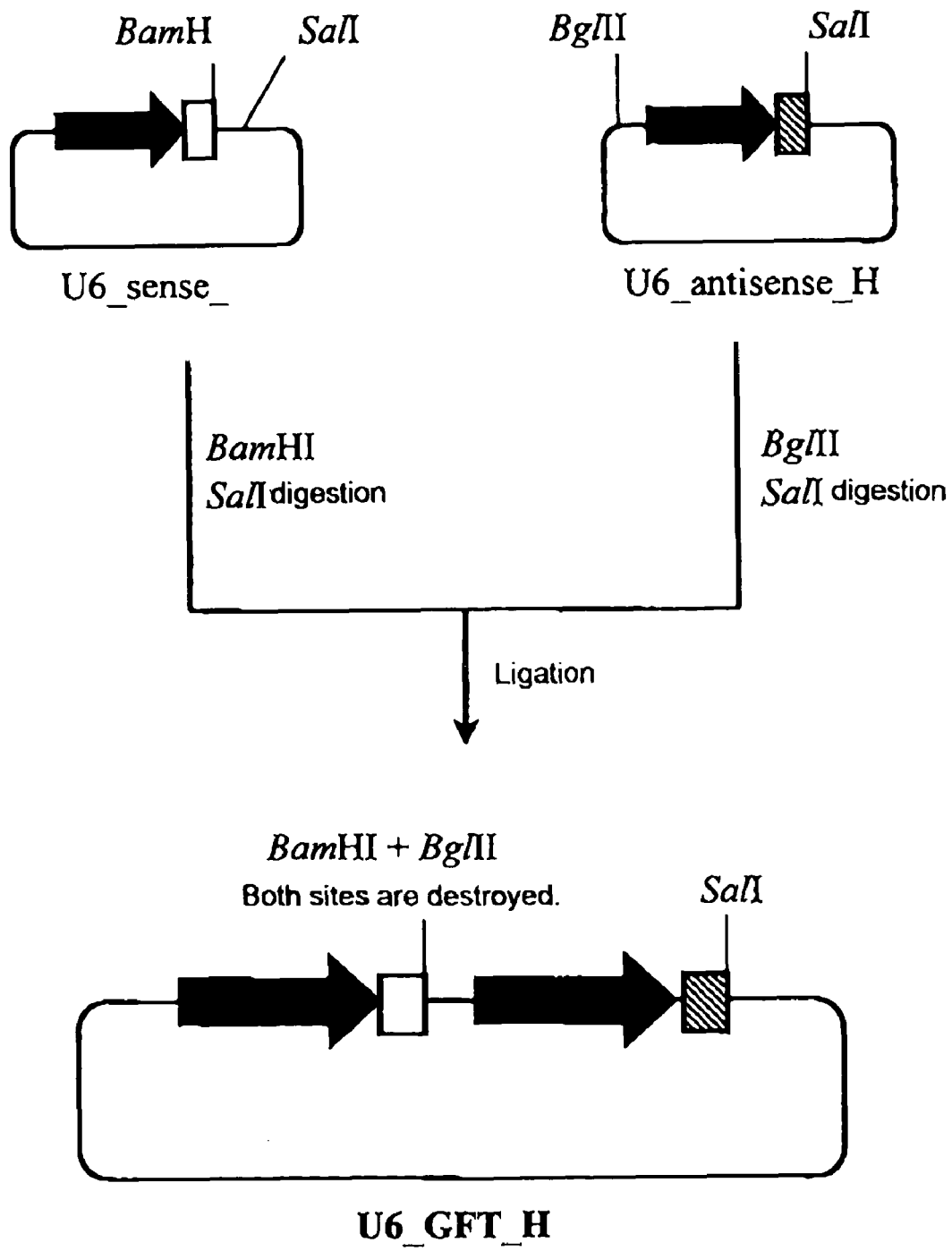
FIG. 10 shows construction steps of plasmid U6_GFT_H.

Plasmid U6_GFT_H was constructed according to the following method (FIG. 10). Plasmid U6_antisense_H was digested with SalI (manufactured by Takara Shuzo) and extracted with phenol/chloroform. The DNA fragment was recovered by ethanol precipitation and then digested with BglII (manufactured by Takara Shuzo). The reaction solution was subjected to agarose gel electrophoresis and the DNA fragment of about 370 bp was purified by using Gel Extraction Kit (manufactured by Qiagen). The recovered DNA fragment was linked with plasmid U6_sense_H which had been digested in advance with SalI (manufactured by Takara Shuzo) and BamHI (manufactured by Takara Shuzo) by using DNA Ligation Kit (manufactured by Takara Shuzo). *Escherichia coli* DH5α strain (manufactured by Toyobo) was transformed with the resulting recombinant plasmid DNA. The recombinant plasmid DNA was isolated from the resulting multiple ampicillin resistant colonies by using QIAprep Spin Miniprep Kit (manufactured by Qiagen). The nucleotide sequence contained in the plasmid was determined by using DNA sequencer ABI PRISM 377 (manufactured by Perkin Elmer) according to the conventional method. The plasmid having the nucleotide sequence of interest was selected from the determined clones and named U6_GFT_H.

(8) Construction of Plasmid U6_FUT8_H_Puro

Figure 11:
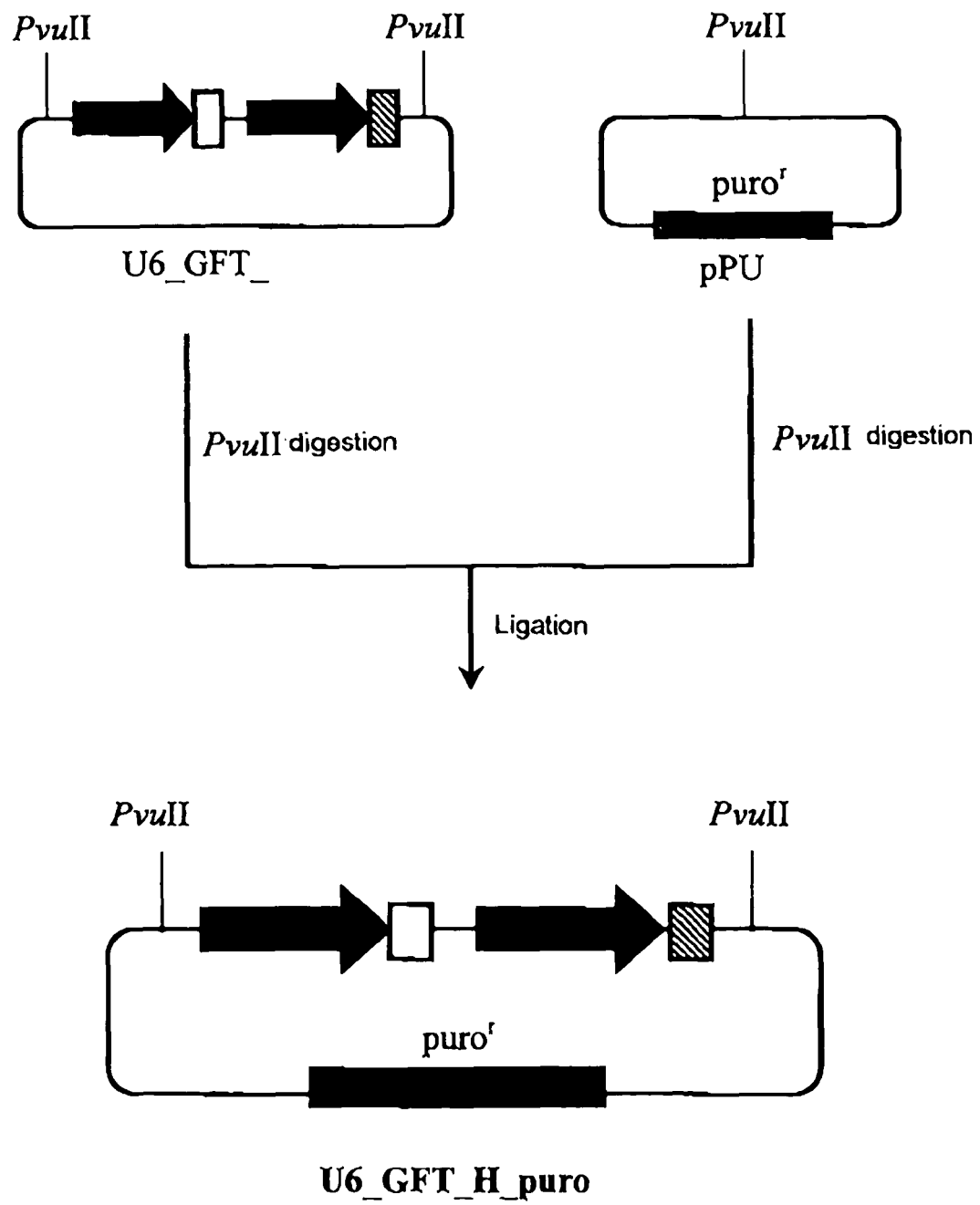
FIG. 11 shows construction steps of plasmid U6 GFT_H_puro.

Plasmid U6_FUT8_H_puro was constructed according to the following method (FIG. 11). Plasmid U6_FUT8_H was digested with PvuII (manufactured by Takara Shuzo) and the reaction solution was subjected to agarose gel electrophoresis. The DNA fragment of about 1150 bp was purified by using Gel Extraction Kit (manufactured by Qiagen). The recovered DNA fragment was inserted plasmid pPUR (manufactured by Clontech) which had been digested in advance with PvuII (manufactured by Takara Shuzo) by using DNA Ligation Kit (manufactured by Takara Shuzo). *Escherichia coli* DH5α strain (manufactured by Toyobo) was transformed with the resulting recombinant plasmid DNA. The recombinant plasmid DNA was isolated from the resulting multiple ampicillin resistant colonies by using QIAprep Spin Miniprep Kit (manufactured by Qiagen). The nucleotide sequence contained in the plasmid was determined by using DNA sequencer ABI PRISM 377 (manufactured by Perkin Elmer) according to the conventional method. The plasmid having the nucleotide sequence of interest was selected from the determined clones and named U6_FUT8_H_puro.

(9) Preparation of Linearized Plasmid U6_GFT_H_Puro

Plasmid U6_GFT_H_puro was digested with a restriction enzyme FspI (manufactured by NEW ENGLAND BIOLABS) for linearization. After the digestion, the reaction solution was subjected to agarose gel electrophoresis to confirm that the plasmids were correctly linearized.

2. Preparation of Lectin-Resistant Clone into Which GDP-Fucose Transporter siRNA Expression Plasmid has Been Introduced (1) Preparation of anti-CCR4 Chimeric Antibody-Producing Cell Using CHO/DG44 Cell as the Host After introducing 4 μg of the anti-CCR4 chimeric antibody expression vector pKANTEX2160 into $1.6 \times 10^6$ cells of CHO/DG44 cell by electroporation [*Cytotechnology*, 3, 133

(1990)], the cells were suspended in 10 ml of IMDM-dFBS (10)—HT(1) [IMDM medium (manufactured by Invitrogen) comprising 10% dFBS (manufactured by Invitrogen) and 1×concentration of HT supplement (manufactured by Invitrogen)] and dispensed at 100 μl/well into a 96 well culture plate (manufactured by Asahi Techno Glass). After culturing at 37° C. for 24 hours in a 5% $CO_2$ incubator, the medium was changed to IMDM-dFBS(10) (IMDM medium comprising 10% of dialyzed FBS, followed by culturing for 1 to 2 weeks. Culture supernatant was recovered from wells in which the growth was observed due to formation of transformant colony, and the concentration of the anti-CCR4 chimeric antibody in the supernatant was measured by the ELISA described in the item (6) of Example 1 using a CCR4 peptide-immobilized plate.

In order to increase an amount of the antibody production using a DHFR gene amplification system, each of the transformants in wells in which production of the anti-CCR4 chimeric antibody was observed in culture supernatants was suspended in the IMDM-dFBS(10) medium comprising 50 nM MTX to give a density of 1 to $2 \times 10^5$ cells/ml, and the suspension was dispensed at 0.5 ml into wells of a 24 well plate (manufactured by Asahi Techno Glass). After culturing at 37° C. for 1 to 2 weeks in a 5% $CO_2$ incubator, transformants showing 50 nM MTX resistance were induced. For the transformants in wells in which the growth was observed, the MTX concentration was increased to 200 nM by the same method, and a transformant capable of growing in the IMDM-dFBS(10) medium comprising 200 nM MTX and of producing the anti-CCR4 chimeric antibody in a large amount was finally obtained. The obtained transformant was suspended in the IMDM-dFBS(10) medium comprising 500 nM MTX to give a density of 0.5 cell/well, and inoculated into wells of a 96 well plate (manufactured by Asahi Techno Glass) to carrying out single cell separation by limiting dilution. After culturing at 37° C. for 2 weeks, each plate was observed with a microscope, and a well in which growth of single colony was confirmed was subjected to scale-up culturing to thereby obtain a clone expressing an anti-CCR4 chimeric antibody, clone 32-05-09.

(2) Introduction of siRNA Expression Vector U6_GFT_H_puro into anti-CCR4 Chimeric Antibody-Producing Cell The siRNA expression vector constructed in Example 1 was introduced into the clone 32-05-09 prepared in the item (1) of this Example.

The introduction of the siRNA expression vector into the clone 32-05-09 was carried out by electroporation [*Cytotechnology*, 3, 133 (1990)] according to the following method. First, the clone 32-05-09 was suspended into Dulbecco's PBS (K-PBS buffer) (137 mmol KCl, 2.7 mmol/l NaCl, 8.1 mmol/l $Na_2HPO_4$, 1.5 mmol/l $KH_2PO_4$, 4.0 mmol/l $MgCl_2$) at $8 \times 10^6$ cells/ml, and 200 μl of the cell suspension ($1.8 \times 10^6$ cells) was mixed with 10 μg of the linearized plasmid prepared in the item 1 of this Example. The resulting cell/DNA mixture was moved into Gene Pulser Cuvette (2 mm in distance between the electrodes) (manufactured by BIO-RAD) and subjected to gene introduction at 0.35 KV of pulse voltage and 250 μF of electric capacity on a cell fusion apparatus, Gene Pulser (manufactured by BIO-RAD).

The cell suspension was added to 30 ml of a basic medium [Iscove's Modified Dulbecco's Medium (manufactured by Life Technologies) supplemented with 10% fetal bovine dialyzed serum (manufactured by Life Technologies) and 50 μg/ml gentamicin (manufactured by Nacalai Tesque)] and then inoculated at 10 ml on a 10 cm dish for cell adhesion (manufactured by Asahi Techno Glass) and cultured in 5% $CO_2$ at 37° C. for 24 hours. After removal of the culture medium, 10 ml of a basic medium supplemented with 12 μg/ml puromycin (manufactured by SIGMA) was added thereto. After further culturing for 6 days, the culture medium was aspirated, and then a basic medium supplemented with 0.5 mg/ml LCA (*Lens culinaris* agglutinin) (manufactured by Vector) and 12 μg/ml puromycin (manufactured by SIGMA) was added thereto at 100 μl/well. After further culturing for 10 days, the survival clone was isolated. Also, expression of the anti-CCR4 chimeric antibody in the culture supernatant of these survival clones was confirmed by the ELISA described in the item (6) of Example 1 using a CCR4 peptide-immobilized plate.

The resulting clone was removed from the culture plate by trypsin treatment, inoculated on a 24 well plate for tissue culture (manufactured by Asahi Techno Glass) and cultured with a basic medium supplemented with 12 mg/ml puromycin (manufactured by SIGMA) for 5 days. After culturing, each clone in each well of the plate was scale-up cultured on a basic medium supplemented with 12 μg/ml puromycin (manufactured by SIGMA) in a flask for tissue culture (manufactured by Asahi Techno Glass). One clone of the thus obtained clones into which the siRNA expression vector U6_GFT_H_puro was introduced was named clone 32-05-09-H12. The clone 32-05-09-H12 has been deposited in the names of clone 32-05-09-H12 on Mar. 27, 2003 as FERM BP-8345 in International Patent Organism Depositary, National Institute of Advanced Industrial Science and Technology (Tsukuba Central 6, 1, Higashi I-Chome Tsukuba-shi, Ibaraki-ken, Japan).

3. Measurement of GDP-Fucose Transporter mRNA in siR-NA_GFT_H-Introduced Clone Targeting GDP-Fucose Transporter The clone 32-05-09-H12 obtained in the item 2 of this Example was suspended in a basic medium supplemented with 12 μg/ml puromycin at a cell density of $3 \times 10^5$ cells/ml, inoculated in a T75 flask for adhesion cells (manufactured by Greiner), and cultured for 3 days. Each cell suspension was recovered by trypsin treatment and centrifuged at 12,000 rpm at 4° C. for 5 minutes to remove the supernatant. The cells were suspended in Dulbecco's PBS (manufactured by GIBCO), centrifuged again at 12,000 rpm at 4° C. for 5 minutes, and then frozen at −80° C. The parent clone 32-05-09 in which the siRNA expression plasmid was not introduced was also treated in the same manner to prepare the frozen cells.

The frozen cells were thawed at room temperature and the total RNA was extracted by using RNAeasy (manufactured by Qiagen) according to the attached manufacture's instruction. The total RNA was dissolved in 45 μl of sterilized water, 1 μl of RQ1 RNase-Free DNase (manufactured by Promega), 5 μl of the attached 10×DNase buffer and 0.5 μl of RNasin ribonuclease inhibitor (manufactured by Promega) were added thereto, and the mixture was allowed to react at 37° C. for 30 minutes to decompose genomic DNA contaminated in the sample. After the reaction, the total RNA was purified again by using RNAeasy (manufactured by Qiagen) and dissolved in 40 μl of sterilized water.

For 3 μg of each of the obtained total RNAs, a reverse transcription reaction was carried out by using oligo(dT) as a primer in a 20 μl system with SUPERSCRIPT™ Preamplification System for First Strand cDNA Synthesis (manufactured by Life Technologies) according to the attached manufacture's instruction to synthesize a single-strand cDNA.

Next, PCR was carried out by using a 100-folds diluted cDNA solution as the template with primer sets h_GFT_fw4 (SEQ ID NO:27) and h_GFT_rv2 (SEQ ID NO:28) which were designed so as to amplify the region of nucleotides at positions 799 to 1108 of Chinese hamster GDP-fucose transporter cDNA represented by SEQ ID NO:1. Specifically, 20 μl of a reaction solution [1×Ex Taq Buffer (manufactured by Takara Shuzo), 0.2 mM dNTP's, 2.5 units of Ex Taq polymerase hot start version (manufactured by Takara Shuzo) and 0.5 μM of the above primers (SEQ ID NOs: 27 and 28)] was prepared, and the PCR was carried out by heating at 94° C. for 3 minutes and 32 cycles of heating at 94° C. for 1 minute, 60° C. for 1 minute and 72° C. for 2 minutes as one cycle. After 7 μl of the PCR solution was subjected to 1.75% agarose gel electrophoresis, the gel was immersed in a 1×concentration SYBR Gold Nucleic Acid Gel Stain (manufactured by Molecular Probes) for staining for 30 minutes. The amount of the DNA amplified by the PCR was measured by a fluoroimager (FluorImager; manufactured by Molecular Dynamics) and compared with the expression amount of mRNA in the GDP-fucose transporter. Furthermore, the expression amount of mRNA in β-actin was measured and compared by using the linearized cDNA at the same amount as the linearized cDNA used as the template in the measurement of the amount of mRNA in the GDP-fucose transporter according to the method for determining the transcription amount by competitive PCR as described in WO00/61739.

FIG. 12 shows the results of the comparison of the mRNAs of the GDP-fucose transporter and β-action expressed in the clone 32-05-09 and the clone 32-05-09-H12 by the above method. The results show that in the PCR independently carried out three times, there was no difference of the amount of mRNA in β-action between the two compared clones, whereas the expression amount of mRNA in the GDP-fucose transporter was significantly decreased.

4. Preparation of Antibody Composition Produced by siRNA Expression Plasmid-Introduced Clone Targeting GDP-Fucose Transporter An anti-CCR4 chimeric antibody produced by the obtained clone 32-05-09-H12 and clone 32-05-09 was prepared according to the following method.

The clone 32-05-09-H12 was suspended in a basic medium supplemented with 12 μg/ml puromycin at a density of 3×10⁵ cells/ml, and 30 ml of the mixture was inoculated in a T182 flask for culturing adhesion cell (manufactured by Greiner) and cultured to become 100% confluent. The clone 32-05-09 was cultured in the same manner in the above, except for using a basic medium which was not supplemented with puromycin. A whole amount of the medium was removed in each clone, the same amount of PBS (manufactured by Invitrogen) was added and removed again for washing, and the medium was replaced with 30 ml of EXCELL301 (manufactured by JRH Biosciences). After culturing for further 7 days, each of the cell suspensions was recovered. The suspension was centrifuged at 3,000 rpm and 4° C. for 10 minutes to recover the supernatant, followed by filtration through PES Membrane of 0.22 mm pore size (manufactured by Asahi Techno Glass).

In a column of 0.8 cm diameter, 0.5 ml of Mab Select (manufactured by Amersham Pharmacia Biotech) was packed, and 3.0 ml of purified water and 3.0 ml of 0.2 mol/L borate-0.15 mol/L NaCl buffer (pH 7.5) were successively passed in the column. The column was further washed successively with 2.0 ml of 0.1 mol/l citrate buffer (pH 3.5) and 1.5 ml of 0.2 mol/borate0.15 mol/l NaCl buffer (pH 7.5) to equilibrate the carrier. Then, 30 ml of the culture supernatant after the above filtration was applied to the column, and then the column was washed with 3.0 ml of 0.2 mol/l borate-0.15 mol/l NaCl buffer (pH 7.5). After washing, the antibody adsorbed on the column was eluted with 1.25 ml of 0.1 mol/l citrate buffer (pH 3.5). A fraction of 250 μl first eluted was discarded, and 1 ml of the next fraction was recovered and neutralized with 0.2 ml of 2 mol/l Tris-HCl (pH 8.5). The recovered eluate was dialyzed in 10 mol/l citrate-0.15 mol/l NaCl buffer (pH 6.0) at 4° C. overnight. After the dialysis, the antibody solution was recovered and subjected to sterile filtration by using Millex GV of 0.22 mm pore size (manufactured by MILLIPORE).

5. Monosaccharide Composition Analysis in Antibody Composition Produced by siRNA Expression Plasmid-Introduced Clone Targeting GDP-Fucose Transporter For the anti-CCR4 humanized antibody purified in the item 4 of this Example, the monosaccharide composition analysis was carried out according to a known method [*Journal of Liquid Chromatography*, 6, 1577 (1983)]. Table 3 shows the ratio of fucose-free complex sugar chains in the total complex sugar chains, calculated from the monosaccharide composition ratio contained in each of the antibodies. The results show that the ratio of the fucose-free sugar chains in the antibodies produced by the parent clones 32-05-09 used in the siRNA introduction was 8%, whereas the ratio in the siRNA-introduced stain 32-05-09-H12 was significantly increased up to 56%.

From the above results, it was shown that the introduction of siRNA targeting GDP-fucose transporter can control fucose modification of complex sugar chains in the antibody produced by a host cell.

6. Biological Activity of Antibody Composition Produced by siRNA Expression Plasmid-Introduced Clone Targeting GDP-Fucose Transporter The biological activity of the anti-CCR4 chimeric antibody purified in the item 4 of this Example 4 was measured according to the measuring method of ADCC activity described in the item (7) of Example 1 and the antigen binding activity described in the item (6) of Example 1. The results are shown in Table 3. It was observed that there was no difference in antigen binding activity between the antibody produced by the parent clone 32-05-09 and the antibody produced by the siRNA-introduced clone 32-05-09-H12, whereas it was confirmed that the ADCC activity of the antibody produced by the siRNA-introduced clone 32-05-09-H12 was markedly increased.

TABLE 3

| Ratio of fucose-free sugar chains of antibody produced by each clone | |
|---|---|
| Strain | Ratio of fucose-free sugar chain |
| 32-05-09 | 8% |
| 32-05-09-H12 | 56% |

While the invention has been described in detail and with reference to specific embodiments thereof, it will be apparent to one skill in the art that various changes and modifications can be made therein without departing from the spirit and scope thereof. All references cited herein are incorporated in their entirety.

This application is based on Japanese application No. 2002-106952 filed on Apr. 9, 2002, the entire contents of which being incorporated hereinto by reference.

What is claimed is:

1. An isolated cell in which the activity of a GDP-fucose transporter is deleted by a gene disruption technique which comprises targeting a gene encoding a GDP-fucose transporter, wherein the gene encoding the GDP-fucose transporter is a DNA comprising the nucleotide sequence of SEQ ID NO:1.

2. An isolated cell in which the activity of a GDP-fucose transporter is deleted by a gene disruption technique which comprises targeting a gene encoding a GDP-fucose transporter, wherein the GDP-fucose transporter is a protein comprising the amino acid sequence of SEQ ID NO:2.

3. The cell according to claim 1 or claim 2, which is resistant to a lectin which recognizes a sugar chain in which 1-position of fucose is bound to 6-position of N-acetylglucosamine in the reducing end through α-bond in a complex N-glycoside-linked sugar chain.

4. The cell according to claim 3, which is resistant to at least one lectin selected from the group consisting of the following (a) to (d):
   (a) a *Lens culinaris* lectin;
   (b) a *Pisum sativum* lectin;
   (c) a *Vicia faba* lectin;
   (d) an *Aleuria aurantia* lectin.

5. The cell according to claim 1 or claim 2, wherein the cell is an animal cell.

6. An isolated transformed cell in which the activity of a genomic GDP-fucose transporter is deleted, wherein the genomic GDP-fucose transporter is a protein comprising the amino acid sequence of SEQ ID NO:2; and wherein the activity of the genomic GDP-fucose transporter is deleted by an RNA interference (RNAi) method.

7. The cell according to claim 6, wherein the RNAi method uses a nucleotide represented by SEQ ID NO: 16.

8. The cell according to claim 6, which is resistant to a lectin which recognizes a sugar chain in which 1-position of fucose is bound to 6-position of N-acetylglucosamine in the reducing end through α-bond in a complex N-glycoside-linked sugar chain.

9. The cell according to claim 8, which is resistant to at least one lectin selected from the group consisting of the following (a) to (d):
   (a) a *Lens culinaris* lectin;
   (b) a *Pisum sativum* lectin;
   (c) a *Vicia faba* lectin;
   (d) an *Aleuria aurantia* lectin.

10. The cell according to claim 6, wherein the cell is an animal cell.

11. The cell according to claim 10, wherein the animal cell is a CHO cell.

* * * * *

SEQUENCE LISTING

<160> NUMBER OF SEQ ID NOS: 35

<210> SEQ ID NO 1
<211> LENGTH: 1245
<212> TYPE: DNA
<213> ORGANISM: Cricetulus griseus

<400> SEQUENCE: 1

```
gaacttcacc caagccatgt gacaattgaa ggctgtaccc ccagaccta acatcttgga       60
gccctgtaga ccagggagtg cttctggccg tggggtgacc tagctcttct accaccatga    120
acagggcccc tctgaagcgg tccaggatcc tgcgcatggc gctgactgga ggctccactg    180
cctctgagga ggcagatgaa gacagcagga acaagccgtt tctgctgcgg cgctgcagca    240
tcgcgctggt cgtctctctc tactgggtca cctccatctc catggtattc ctcaacaagt    300
acctgctgga cagcccctcc ctgcagctgg atacccctat cttcgtcact ttctaccaat    360
gcctggtgac ctctctgctg tgcaagggcc tcagcactct ggccacctgc tgcctggca    420
ccgttgactt ccccaccctg aacctggacc ttaaggtggc ccgcagcgtg ctgccactgt    480
cggtagtctt cattggcatg ataagtttca ataacctctg cctcaagtac gtaggggtgg    540
ccttctacaa cgtggggcgc tcgctcacca ccgtgttcaa tgtgcttctg tcctacctgc    600
tgctcaaaca gaccacttcc ttctatgccc tgctcacatg tggcatcatc attggtggtt    660
tctggctggg tatagaccaa gagggagctg agggcaccct gtccctcata ggcaccatct    720
tcggggtgct ggccagcctc tgcgtctccc tcaatgccat ctataccaag aaggtgctcc    780
cagcagtgga aacagcatc tggcgcctaa ccttctataa caatgtcaat gcctgtgtgc    840
tcttcttgcc cctgatggtt ctgctgggtg agctccgtgc cctccttgac tttgctcatc    900
tgtacagtgc ccacttctgg ctcatgatga cgctgggtgg cctcttcggc tttgccattg    960
gctatgtgac aggactgcag atcaaattca ccagtcccct gacccacaat gtatcaggca   1020
cagccaaggc ctgtgcgcag acagtgctgg ccgtgctcta ctatgaagag actaagagct   1080
tcctgtggtg gacaagcaac ctgatggtgc tgggtggctc ctcagcctat acctgggtca   1140
ggggctggga gatgcagaag acccaagagg accccagctc caagagggt gagaagagtg   1200
ctattggggt gtgagcttct tcagggacct gggactgaac ccaag                    1245
```

<210> SEQ ID NO 2
<211> LENGTH: 365
<212> TYPE: PRT
<213> ORGANISM: Cricetulus griseus

<400> SEQUENCE: 2

```
Met Asn Arg Ala Pro Leu Lys Arg Ser Arg Ile Leu Arg Met Ala Leu
 1               5                  10                  15

Thr Gly Gly Ser Thr Ala Ser Glu Glu Ala Asp Glu Asp Ser Arg Asn
            20                  25                  30

Lys Pro Phe Leu Leu Arg Ala Leu Gln Ile Ala Leu Val Val Ser Leu
        35                  40                  45

Tyr Trp Val Thr Ser Ile Ser Met Val Phe Leu Asn Lys Tyr Leu Leu
    50                  55                  60

Asp Ser Pro Ser Leu Gln Leu Asp Thr Pro Ile Phe Val Thr Phe Tyr
65                  70                  75                  80

Gln Cys Leu Val Thr Ser Leu Leu Cys Lys Gly Leu Ser Thr Leu Ala
                85                  90                  95
```

```
Thr Cys Cys Pro Gly Thr Val Asp Phe Pro Thr Leu Asn Leu Asp Leu
            100                 105                 110
Lys Val Ala Arg Ser Val Leu Pro Leu Ser Val Val Phe Ile Gly Met
        115                 120                 125
Ile Ser Phe Asn Asn Leu Cys Leu Lys Tyr Val Gly Val Ala Phe Tyr
    130                 135                 140
Asn Val Gly Arg Ser Leu Thr Thr Val Phe Asn Val Leu Leu Ser Tyr
145                 150                 155                 160
Leu Leu Leu Lys Gln Thr Thr Ser Phe Tyr Ala Leu Leu Thr Cys Gly
                165                 170                 175
Ile Ile Ile Gly Gly Phe Trp Leu Gly Ile Asp Gln Glu Gly Ala Glu
            180                 185                 190
Gly Thr Leu Ser Leu Ile Gly Thr Ile Phe Gly Val Leu Ala Ser Leu
        195                 200                 205
Cys Val Ser Leu Asn Ala Ile Tyr Thr Lys Lys Val Leu Pro Ala Val
    210                 215                 220
Asp Asn Ser Ile Trp Arg Leu Thr Phe Tyr Asn Asn Val Asn Ala Cys
225                 230                 235                 240
Val Leu Phe Leu Pro Leu Met Val Leu Leu Gly Glu Leu Arg Ala Leu
                245                 250                 255
Leu Asp Phe Ala His Leu Tyr Ser Ala His Phe Trp Leu Met Met Thr
            260                 265                 270
Leu Gly Gly Leu Phe Gly Phe Ala Ile Gly Tyr Val Thr Gly Leu Gln
        275                 280                 285
Ile Lys Phe Thr Ser Pro Leu Thr His Asn Val Ser Gly Thr Ala Lys
    290                 295                 300
Ala Cys Ala Gln Thr Val Leu Ala Val Leu Tyr Tyr Glu Glu Thr Lys
305                 310                 315                 320
Ser Phe Leu Trp Trp Thr Ser Asn Leu Met Val Leu Gly Gly Ser Ser
                325                 330                 335
Ala Tyr Thr Trp Val Arg Gly Trp Glu Met Gln Lys Thr Gln Glu Asp
            340                 345                 350
Pro Ser Ser Lys Glu Gly Glu Lys Ser Ala Ile Gly Val
        355                 360                 365

<210> SEQ ID NO 3
<211> LENGTH: 1095
<212> TYPE: DNA
<213> ORGANISM: Homo sapiens

<400> SEQUENCE: 3
atgaataggg cccctctgaa gcggtccagg atcctgcaca tggcgctgac cggggcctca      60
gacccctctg cagaggcaga ggccaacggg gagaagccct ttctgctgcg ggcattgcag     120
atcgcgctgg tggtctccct ctactgggtc acctccatct ccatggtgtt ccttaataag     180
tacctgctgg acagcccctc cctgcggctg acaccccca tcttcgtcac cttctaccag      240
tgcctggtga ccacgctgct gtgcaaaggc ctcagcgctc tggccgcctg ctgccctggt     300
gccgtggact ccccagctt cgcctggac ctcaggtgg cccgcagcgt cctgcccctg        360
tcggtggtct tcatcggcat gatcaccttc aataacctct gcctcaagta cgtcggtgtg    420
gccttctaca atgtgggccg ctcactcacc accgtcttca cgtgctgct ctcctacctg      480 ctgctcaagc agaccacctc cttctatgcc ctgctcacct gcggtatcat catcgggggc    540
ttctggcttg gtgtggacca ggagggggca gaaggcaccc tgtcgtggct gggcaccgtc    600
```

```
ttcggcgtgc tggctagcct ctgtgtctcg ctcaacgcca tctacaccac gaaggtgctc    660
ccggcggtgg acggcagcat ctggcgcctg actttctaca acaacgtcaa cgcctgcatc    720
ctcttcctgc ccctgctcct gctgctcggg gagcttcagg ccctgcgtga ctttgcccag    780 ctggcagtg cccacttctg ggggatgatg acgctgggcg gcctgtttgg ctttgccatc     840
ggctacgtga caggactgca gatcaagttc accagtccgc tgacccacaa tgtgtcgggc    900
acggccaagg cctgtgccca gacagtgctg gccgtgctct actacgagga gaccaagagc    960
ttcctctggt ggacgagcaa catgatggtg ctgggcggct cctccgccta cacctgggtc   1020
aggggctggg agatgaagaa gactccggag gagcccagcc ccaaagacag cgagaagagc   1080
gccatggggg tgtga                                                    1095
```

<210> SEQ ID NO 4
<211> LENGTH: 364
<212> TYPE: PRT
<213> ORGANISM: Homo sapiens

<400> SEQUENCE: 4

```
Met Asn Arg Ala Pro Leu Lys Arg Ser Arg Ile Leu His Met Ala Leu
 1               5                  10                  15

Thr Gly Ala Ser Asp Pro Ser Ala Glu Ala Glu Ala Asn Gly Glu Lys
             20                  25                  30

Pro Phe Leu Leu Arg Ala Leu Gln Ile Ala Leu Val Val Ser Leu Tyr
         35                  40                  45

Trp Val Thr Ser Ile Ser Met Val Phe Leu Asn Lys Tyr Leu Leu Asp
     50                  55                  60

Ser Pro Ser Leu Arg Leu Asp Thr Pro Ile Phe Val Thr Phe Tyr Gln
 65                  70                  75                  80

Cys Leu Val Thr Thr Leu Leu Cys Lys Gly Leu Ser Ala Leu Ala Ala
                 85                  90                  95

Cys Cys Pro Gly Ala Val Asp Phe Pro Ser Leu Arg Leu Asp Leu Arg
            100                 105                 110

Val Ala Arg Ser Val Leu Pro Leu Ser Val Val Phe Ile Gly Met Ile
        115                 120                 125

Thr Phe Asn Asn Leu Cys Leu Lys Tyr Val Gly Val Ala Phe Tyr Asn
    130                 135                 140

Val Gly Arg Ser Leu Thr Thr Val Phe Asn Val Leu Leu Ser Tyr Leu
145                 150                 155                 160

Leu Leu Lys Gln Thr Thr Ser Phe Tyr Ala Leu Leu Thr Cys Gly Ile
                165                 170                 175

Ile Ile Gly Gly Phe Trp Leu Gly Val Asp Gln Glu Gly Ala Glu Gly
            180                 185                 190

Thr Leu Ser Trp Leu Gly Thr Val Phe Gly Val Leu Ala Ser Leu Cys
        195                 200                 205

Val Ser Leu Asn Ala Ile Tyr Thr Thr Lys Val Leu Pro Ala Val Asp
    210                 215                 220

Gly Ser Ile Trp Arg Leu Thr Phe Thr Asn Val Asn Ala Cys Ile
225                 230                 235                 240

Leu Phe Leu Pro Leu Leu Leu Leu Gly Glu Leu Gln Ala Leu Arg
                245                 250                 255

Asp Phe Ala Gln Leu Gly Ser Ala His Phe Trp Gly Met Met Thr Leu
            260                 265                 270

Gly Gly Leu Phe Gly Phe Ala Ile Gly Tyr Val Thr Gly Leu Gln Ile
```

-continued

```
                275                 280                 285
Lys Phe Thr Ser Pro Leu Thr His Asn Val Ser Gly Thr Ala Lys Ala
    290                 295                 300
Cys Ala Gln Thr Val Leu Ala Val Leu Tyr Tyr Glu Glu Thr Lys Ser
305                 310                 315                 320
Phe Leu Trp Trp Thr Ser Asn Met Met Val Leu Gly Gly Ser Ser Ala
                325                 330                 335
Tyr Thr Trp Val Arg Gly Trp Glu Met Lys Lys Thr Pro Glu Glu Pro
            340                 345                 350
Ser Pro Lys Asp Ser Glu Lys Ser Ala Met Gly Val
            355                 360

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 5
gcaagcttcc gccatgaata gggcccctct gaagcgg                              37

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 6
gctctagatc acaccccat ggcgctcttc tcgc                                  34

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 7
gcaagcttcc gccatggaga agcccttctct gctgcgggca ttgcagatcg cgc           53

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 8
gctctagatc acaccccat ggcgctcttc tcgc                                  34

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 9
```
gagatggagg tgacccagta gaga                                           24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 10
gagagagacg accagcgcga tctg                                           24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 11
gccattggct atgtgacagg actg                                           24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 12
gcagatcaaa ttcaccagtc ccc                                            23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 13
gaacttcacc caagccatgt gac                                            23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 14
cttgggttca gtcccaggtc                                                20

<210> SEQ ID NO 15
<211> LENGTH: 18
<212> TYPE: PRT
<213> ORGANISM: Homo sapiens

<400> SEQUENCE: 15

Asp Glu Ser Ile Tyr Ser Asn Tyr Tyr Leu Tyr Glu Ser Ile Pro Lys
 1               5                  10                  15

Pro Cys

```
<210> SEQ ID NO 16
<211> LENGTH: 19
<212> TYPE: DNA
<213> ORGANISM: Cricetulus griseus

<400> SEQUENCE: 16
gcgcctaacc ttctataac                                                  19

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
gctctagaga attcaaggtc gggcaggaag agggcctatt tc                        42

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
cgggatcctt cacgtgtttc gtcctttcca caagatatat aaagcc                    46

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
cagatctgcg gccgcgagct                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
cgcggccgca gatctgagct                                                 20

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
cgggatccaa ggtcgggcag gaagagggcc tatttcc                              37

<210> SEQ ID NO 22
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
cggaattctt cacgtgtttc gtcctttcca caagatatat aaagcc            46

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
cgcgcctaac cttctataac tttttg                                  26

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gatccaaaaa gttatagaag gttaggcgcg                              30

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
cgttatagaa ggttaggcgc tttttt                                  26

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
aattaaaaaa gcgcctaacc ttctataacg                              30

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
tctggcgcct gactttctac aacaa                                   25

<210> SEQ ID NO 28
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
accatcatgt tgctcgtcca ccaga                                           25

<210> SEQ ID NO 29
<211> LENGTH: 2609
<212> TYPE: DNA
<213> ORGANISM: Mus musculus

<400> SEQUENCE: 29
gagccgaggg tggtgctgca ggtgcacccg agggcaccgc cgagggtgag caccaggtcc     60
ctgcatcagc caggacacca gagcccagtc gggtggacgg acgggcgcct ctgaagcggt    120
ccaggatcct gcgcatggcg ctgactggag tctctgctgt ctccgaggag tcagagagcg    180
ggaacaagcc atttctgctc cgggctctgc agatcgcgct ggtggtctct ctctactggg    240
tcacctccat ttccatggta ttcctcaaca gtacctgct ggacagcccc tccctgcagc     300
tggatacccc cattttgtc accttctacc aatgcctggt gacctcactg ctgtgcaagg     360
gcctcagcac tctggccacc tgctgccccg gcatggtaga cttccccacc ctaaacctgg    420
acctcaaggt ggcccgaagt gtgctgccgc tgtcagtggt ctttatcggc atgataaacct    480 tcaataacct ctgcctcaag tacgtagggg tgcccttcta caacgtggga cgctcgctca    540
ccaccgtgtt caacgttctt ctctcctacc tgctgctcaa acagaccact tccttctatg    600
ccctgctcac ctgcggcgtc atcattggtg gtttctggct gggtatagac caagaaggag    660
ctgagggaac cttgtccctg acgggcacca tcttcggggt gctggccagc ctctgcgtct    720
ccctcaatgc catctatacc aagaaggtgc tccctgcagt agaccacagt atctggcgcc    780
taarrttcta taacaatgtc aatgcctgcg tgctcttctt gccccctgatg atagtgctgg    840 gcgagctccg tgccctcctg gccttcactc atctgagcag tgcccacttc tggctcatga    900
tgacgctggg tggcctgttt ggctttgcca tcggctatgt gacaggactg cagatcaaat    960
tcaccagtcc cctgacccat aacgtgtcag gcacggccaa ggcctgtgca cagacagtgc   1020
tggccgtgct ctactacgaa gagattaaga gcttcctgtg gtggacaagc aacctgatgg   1080
tgctgggtgg ctcctccgcc tacacctggg tcagggctg ggagatgcag aagacccagg    1140 aggacccag ctccaaagat ggtgagaaga gtgctatcag ggtgtgagct ccttcaggga    1200
gccagggctg agctcgggtg gggcctgccc agcacggaag gcttcccata gagcctactg   1260
cctatggccc tgagcaataa tgtttacatc cttctcagaa gaccatctaa gaagagccag   1320
gttctttcct gataatgtca gaaagctgcc aaatctcctg cctgccccat cttctagtct   1380
tgggaaagcc ctaccaggag tggcacccct cctgcctcct cctggggcct gtctacctcc   1440
atatggtctc tggggttggg gccagctgca ctctttgggc actggactga tgaagtgatg   1500
tcttactttc tacacaaggg agatgggttg tgaccctact atagctagtt gaagggagct   1560
gtgtaacccc acatctctgg ggccctgggc aggtagcata atagctaggt gctattaaca   1620
tcaataacac ttcagactac ctttggaggc agttgggagc tgagccgaga gagagagatg   1680
gccattctgc cctcttctgt gtggatgggt atgacagacc aactgtccat ggggtgactg   1740
acacctccac acttcatatt ttcaacttta gaaaaggggg agccacacgt tttacagatt   1800
aagtggagtg atgaatgcct ctacagcccc taaccccact ttccctgcct ggcttctctt   1860
```

```
ggcccagaag ggccaccatc ctgttctcca acacctgacc cagctatctg gctatactct    1920
ctttctgtac tcccttcccc ttccccccc cattagcctc ctccccaaca cctccatctt    1980
caggcaggaa gtggggtcca ctcagcctct gttcccatct gcttggaccc ctgagcctct    2040
catgaaggta ggcttatgtt ctctgaggct ggggccggag gagcgcactg attctcggag    2100
ttatcccatc aggctcctgt cacaaaatag cctaggccgt gtgtctaaga acagtggagg    2160
ttggcttata actgttctgg gggcagcgaa gcccacatca aggtactcat agacccagta    2220
tttctgagga aacccctgtc cacatcctca cttggtaaag gcacagataa tctccctcag    2280
gcctcttgta taggagcact agccctggga gggctccgcc ccatgacctg atcaccccaa    2340
agccttcaac agaaggattc caacatgaat ttggggacag aagcactcag accacgatgc    2400
ccagcaccac accctcctat cctcagggta gctgtcactg tcctagtccc ttctgtttgg    2460
ccttttgtac cctcatttcc ttggcgtcat gtttgatgtc tttgtctctt tcgtgagaag    2520
atggggaaac catgtcagcc tctgcttccg acttcccatg ggttctaatg aagttggtgg    2580
ggcctgatgc cctgagttgt atgtgattt                                      2609

<210> SEQ ID NO 30
<211> LENGTH: 1053
<212> TYPE: DNA
<213> ORGANISM: Rattus norvegiucus

<400> SEQUENCE: 30
atggcgctga ctggagcctc tgctgtctct gaggaggcag acagcgagaa caagccattt      60
ctgctacggg ctctgcagat cgcgctggtg gtttctctct actgggtcac ctccatctcc     120
atggtattcc tcaacaagta cctgctggac agccctcccc tgcagctgga taccccccatc   180 ttcgtcacct tctaccaatg cctggtgacc tcactgctgt gcaagggcct cagcactctg     240
gccacctgct gccctggcat ggtagacttc cccaccctaa acctggacct caaggtggcc     300
cgaagtgtgc tgccgctgtc cgtggtcttt atcggcatga taaccttcaa taacctctgc     360
ctcaagtacg tgggggtggc cttctacaac gtgggacgct cgctcactac cgtgttcaat     420
gtgcttctct cctacctgct gcttaaacag accacttcct tttatgccct gctcacctgt     480
gccatcatca ttggtggttt ctggctggga atagatcaag agggagctga gggcaccctg     540
tccctgacgg gcaccatctt cggggtgctg gccagcctct gtgtctcact caatgccatc     600
tacaccaaga aggtgctccc tgccgtagac acacagtatct ggcgcctaac cttctataac     660
aacgtcaacg cctgtgtgct cttcttgccc ctgatggtag tgctgggcga gctccatgct     720
ctcctggcct tcgctcatct gaacagcgcc cacttctggg tcatgatgac gctgggtgga     780
ctcttcggct ttgccattgg ctatgtgaca ggactgcaga tcaaattcac cagtcccctg     840
acccataatg tgtcgggcac agccaaggcc tgtgcacaga cagtgctggc tgtgctctac     900
tatgaagaga ttaagagctt cctgtggtgg acaagcaact tgatggtgct gggtggctcc     960
tctgcctaca cctgggtcag gggctgggag atgcagaaga cccaggagga ccccagctcc    1020
aaagagggtg agaagagtgc tatcggggtg tga                                 1053

<210> SEQ ID NO 31
<211> LENGTH: 350
<212> TYPE: PRT
<213> ORGANISM: Mus musculus

<400> SEQUENCE: 31
```

Met Ala Leu Thr Gly Val Ser Ala Val Ser Glu Glu Ser Glu Ser Gly
1               5                   10                  15

Asn Lys Pro Phe Leu Leu Arg Ala Leu Gln Ile Ala Leu Val Val Ser
                20                  25                  30

Leu Tyr Trp Val Thr Ser Ile Ser Met Val Phe Leu Asn Lys Tyr Leu
            35                  40                  45

Leu Asp Ser Pro Ser Leu Gln Leu Asp Thr Pro Ile Phe Val Thr Phe
        50                  55                  60

Tyr Gln Cys Leu Val Thr Ser Leu Leu Cys Lys Gly Leu Ser Thr Leu
65                  70                  75                  80

Ala Thr Cys Cys Pro Gly Met Val Asp Phe Pro Thr Leu Asn Leu Asp
                85                  90                  95

Leu Lys Val Ala Arg Ser Val Leu Pro Leu Ser Val Val Phe Ile Gly
            100                 105                 110

Met Ile Thr Phe Asn Asn Leu Cys Leu Lys Tyr Val Gly Val Pro Phe
        115                 120                 125

Tyr Asn Val Gly Arg Ser Leu Thr Thr Val Phe Asn Val Leu Leu Ser
    130                 135                 140

Tyr Leu Leu Leu Lys Gln Thr Thr Ser Phe Tyr Ala Leu Leu Thr Cys
145                 150                 155                 160

Gly Val Ile Ile Gly Gly Phe Trp Leu Gly Ile Asp Gln Glu Gly Ala
                165                 170                 175

Glu Gly Thr Leu Ser Leu Thr Gly Thr Ile Phe Gly Val Leu Ala Ser
            180                 185                 190

Leu Cys Val Ser Leu Asn Ala Ile Tyr Thr Lys Lys Val Leu Pro Ala
        195                 200                 205

Val Asp His Ser Ile Trp Arg Leu Thr Phe Tyr Asn Asn Val Asn Ala
    210                 215                 220

Cys Val Leu Phe Leu Pro Leu Met Ile Val Leu Gly Glu Leu Arg Ala
225                 230                 235                 240

Leu Leu Ala Phe Thr His Leu Ser Ser Ala His Phe Trp Leu Met Met
                245                 250                 255

Thr Leu Gly Gly Leu Phe Gly Phe Ala Ile Gly Tyr Val Thr Gly Leu
            260                 265                 270

Gln Ile Lys Phe Thr Ser Pro Leu Thr His Asn Val Ser Gly Thr Ala
        275                 280                 285

Lys Ala Cys Ala Gln Thr Val Leu Ala Val Leu Tyr Tyr Glu Glu Ile
    290                 295                 300

Lys Ser Phe Leu Trp Trp Thr Ser Asn Leu Met Val Leu Gly Gly Ser
305                 310                 315                 320

Ser Ala Tyr Thr Trp Val Arg Gly Trp Glu Met Gln Lys Thr Gln Glu
                325                 330                 335

Asp Pro Ser Ser Lys Asp Gly Glu Lys Ser Ala Ile Arg Val
            340                 345                 350

<210> SEQ ID NO 32
<211> LENGTH: 350
<212> TYPE: PRT
<213> ORGANISM: Rattus norvegiucus

<400> SEQUENCE: 32

Met Ala Leu Thr Gly Ala Ser Ala Val Ser Glu Glu Ala Asp Ser Glu
1               5                   10                  15

Asn Lys Pro Phe Leu Leu Arg Ala Leu Gln Ile Ala Leu Val Val Ser
                20                  25                  30

```
Leu Tyr Trp Val Thr Ser Ile Ser Met Val Phe Leu Asn Lys Tyr Leu
         35                  40                  45

Leu Asp Ser Pro Ser Leu Gln Leu Asp Thr Pro Ile Phe Val Thr Phe
     50                  55                  60

Tyr Gln Cys Leu Val Thr Ser Leu Leu Cys Lys Gly Leu Ser Thr Leu
 65                  70                  75                  80

Ala Thr Cys Cys Pro Gly Met Val Asp Phe Pro Thr Leu Asn Leu Asp
                 85                  90                  95

Leu Lys Val Ala Arg Ser Val Leu Pro Leu Ser Val Val Phe Ile Gly
                100                 105                 110

Met Ile Thr Phe Asn Asn Leu Cys Leu Lys Tyr Val Gly Val Ala Phe
            115                 120                 125

Tyr Asn Val Gly Arg Ser Leu Thr Thr Val Phe Asn Val Leu Leu Ser
        130                 135                 140

Tyr Leu Leu Leu Lys Gln Thr Thr Ser Phe Tyr Ala Leu Leu Thr Cys
145                 150                 155                 160

Ala Ile Ile Ile Gly Gly Phe Trp Leu Gly Ile Asp Gln Glu Gly Ala
                165                 170                 175

Glu Gly Thr Leu Ser Leu Thr Gly Thr Ile Phe Gly Val Leu Ala Ser
            180                 185                 190

Leu Cys Val Ser Leu Asn Ala Ile Tyr Thr Lys Val Leu Pro Ala
        195                 200                 205

Val Asp His Ser Ile Trp Arg Leu Thr Phe Tyr Asn Asn Val Asn Ala
    210                 215                 220

Cys Val Leu Phe Leu Pro Leu Met Val Val Leu Gly Glu Leu His Ala
225                 230                 235                 240

Leu Leu Ala Phe Ala His Leu Asn ser Ala His phe Trp Val Met Met
                245                 250                 255

Thr Leu Gly Gly Leu Phe Gly Phe Ala Ile Gly Tyr Val Thr Gly Leu
                260                 265                 270

Gln Ile Lys Phe Thr Ser Pro Leu Thr His Asn Val Ser Gly Thr Ala
        275                 280                 285

Lys Ala Cys Ala Gln Thr Val Leu Ala Val Leu Tyr Tyr Glu Glu Ile
    290                 295                 300

Lys Ser Phe Leu Trp Trp Thr Ser Asn Leu Met Val Leu Gly Gly Ser
305                 310                 315                 320

Ser Ala Tyr Thr Trp Val Arg Gly Trp Glu Met Gln Lys Thr Gln Glu
                325                 330                 335

Asp Pro Ser Ser Lys Glu Gly Glu Lys Ser Ala Ile Gly Val
                340                 345                 350

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      DNA

<400> SEQUENCE: 33
gcgccuaacc uucuauaac                                                  19

<210> SEQ ID NO 34
<211> LENGTH: 7752
<212> TYPE: DNA
<213> ORGANISM: Mus musculus
```

<400> SEQUENCE: 34

```
agcgttgcaa gttcagccga gggtggtgct gcaggtgcac ccgagggcac cgccgagggt      60
gagcaccagg tccctgcatc agccaggaca ccagagccca gtcgggtgga cggacggtac     120
gttctggaag ggaaagggcc ccgggaaggg gatacagcat tgagaagctc agaggctttg     180
gtctgggcat ccagaatgga ctttatctgg aggaggtgac atggcttctc gcctctggaa     240
gtgctgcttg gatctccggg acttcatgtc ctgactaggt ctggaagcgg tgaaaatagg     300
ggtaggaaaa aaggagagga ctgcaacaag gtcttcccga gtggcctgag ctcgagggac     360
gagggaggtg caacggtggg gagccgggcg caagggctgg gcggagggag ggggggggtc     420
tccctaagca gaaaggtggt attccatttt ctgggtagat ggtgaagatg cacctgaccg     480
agtctggtcg atctgaagat atcagggaa aagatagtgc gggtggaggg gagaatgaca     540
gaaccttcca gaaatggga gaggctatag cacttgcaaa cccttccctg atctccgggg     600
actcccggaa gaagagggca ggtctgtggg cataggtgca gacttgccgg ggagctcttg     660
acggccgcgg gaagtggcaa cggcctgcga gctggccctt taaggcggct cgtaggcgtg     720
tcaggaaatg cgcgcagggc ccgccctgct cggtaagtgg cccgggaccc gcgtcgctga     780
gccgaacttt gaattcggct cgtggcaacc gcagggcctt gctccggtca ggcccctgtc     840
cgtgtccctc gagacgcctt cctgagcctc ggtgatctcc ctgcagcacg ccctcctttc     900
ggctctgcgg gtgcttccgg gggttcccgc agcccatgct tcccacgcgg tccgcgtcca     960
gttatttcct cctccgctcc gtccttcctt cgctctctcg cttcctttct ccctgcgact    1020
cacgtgtccc ctgtcctcaa actggccatg gctgtcaaag cccacatcct tagttaggcc    1080
ccttctccct tccctgggtc ttgtttcgtg acaccacctc cctcccccgc ccgggagcg     1140
agcaagatga ggagcggtgc acctcggcaa atccggaagc agaacttcat ccaagaagga    1200
ggggaccgat aggtcatccc atgtgacagt tgaaggctgc agccacagac cctagctgct    1260
tgaagccctg tagtccaggg actgcttctg gccgtaaggt gacccagctc ttctgccacc    1320
atgaacaggc gcctctgaa gcggtccagg atcctgcgca tggcgctgac tggagtctct    1380
gctgtctccg aggagtcaga gagcgggaac aagccatttc tgctccgggc tctgcagatc    1440
gcgctggtgg tctctctcta ctgggtcacc tccatttcca tggtattcct caacaagtac    1500
ctgctggaca gcccctccct gcagctggat acccccattt ttgtcacctt ctaccaatgc    1560
ctggtgacct cactgctgtg caagggcctc agcactctgg ccacctgctg ccccggcatg    1620
gtagacttcc ccaccctaaa cctggacctc aaggtggccc gaagtgtgct gccgctgtca    1680
gtggtcttta tcggcatgat aaccttcaat aacctctgcc tcaagtacgt agggggtgccc    1740
ttctacaacg tgggacgctc gctcaccacc gtgttcaacg ttcttctctc ctacctgctg    1800
ctcaaacaga ccacttcctt ctatgccctg ctcacctgcg gcgtcatcat tggtgagtgg    1860
gactgggggc gtggggagca ggaatcgtaa agatcaatac cacattactc attatctgtc    1920
ccaggtcttt tgcaccacca gtcataggga gagacctgta gagaacaaat aacttcctta    1980
ctgtgactca gtaagttagg gatccagcca aggtgaacat aataatgtta ggcagacact    2040
acagcaaagc cagccagaca ctcagatcta gctaagcatt tgagccatgt taatgtaacg    2100
gatccccatt acaaggtata atatagctgc gttttatgga gagaaaccca aggcacagag    2160
aagctaagta gctgggatca cacaggtaat cactgacgta gcagaaattt gcacataagc    2220
agttacctcc ataggttaca ctcttgacca acacaccact gttctcaaga ggtcaagggt    2280
```

```
gaactcaggt catcacaatt ggcacaagta cctctaccca ctgagccatt tcagtggtcc    2340
agtcaatatg tgtgtgcttt aagaggcttt aactaccttc tcagatgtga ccataagtaa    2400
ttaattaccg ataggagcgt tgtgctgatc attacacttg tagcatcctc tttattgtac    2460
ccataagctc tctgagtggc ggcatctctg tgaaactgca gctcggagag gctgcgctcc    2520
ttgccacagc cccacaacta agaagcagat agtctgggac gcagtcccca gttggtcata    2580
ctccctggcc tgtgtttcaa gccagtctgc tttgctcctg acccttggga gttagcgcaa    2640
tgaaaaccaa cactatcact acagtctaaa tgtgctttta aatgaaagcc caggaacttt    2700
gaagcatccg gcccccttaac ggcagccact atgtcctgat ccgccaaca tcttttcagt    2760 gcccggcagt cacatggagc aagggcctct tggcttggac agcatgtgtt agggaacatg    2820
tttgccactt tgaatgaatt tagtggctgc tgggttacag agaccagggc atctttcccc    2880
tcagagtcct gaatgaacga aaagcaacct tcatttgtac ctgctctgga ttttagttcg    2940
tcttgtttgg cctatttaga tgtccctggt gtctctgagg cccaggctgg gtgctctaga    3000
tgtagggacc aggccaacct gtactgtctt ccctagaaac attgccctgg ttgggcagct    3060
cctggatcca gggttaaggg gtctgggcgg agagaggtca gatagtggca ggatgcctcc    3120
cactgccccc acatacatac cctaagagat ctggtactcc tccttccagc ctacaagcta    3180
ccgtggggtc ccacttcagt ccaccagccc tgccaacgtt agaggggatg ggcctcctag    3240
taggagaact tacatgcagg aaggtacagt ctctggagaa cctgagcccg ggtccccaaa    3300
gggacaagta gctgatagtg aggcagctga gccccatggc ggcctgccca gtggcacgg    3360 gaaagtggag ctctctgctg cccccactac tggccccatc tcttggctct cccctccctt    3420
cctcctgtgg agaaggccca tctctggaaa ggcctcctag acatgcggca ctttgcaaag    3480
cctgtcgggc tcacagcccc tctagggtct aggaccttga gaatgaagaa tggagtcact    3540
tctagactct agtggtaacc accaggaggt acagggtgct ctgactgtgc agggaaaccc    3600
accgtgggct ctgctgagcc aagtgcctgt gaggctggag agtctggtgc ccttgttctg    3660
agatagcatc ttgctatgtt gccctcaagt cccaggcaac tggggctgca ggagcaccac    3720
cttgcctctc tccagcttct tgaagacttg tacctttctc ctagcagtct ctatctgctc    3780
tcactccatc cattgagcag ctattagctt gtggccaagt attttccagg ccctgtactg    3840
agttttaggg tacaagtttg agaaaggaag ggtgggtcc ttgctcctgg tccgtgaatg    3900
atgttgatgg cagaaacgat agttacacta gatgctaagg gctgtgggta tctagaggga    3960
gcagggagca tgtgggataa cctgagcagg cctagctgaa aagtcattgc tggcatgaga    4020
ctgctccagt agtacaggct gggaacacac atttgaatgt tcctgaaga cagttgggag    4080 ccacaggaaa tatccactgt agaaagatta tttagttgta agacagagta gtagattggt    4140
taacatagta gcaaaaacgt ggccccagtt tttacagatg aagggaattg gaactcagag    4200
aggttaagta acttctccca agcagctcag ctacaaaaat cacagaacag gcaggggcct    4260
gatggctctg atgcctgtgc tggtcccact attccatgtt gctaattcct gcagcagcag    4320
taaacctctg ccttgtggaa atgaggagtc taaataaaga gaccatagca ttgccacaag    4380
caggtttcta ccaactgggg gtggcaagga atgctgtgtt agcagcagga agctgggaag    4440
aggctgagta ctgggggat gaggaaggga tccccaggag aggctgactt tggccttgaa    4500
gaatggtgga gtccctggaa agatgcagat acacagagct ctgtggatat acagagaagt    4560
ggggagctaa gtaggtggct tggggccatc atgtgacaga ggaagtcggg ctagatgcag    4620
gaagcccggt gctgtggcct agggagccat gtaggttctt tgagcagggg gcggggggg    4680
```

```
gggggggtga cccaggagtg actgtaaaca acatcaggcc atgagcagct ctgacctaat    4740
gttctcacca agggagccag aaccaaggct tagagccctg tccctttta gtgtccaagg    4800 tcactttact ggccctcttc ctttacagct gttggccccc acaggccatc aggcacctat    4860
gctattttat tttatagcct tcattacaat gactacaatt gtaattagag agttgacagg    4920
gtcacatctg tccttatata ttccccctct gctaagttct gcctgggaga atgtggaggg    4980
tattggtgaa atttggggaa gttataaccc cccaccct gccccaccc cctgctttgc    5040 tccctttatc tgcagggcat ttctgtgccc actttagccc atatagctcc caaataaatg    5100
acacagaaac ctggtatttt cattaacaaa ctgctggcac tctgctgggc aggttctgag    5160
ctgttctaac cctctaagct gctaatgccc agatagatgc cccaatgctt gccatccgag    5220
tctttctctg gcttgctctg ctccatgtgt gacctcatgg tgaatcctcc tgatttcccc    5280
acatggcctc tccacacttt tccttctccc ctctctctac cagggaccct ctcactggga    5340
cccgatgtcc catctgtact gtcctctccc acccagtcat aggctgattg agtctttatt    5400
aaccaatcag agatgatgga aaaacagttt ttacatagca ctgaggatgg agatgcttga    5460
cccttgagat gcttgcccgt aacctgtact gtatccagat gtctgggccc ccaaatcagc    5520
aggtgaatac acagtacaca ggactgaccc ccaacagagg gggaacacag gttctcactc    5580
tgggctccac gccctcggcc cttcttagt gcaggggtta gactttgtat gtgttgatga    5640
tgaggtaagg gccatggaac agtcagaacg gtggtgtcag aatcctgtcc ctctccctcc    5700
tgtcctcatc cctccttacc gtgtcactct tctgtctgtt gcaggtggtt tctggctggg    5760
tatagaccaa gaaggagctg agggaacctt gtccctgacg ggcaccatct tcggggtgct    5820
ggccagcctc tgcgtctccc tcaatgccat ctataccaag aaggtgctcc ctgcagtaga    5880
ccacagtatc tggcgcctaa ccttctataa caatgtcaat gcctgcgtgc tcttcttgcc    5940
cctgatgata gtgctgggcg agctccgtgc cctcctggcc ttcactcatc tgagcagtgc    6000
ccacttctgg ctcatgatga cgctgggtgg cctgtttggc tttgccatcg gctatgtgac    6060
aggactgcag atcaaattca ccagtcccct gacccataac gtgtcaggca cggccaaggc    6120
ctgtgcacag acagtgctgg ccgtgctcta ctacgaagag attaagagct tcctgtggtg    6180
gacaagcaac ctgatggtgc tgggtggctc ctccgcctac acctgggtca ggggctggga    6240
gatgcagaag acccaggagg acccccagctc caaagatggt gagaagagtg ctatcagggt    6300
gtgagctcct tcagggagcc agggctgagc tcgggtgggg cctgcccagc acggaaggct    6360
tcccatagag cctactgggt atggccctga gcaataatgt ttacatcctt ctcagaagac    6420
catctaagaa gagccaggtt cttcctgat aatgtcagaa agctgccaaa tctcctgcct    6480
gccccatctt ctagtcttgg gaaagcccta ccaggagtgg cacccttcct gcctcctcct    6540
ggggcctgtc tacctccata tggtctctgg ggttggggcc agctgcactc tttgggcact    6600
ggactgatga agtgatgtct tactttctac acaagggaga tgggttgtga ccctactata    6660
gctagttgaa gggagctgtg taaccccaca tctctgggc cctgggcagg tagcataata    6720
gctaggtgct attaacatca ataacacttc agactaccttt ggaggcagt tgggagctga    6780 gccgagagag agagatggcc attctgccct cttctgtgtg gatgggtatg acagaccaac    6840
tgtccatggg gtgactgaca cctccacact tcatattttc aactttagaa aagggggagc    6900
cacacgtttt acagattaag tggagtgatg aatgcctcta cagcccctaa ccccactttc    6960
cctgcctggc ttctcttggc ccagaagggc caccatcctg ttctccaaca crtgacccag    7020
```

```
ctatctggct atactctctt tctgtactcc cttcccctto cccccccoat tagcctcctc    7080 cccaacacct ccatcttcag gcaggaagtg gggtccactc agcctctgtt cccatctgct    7140 tggaccoctg agcctctcat gaaggtaggc ttatgttctc tgaggctggg gccggaggag    7200
cgcactgatt ctcggagtta tcccatcagg ctcctgtcac aaaatagcct aggccgtgtg    7260
tctaagaaca gtggaggttg gcttataact gttctggggg cagcgaagcc cacatcaagg    7320
tactcataga cccagtattt ctgaggaaac ccctgtccac atcctcactt ggtaaaggca    7380
cagataatct ccctcaggcc tcttgtatag gagcactagc cctgggaggg ctccgcccca    7440
tgacctgatc accccaaagc cttcaacaga aggattccaa catgaatttg gggacagaag    7500
cactcagacc acgatgccca gcaccacacc ctcctatcct cagggtagct gtcactgtcc    7560
tagtcccttc tgtttggcct tttgtaccct catttccttg gcgtcatgtt tgatgtcttt    7620
gtctctttcg tgagaagatg gggaaaccat gtcagcctct gcttccgact tcccatgggt    7680
tctaatgaag ttggtggggc ctgatgccct gagttgtatg tgatttaata aaaaaaaaat    7740
ttttttaaaa ac                                                        7752

<210> SEQ ID NO 35
<211> LENGTH: 4039
<212> TYPE: DNA
<213> ORGANISM: Cricetulus griseus

<400> SEQUENCE: 35
gaacttcacc caagccatgt gacaattgaa ggctgtaccc ccagaccccta acatcttgga     60 gccctgtaga ccagggagtg cttctggccg tggggtgacc tagctcttct accaccatga    120
acagggcccc tctgaagcgg tccaggatcc tgcgcatggc gctgactgga ggctccactg    180
cctctgagga ggcagatgaa gacagcagga acaagccgtt tctgctgcgg gcgctgcaga    240
tcgcgctggt cgtctctctc tactgggtca cctccatctc catggtattc ctcaacaagt    300
acctgctgga cagcccctcc ctgcagctgg ataccccctat cttcgtcact ttctaccaat    360
gcctggtgac ctctctgctg tgcaagggcc tcagcactct ggccacctgc tgccctggca    420
ccgttgactt ccccaccctg aacctggacc ttaaggtggc ccgcagcgtg ctgccactgt    480
cggtagtctt cattggcatg ataagtttca ataacctctg cctcaagtac gtaggggtgg    540
ccttctacaa cgtgggcgc tcgctcacca ccgtgttcaa tgtgcttctg tcctacctgc    600
tgctcaaaca gaccacttcc ttctatgccc tgctcacatg tggcatcatc attggtgagt    660
ggggcccggg ggctgtggga gcaggatggg catcgaactg aagccctaaa ggtcaacact    720
gtaggtacct ttacttactg tcccaggtcc cttgcatcag cagttacagg aagagccctg    780
tagaaaacaa ataacttcct tatggtcatt caacaagtta gggacccagc cagggtgaaa    840
ataatgttag cagcaactac agcaaagatg gctctcgcca cttgcatgat taaaatgtgc    900
caggtactca gatcyaagca ttggatccac attaactcaa ctaatcccta ttacaaggta    960
aaatatatcc gaattttaca gagggaaaac caaggcacag agaggctaag tagcttgacc   1020
aggatcacac agctaataat cactgacata gctgggattt aaacataagc agttacctcc   1080
atagatcaca ctatgaccac catgccactg ttccttctca agagttccag gatcctgtct   1140
gtccagttct ctttaaagag gacaacacat ctgacattgc tacccttgagg taacatttga   1200 aatagtgggt agacatatgt tttaagtttt attcttrctt tttatgygtg tgtgtttggg   1260
gggccaccac agtgtatggg tggagataag gggacaactt aagaattggt cctttctccc   1320
accacatggg tgctgaggtc tgaactcagg tcatcaggat tggcacaaat cccttttaccc   1380
```

```
actgagccat tcactggtc caatatatgt gtgctttaa gaggctttaa ctattttccc    1440
agatgtgaat gtcctgctga tcattatccc cttttacccg gaagccctct gggaggtgcc    1500
atccctgtgg tcgtctgcat acaaatgggg aaactgcaac tcagagaaac aaggctactt    1560
gccagggccc cacaagtaag ataggctggg atgccatccc agactggcca cactccctgg    1620
cctgtgcttc aagccagttt actttgttcc tgcccattgg aagttagcat gttgcagtca    1680
aacacaataa ctacaggcca aaagtgcttt taaattaaag tcagatgaac ttttaaacat    1740
ccagagctcc tcaactgcag gagttacaac ctgattctgc aaccatcttt gcagtgcccg    1800
gtagtcatat gtagctagag gctcttggct aggacagcat gtgttaggaa acatctggcc    1860
ctgagatcat tgaattgagt gactgctggg tgacaaagac caaggcatcc gttccctgag    1920
agtcctgggc aagcagcaat gtgaccttca tttgtaccta ctcaggttct ttatctgtcc    1980
tgtttgacct acttagtctc ctctggtgtc tcagaggccc aggctgggta ctctggatgt    2040
caggatcagg ccaatgcgca catctgccct agaaatgtcc ccctggttga gcagctcctg    2100
aatccatcgg taaagggtct ggaccaggga ggagtcagat aaaaagctga cagcactggg    2160
ggactccatg gggaactccc acctgccccc acacatccat cctaagagaa ctggtattcc    2220
ttgtttcctc tttgtcctac aaggcaccct gggatcccac ttcagtctcc cagccttgcc    2280
agggttagag ggcatgagcc tccttgtggg gaatttagat gcaagaaggt acagtcacta    2340
gagaacctga gctcagatcc ccaaagtaac cagtacctga tagtgaggca gctgagaacc    2400
gcagcagcct gcctgagtgg ctgaactctg cggcctccgg aactggcccc aactgttggg    2460
tctcctcttc cttcctcctg tgagggaggg cccatctctg ataagtgctg tggggactct    2520
agagtaggga ggaggaggag caatctaagc aggccttact gagaagtcct tgctggcatg    2580
tggctgcctg aggagtacag actgggaaca cccatttgaa tgagtaaggt ttttcctgaa    2640
ggccatgggg agccacggag gaaaatcatt ttagttacaa gacaaagagt agattggtta    2700
acatgggagc arggacatgg ccccaatttt cattgatgaa ggaaattgga actcrgagag    2760
gttaagtaac ttctcccaaa tagctcagct tcataatcac agaacagtca gagtctagat    2820
ctctctgatg cctgtgatgg tcctgccatt ccatgttgct gatccctgtg gcatcagtaa    2880
gcctctacct tgtgggaatg caggatctaa atgaagagag raagtgctgg ccccatgctg    2940
tggtctggaa agctatgcag gctctttgag cagagagtga cccacaagtg aatagagtcc    3000
tatgagactc aaagcaacat ccacccttaa gcagctctaa ccaaatgctc acactgaggg    3060
agccaaagcc aagttagagt cctgtgcttg cccaaggtca ctttgcctgg ccctcctcct    3120
atagcacccg tgttatctta tagccctcat tacagtgatt acaattataa ttagagaggt    3180
aacagggcca cactgtcctt acacattccc ctgctagatt gtagctggga gaggggagaa    3240
tgtaggtggc tggggagtg ggagggaaga tgcagatttt cattctgggc tctactccct    3300
cagccatttt ttggtgtggg agttagactt tggatatgtt gatgatgagg taagggccac    3360
agaacagtct gaactgtggt atcagaatcc tgtccctctc cctctctcct catccctctt    3420
caccttgtca ctcctctgtc tgctacaggt ggtttctggc tgggtataga ccaagaggga    3480
gctgagggca ccctgtccct cataggcacc atcttcgggg tgctggccag cctctgcgtc    3540
tccctcaatg ccatctatac caagaaggtg ctcccagcag tggacaacag catctggcgc    3600
ctaaccttct ataacaatgt caatgcctgt gtgctcttct tgcccctgat ggttctgctg    3660
ggtgagctcc gtgccctcct tgactttgct catctgtaca gtgcccactt ctggctcatg    3720
```

```
atgacgctgg gtggcctctt cggctttgcc attggctatg tgacaggact gcagatcaaa      3780
ttcaccagtc ccctgaccca caatgtatca ggcacagcca aggcctgtgc gcagacagtg      3840
ctggccgtgc tctactatga agagactaag agcttcctgt ggtggacaag caacctgatg      3900
gtgctgggtg gctcctcagc ctatacctgg gtcaggggct gggagatgca gaagacccaa      3960
gaggacccca gctccaaaga gggtgagaag agtgctattg gggtgtgagc ttcttcaggg      4020
acctgggact gaacccaag                                                   4039
```